(12) United States Patent
Chen et al.

(10) Patent No.: US 11,414,701 B2
(45) Date of Patent: Aug. 16, 2022

(54) MULTIMODAL READOUTS FOR QUANTIFYING AND SEQUENCING NUCLEIC ACIDS IN SINGLE CELLS

(71) Applicants: THE BROAD INSTITUTE, INC., Cambridge, MA (US); PRESIDENT AND FELLOWS OF HARVARD COLLEGE, Cambridge, MA (US); MASSACHUSETTS INSTITUTE OF TECHNOLOGY, Cambridge, MA (US)

(72) Inventors: Fei Chen, Cambridge, MA (US); Jesse Engreitz, Cambridge, MA (US); Jamie Marshall, Cambridge, MA (US); Vidya Subramanian, Cambridge, MA (US); Sam Rodriques, Cambridge, MA (US)

(73) Assignees: THE BROAD INSTITUTE, INC., Cambridge, MA (US); PRESIDENT AND FELLOWS OF HARVARD COLLEGE, Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 159 days.

(21) Appl. No.: 16/422,837

(22) Filed: May 24, 2019

(65) Prior Publication Data
US 2019/0360044 A1 Nov. 28, 2019

Related U.S. Application Data

(60) Provisional application No. 62/780,889, filed on Dec. 17, 2018, provisional application No. 62/676,069, filed on May 24, 2018.

(51) Int. Cl.
| C12Q 1/6874 | (2018.01) |
| C12Q 1/6876 | (2018.01) |
| C12N 15/10 | (2006.01) |

(52) U.S. Cl.
CPC ....... *C12Q 1/6874* (2013.01); *C12N 15/1086* (2013.01); *C12Q 1/6876* (2013.01); *C12Q 2600/16* (2013.01)

(58) Field of Classification Search
CPC .. C12Q 1/6874; C12Q 1/6876; C12Q 1/6869; C12Q 2600/16; C12N 15/1086; C12N 15/1075; C12N 15/1093
See application file for complete search history.

(56) References Cited

U.S. PATENT DOCUMENTS

| 7,632,641 B2 | 12/2009 | Dirks et al. |
| 7,708,949 B2 | 5/2010 | Stone et al. |

(Continued)

FOREIGN PATENT DOCUMENTS

| WO | 2004091763 A2 | 10/2004 |
| WO | 2006096571 A2 | 9/2006 |

(Continued)

OTHER PUBLICATIONS

Cusanovich, Darren A. et al., "Multiplex Single Cell Profiling of Chromatin Accessibility by Combinatorial Cellular Indexing", Science, vol. 348, Issue No. 6237, pp. 910-914, May 22, 2015.

(Continued)

*Primary Examiner* — Jeremy C Flinders
*Assistant Examiner* — Taryn Kimberly Wood
(74) *Attorney, Agent, or Firm* — F. Brent Nix, Esq.; Carin R. Miller, Esq.; Johnson, Marcou, Isaacs & Nix, LLC

(57) ABSTRACT

Provided herein are methods for generating single-cell molecular analysis comprising a) delivering one or more proximity dependent probes to a cell population, wherein (Continued)

each proximity dependent probe comprises a target binding region configured to bind a target RNA and a primer binding site region; b) linking bound proximity dependent probes; c) isolating single cells from the cell population in separate individual discrete volumes, the individual discrete volumes further comprising a primer pair and amplification reagents, wherein the primer pair binds to the primer binding sites of the ligation dependent probes, and wherein at least one primer comprises a barcode sequence that uniquely identifies the individual discrete volume; d) amplifying the ligated probes using the primer pair, wherein the barcode is incorporated into each resulting amplicon; and e) quantifying target RNAs in each individual cell based at least in part on sequencing the resulting amplicons.

40 Claims, 30 Drawing Sheets

Specification includes a Sequence Listing.

(56) References Cited

U.S. PATENT DOCUMENTS

| | | | |
|---|---|---|---|
| 8,337,778 | B2 | 12/2012 | Stone et al. |
| 8,765,485 | B2 | 7/2014 | Link et al. |
| 2016/0060691 | A1 | 3/2016 | Giresi et al. |
| 2016/0208323 | A1 | 7/2016 | Bernstein et al. |
| 2016/0305856 | A1 | 10/2016 | Boyden et al. |
| 2017/0067096 | A1 | 3/2017 | Wassie et al. |
| 2018/0010166 | A1 | 1/2018 | Pierce et al. |
| 2020/0224243 | A1* | 7/2020 | Desai ............... C12Q 1/682 |

FOREIGN PATENT DOCUMENTS

| | | | |
|---|---|---|---|
| WO | 2014047556 | A1 | 3/2014 |
| WO | 2014143158 | A1 | 9/2014 |
| WO | 2014144491 | A1 | 9/2014 |
| WO | 2014204727 | A1 | 12/2014 |
| WO | 2014210353 | A2 | 12/2014 |
| WO | 2015127183 | A2 | 8/2015 |
| WO | 2015164212 | A9 | 10/2015 |
| WO | 2016040476 | A1 | 3/2016 |
| WO | 2016100975 | A1 | 6/2016 |
| WO | 2016100976 | A2 | 6/2016 |
| WO | 2016168584 | A1 | 10/2016 |
| WO | 2016205728 | A1 | 12/2016 |
| WO | 2017075294 | A1 | 5/2017 |
| WO | 2017156336 | A1 | 9/2017 |
| WO | 2017164936 | A1 | 9/2017 |

OTHER PUBLICATIONS

Tang, Weixin et al., "Rewriteable Multi-Event Analog Recording in Bacterial and Mammalian Cells", Science, vol. 360, Issue No. 6385, pp. 1-23, Apr. 13, 2018.
Butcher, L.M. et al. "AutoMeDIP-seq: A high-throughput, whole genome, DNA methylation assay", Methods, vol. 52, No. 3, pp. 223-231, Available online: Apr. 10, 2010.
Karimi, Mohsen et al., "LUMA (LUminometric Methylation Assay)—A high throughput method to the analysis of genomic DNA methylation", Experimental Cell Research, vol. 312, No. 11, pp. 1989-1995, Available online: Apr. 19, 2006.
Cleary, Brian et al., "Composite measurements and molecular compressed sensing for highly efficient transcriptomics", Biorxiv, pp. 1-54, preprint first posted online Jan. 2, 2017.
Hodis, Eran et al., "A Landscape of Driver Mutations in Melanoma", Cell, vol. 150, pp. 251-263, Jul. 20, 2012.
Vogelstein, Bert et al., "Cancer Genome Landscapes", Science, vol. 339, pp. 1546-1558, Mar. 29, 2013.

Forbes, Simon A. et al., "COSMIC: somatic cancer genetics at high-resolution", Nucleic Acids Research, 2017, vol. 45, Database issue D777-D783, Published online: Nov. 29, 2016.
Burger JA, et al., "Clonal evolution in patients with chronic lymphocytic leukaemia developing resistance to BTK inhibition", Nature Communications, pp. 1-13, Published: May 20, 2016.
Landau DA, et al., "Mutations driving CLL and their evolution in progression and relapse", Nature, vol. 526, No. 7574, pp. 525-530, Oct. 22, 2015.
Landau DA, et al., "Clonal evolution in hematological malignancies and therapeutic implications", Leukemia, vol. 28, pp. 34-43, Jan. 2014.
Landau DA, et al., "Evolution and impact of subclonal mutations in chronic lymphocytic leukemia", Cell, vol. 152, pp. 714-726, Feb. 14, 2013.
Rooney, MS et al., "Molecular and genetic properties of tumors associated with local immune cytolytic activity", Cell, vol. 160, pp. 48-61, Jan. 15, 2015.
Nadal, Ernest et al., "A Novel Serum 4-microRNA Signature for Lung Cancer Detection", Scientific RepoRts | 5:12464 | DOi: 10.1038/srep12464, pp. 1-9, Published: Jul. 23, 2015.
Tirosh, Itay et al. "Dissecting the multicellular ecosystem of metastatic melanoma by single cell RNA-seq", Science, vol. 352, pp. 189-196, Apr. 8, 2016.
Tirosh et al., Single-cell RNA-seq supports a developmental hierarchy in human oligodendroglioma. Nature, vol. 539, Issue No. 7628, pp. 309-313, Nov. 10, 2016.
Choi, HMT et al., "Next-Generation in Situ Hybridization Chain Reaction: Higher Gain, Lower Cost, Greater Durability", ACS Nano., vol. 8, No. 5, pp. 4284-4294, 2014.
Margulies, Marcel et al., "Genome sequencing in microfabricated high-density picolitre reactors", Nature, vol. 437, pp. 376-380, Sep. 15, 2005.
Ronaghi, Mostaf et al., "Real-Time DNA Sequencing Using Detection of Pyrophosphate Release", Analytical Biochemistry, Article No. 0432, vol. 242, pp. 84-89.
Shendure, Jay et al., "Accurate Multiplex Polony Sequencing of an Evolved Bacterial Genome", Science, vol. 309, pp. 1728-1732, Sep. 9, 2005.
Imelfort, Michael et al., "De novo sequencing of plant genomes using second-generation technologies", Briefings in Bioinformatics, vol. 10, No. 6, pp. 609-618, Submitted: May 4, 2009.
Fox, Samuel et al., "Applications of Ultra-high-Throughput Sequencing", Methods of Molecular Biology, vol. 553, pp. 79-108, 2009.
Appleby, Nikki et al., "New Technologies for Ultra-High Throughput Genotyping in Plants", vol. 513, pp. 19-39, 2009.
Morozova, Olena et al., "Applications of next-generation sequencing technologies in functional genomics", Genomics, vol. 92, pp. 255-264, Available online: Aug. 24, 2008.
Fredriksson, Simon et al., "Protein detection using proximity-dependent DNA ligation assays", Nature Biotechnology, vol. 20, pp. 473-477, May 2002.
Gullberg, Mats et al., "Cytokine detection by antibody-based proximity ligation", Proc Natl Acad Sci USA, vol. 101, No. 22, pp. 8420-8424, Jun. 1, 2004.
Lundberg, Martin et al., "Homogeneous antibody-based proximity extension assays provide sensitive and specific detection of low-abundant proteins in human blood", Nucleic Acids Research, vol. 39, No. 15 e102, pp. 1-8, Published online: Jun. 6, 2011.
Boozer, Christina et al., "DNA directed protein immobilization on mixed ssDNA/oligo(ethylene glycol) self-assembled monolayers for sensitive biosensors", Anal. Chem., vol. 76, No. 23, pp. 6967-6972, Dec. 1, 2004.
Kozlov, Igor A. et al., "Efficient strategies for the conjugation of oligonucleotides to antibodies enabling highly sensitive protein detection", Biopolymers, pp. 621-630, First published: Mar. 8, 2004.
Nolan, Gary P., "Tadpoles by the tail", Nature Methods, vol. 2, No. 1, pp. 11-12, Published: Jan. 2005.
Stoeckius, Marlon et al., "Large-scale simultaneous measurement of epitopes and transcriptomes in single cells", Nature Methods, vol. 14, No. 9, pp. 865-868, Sep. 2017.

(56) References Cited

OTHER PUBLICATIONS

Soderberg, Ola et al., "Direct observation of individual endogenous protein complexes in situ by proximity ligation", Nature Methods, vol. 3, No. 12, pp. 995-1000, Dec. 2006.
Greenwood, Christina et al., "Proximity assays for sensitive quantification of proteins", Biomolecular Detection and Quantification, vol. 4, pp. 10-16, Available online: May 20, 2015.
Maroney, Patricia et al., "Direct detection of small RNAs using splinted ligation", Nature Protocols, vol. 3, No. 2, pp. 279-287, Published: Jan. 31, 2008.
Niedzicka, M. et al., Molecular Inversion Probes for targeted resequencing in non-model organisms, Scientific Reports | 6:24051 | DOI: 10.1038/srep24051 , pp. 1-9 Published: Apr. 5, 2016.
Islam, Saiful et al., "Quantitative single-cell rna-seq with unique molecular identifiers", Nature Methods | vol. 11 No. 2 | pp. 163-166 | Feb. 2014.
Macosko, E.Z. et al., "Highly Parallel Genome-wide Expression Profiling of Individual Cells Using Nanoliter Droplets", Cell, vol. 161, pp. 1202-1214, May 21, 2015.
Klein A.M. et al., "Droplet Barcoding for Single-Cell Transcriptomics Applied to Embryonic Stem Cells", Cell, vol. 161, pp. 1187-1201, May 21, 2015.
Zheng, et al., 2016, "Haplotyping germline and cancer genomes with high-throughput linked-read sequencing" Nature Biotechnology, vol. 34, pp. 303-311, Mar. 2016.
Zheng, et al., "Massively parallel digital transcriptional profiling of single cells" Nature Communications, vol. 8, pp. 1-12, Published: Jan. 16, 2017.
Zilionis, Rapolas et al., "Single-cell barcoding and sequencing using droplet microfluidics" Nat Protoc., vol. 12, Issue No. 1, pp. 44-73, 2017.
Cao, Junyue et al., "Comprehensive single cell transcriptional profiling of a multicellular organism by combinatorial indexing", Biorxiv, pp. 1-35, preprint first posted online Feb. 2, 2017.
Rosenberg Alexander et al., 2017, "Scaling single cell transcriptomics through split pool barcoding" Biorxiv, pp. 1-13, preprint first posted online Feb. 2, 2017.
Vitak, Sarah et al., "Sequencing thousands of single-cell genomes with combinatorial indexing" Nature Methods, vol. 14, No. 3, pp. 302-308, Mar. 2017.
Cao, Junyue et al., Comprehensive single-cell transcriptional profiling of a multicellular organism. Science, vol. 357 (6352), pp. 661-667, Aug. 18, 2017.
Gierahn, Todd et al., "Seq-Well: portable, low-cost RNA sequencing of single cells at high throughput" Nature Methods, vol. 14, pp. 395-398, Apr. 2017.
Chung, Kwanghun et al., "Structural and molecular interrogation of intact biological systems", Nature, vol. 497 (7449), pp. 332-337, May 16, 2013.
Quinodoz, Sophia et al. ,"Higher-order inter-chromosomal hubs shape 3-dimensional genome organization in the nucleus", Biorxiv, pp. 1-69, preprint first posted online Nov. 18, 2017.
Chen, Fei et al., "Expansion microscopy", Science, vol. 347 (6221), pp. 543-548, Jan. 30, 2015.
Chen, Fei et al., "Nanoscale Imaging of RNA with Expansion Microscopy", Nature Methods, vol. 13, No. 8, pp. 679-684, Aug. 2016.
Tillberg, Paul et al., "Protein-retention expansion microscopy of cells and tissues labeled using standard fluorescent proteins and antibodies", Nature Biotechnology, vol. 34, pp. 987-992, Sep. 2016.
Swiech, Lukasz et al., "In vivo interrogation of gene function in the mammalian brain using CRISPR-Cas9" Nature Biotechnology, vol. 33, pp. 102-106, Jan. 2015.
Habib, Naomi et al., "Div-Seq: Single-nucleus RNA-Seq reveals dynamics of rare adult newborn neurons", Science, vol. 353, Issue 6302, pp. 925-928, Aug. 26, 2016.
Habib, Naomi et al. "Massively Parallel Single-Nucleus RNA-Seq with DroNc-Seq." Nature Methods, vol. 14, No. 10, pp. 955-958, Aug. 2017.
Picelli, Simone et al.,"Full-length RNA-seq from single cells using Smart-seq2" Nature Protocols, vol. 9, Issue 1, pp. 171-181, 2014.
Dixit et al., "Perturb-Seq: Dissecting Molecular Circuits with Scalable Single-Cell RNA Profiling of Pooled Genetic Screens", Cell, vol. 167, pp. 1853-1866, Dec. 15, 2016.
Adamson et al., "A Multiplexed Single-Cell CRISPR Screening Platform Enables Systematic Dissection of the Unfolded Protein Response", Cell 167, pp. 1867-1882, Dec. 15, 2016.
Konermann, Silvana et al. "Genome-scale transcriptional activation by an engineered CRISPR-Cas9 complex" Nature, vol. 517, pp. 583-588, Jan. 29, 2015.
Qi, L. S., et al., "Repurposing CRISPR as an RNA-guided platform for sequence-specific control of gene expression", Cell, vol. 152, No. 5, pp. 1173-1183, Feb. 28, 2013.
Gilbert, L. A., et al., "CRISPR-mediated modular RNA-guided regulation of transcription in eukaryotes". Cell, vol. 154, No. 2, pp. 442-451, Jul. 18, 2013.
Komor, Alexis et al., "Programmable editing of a target base in genomic DNA without double-stranded DNA cleavage", Nature, vol. 533, pp. 420-424, May 19, 2016.
Nishida, Keiji et al., "Targeted nucleotide editing using hybrid prokaryotic and vertebrate adaptive immune systems", Science, vol. 353, Issue No. 6305, Sep. 16, 2016.
Yang, Luhan al., "Engineering and optimizing deaminase fusions for genome editing", Nature Communication, vol. 7, Issue 13330, Published Nov. 2, 2016.
Hess, Gaelen et al., "Directed evolution using dCas9-targeted somatic hypermutation in mammalian cells", Nature Methods, vol. 13, No. 12, pp. 1036-1042, Dec. 2016.
Ma et al., "Targeted AID-mediated mutagenesis (TAM) enables efficient genomic diversification in mammalian cells", Nature Methods, vol. 13, No. 12, pp. 1029-1035, Dec. 2016.
Ran, F.A., et al., "In vivo genome editing using *Staphylococcus aureus* Cas9", Nature, vol. 520, pp. 186-191, Apr. 9, 2015.
Buenrostro, J. D. et al., "Transposition of native chromatin for fast and sensitive epigenomic profiling of open chromatin, DNA-binding proteins and nucleosome position", Nature Methods, vol. 10, No. 12, pp. 1213-1218, Published online: Oct. 6, 2013.

\* cited by examiner

FIG. 12

4. Sequences and count RNA binding probe sequences
(Sequencing adapters (5' 20bp, 3' 20bp), OB-2 (14bp), Initiator/Spacer (25bp), Gene binding region (25bp), UMI (10bp))

```
SEQUENCE LISTING

<160> NUMBER OF SEQ ID NOS: 21

<210> SEQ ID NO 1
<211> LENGTH: 72
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (72)..(72)
<223> OTHER INFORMATION: 3' C9-dye modification

<400> SEQUENCE: 1
cgtaaaggaa gactcttccc gtttgctgcc ctcctcgcat tctttcttga ggagggcagc      60
aaacgggaag ag                                                         72

<210> SEQ ID NO 2
<211> LENGTH: 72
<212> TYPE: DNA
<213> ORGANISM: Artificial Sequence
<220> FEATURE:
<223> OTHER INFORMATION: Synthetic Oligonucleotide

<400> SEQUENCE: 2
gaggagggca gcaaacggga agagtcttcc tttacgctct tcccgtttgc tgccctcctc      60
aagaaagaat gc                                                         72

<210> SEQ ID NO 3
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 3
cttacggatg ttgcaccagc ctcttcccgt ttgctgccct cctcaagaaa gaatgc          56

<210> SEQ ID NO 4
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 4
cttacggatg ttgcaccagc gctgccctcc tcaagaaaga atgc                       44
```

<210> SEQ ID NO 5
<211> LENGTH: 38
<212> TYPE: DNA
<213> ORGANISM: Artificial Sequence
<220> FEATURE:
<223> OTHER INFORMATION: Synthetic Oligonucleotide

<400> SEQUENCE: 5
cttacggatg ttgcaccagc ctcctcaaga aagaatgc                       38

<210> SEQ ID NO 6
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 6
cttacggatg ttgcaccagc aagaaagaat gc                             32

<210> SEQ ID NO 7
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 7
cttacggatg ttgcaccagc aagaaagaat gcg                            33

<210> SEQ ID NO 8
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 8
cttacggatg ttgcaccagc aagaaagaat gcga                           34

<210> SEQ ID NO 9
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 9
cttacggatg ttgcaccagc aagaaagaat gcgag                          35

<210> SEQ ID NO 10
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 10
gagctttgct aacggtcgag aagaaagaat gcga                           34

<210> SEQ ID NO 11
<211> LENGTH: 18
<212> TYPE: DNA
<213> ORGANISM: Artificial Sequence
<220> FEATURE:
<223> OTHER INFORMATION: Synthetic Oligonucleotide

```
<220> FEATURE:
<221> NAME/KEY: misc_feature
<222> LOCATION: (1)..(1)
<223> OTHER INFORMATION: 5' phosphorylation

<400> SEQUENCE: 11
gaggagggca gcaaacgg                                                        18

<210> SEQ ID NO 12
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 12
ccatgggtgg aatcatattg gaaca                                                25

<210> SEQ ID NO 13
<211> LENGTH: 10
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(10)
<223> OTHER INFORMATION: N = a or g or c or t/u, unknown, or other

<400> SEQUENCE: 13 nnnnnnnnnn                                                                 10

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
ctcgaccgtt agcaaagctc                                                      20

<210> SEQ ID NO 15
<211> LENGTH: 75
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' phosphorylation
<220> FEATURE:
<221> NAME/KEY: misc_feature
<222> LOCATION: (46)..(55)
<223> OTHER INFORMATION: n is a, c, g, or t

<400> SEQUENCE: 15
gaggagggca gcaaacggaa accaggcgcc caatacgacc aaatcnnnnn nnnnnctcga          60
ccgttagcaa agctc                                                           75

<210> SEQ ID NO 16
<211> LENGTH: 16
<212> TYPE: DNA
<213> ORGANISM: Artificial Sequence
<220> FEATURE:
<223> OTHER INFORMATION: Synthetic Oligonucleotide
<220> FEATURE:
```

```
<221> NAME/KEY: misc_feature
<222> LOCATION: (1)..(1)
<223> OTHER INFORMATION: 5' phosphorylation

<400> SEQUENCE: 16
ggagggcagc aaacgg                                                          16

<210> SEQ ID NO 17
<211> LENGTH: 73
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' phosphorylation
<220> FEATURE:
<221> NAME/KEY: misc_feature
<222> LOCATION: (44)..(53)
<223> OTHER INFORMATION: n is a, c, g, or t

<400> SEQUENCE: 17
ggagggcagc aaacggaacc atgggtggaa tcatattgga acannnnnnn nnnctcgacc          60
gttagcaaag ctc                                                             73

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 18
gctggtgcaa catccgtaag                                                      20

<210> SEQ ID NO 19
<211> LENGTH: 73
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' phosphorylation
<220> FEATURE:
<221> NAME/KEY: misc_feature
<222> LOCATION: (44)..(53)
<223> OTHER INFORMATION: n is a, c, g, or t

<400> SEQUENCE: 19
ggagggcagc aaacggaacc atgggtggaa tcatattgga acannnnnnn nnngctggtg          60
caacatccgt aag                                                             73

<210> SEQ ID NO 20
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 20
ttaccagagt taaaagcagc cctgg                                                25

<210> SEQ ID NO 21
<211> LENGTH: 18
```

```
<212> TYPE: DNA
<213> ORGANISM: Artificial Sequence
<220> FEATURE:
<223> OTHER INFORMATION: Synthetic Oligonucleotide

<400> SEQUENCE: 21
gaagagtctt cctttacg                                                  18
```

MULTIMODAL READOUTS FOR QUANTIFYING AND SEQUENCING NUCLEIC ACIDS IN SINGLE CELLS

CROSS-REFERENCE TO RELATED APPLICATIONS

This application claims the benefit of U.S. Provisional Application No. 62/676,069, filed May 24, 2018 and U.S. Provisional Application No. 62/780,889, filed Dec. 17, 2018. The entire contents of the above-identified applications are hereby fully incorporated herein by reference.

STATEMENT REGARDING FEDERALLY SPONSORED RESEARCH

This invention was made with government support under Grant No. HG009749 awarded by the National Institutes of Health. The government has certain rights in the invention.

REFERENCE TO AN ELECTRONIC SEQUENCE LISTING

The contents of the electronic sequence listing (BROD-2450US.ST25.txt"; Size is 5,796 bytes and it was created on May 24, 2019) is herein incorporated by reference in its entirety.

TECHNICAL FIELD

The subject matter disclosed herein is generally directed to methods for high multiplex molecular characterization in single cells.

BACKGROUND

Recent development of methods for single-cell RNA-sequencing (scRNA-seq) have provided the ability to study the RNA expression patterns of individual cells in a heterogeneous population. In combination with CRISPR perturbations, scRNA-seq enables high-content pooled screens that measure the effects of individual perturbations on gene expression in many single cells. However, simultaneous measurement of multiple types of macromolecules (such as that of RNA expression and DNA sequence) in the same cell remains challenging. For example, one class of single cell methods uses microfluidic devices to encapsulate cells in droplets and then performs an enzymatic step to add barcodes to RNA in emulsified droplets. This format poses challenges for multimodal readouts because the molecular biology steps required to read out different types of molecules, require different reagents and buffers, which are difficult to change in emulsified droplets and are typically done through complex "picoinjections".

Thus, there is a need for high-throughput simultaneous measurements of RNA expression, DNA genotype, and other molecular characterizations within single cells.

SUMMARY

In one aspect, the invention provides a method of analyzing nucleic acids, comprising: providing at least one targeting probe to a target nucleic acid, whereby the at least one targeting probe binds to a target region in the target nucleic acid; providing a first sensing oligo, whereby the first sensing oligo binds to the at least one targeting probe; providing a second sensing oligo comprising a sequencing adaptor, whereby the second sensing oligo binds to the first sensing oligo via a hybridization region in the second sensing oligo; and attaching the second sensing oligo to the at least one targeting probe, thereby generating a sequencing construct.

The at least one targeting probe may be a first targeting probe, and the method may further comprise providing a second targeting probe, whereby the first and the second targeting probes bind to first and a second target regions in the target nucleic acid, respectively.

The method may further comprise thermodynamically regulating the binding of the first sensing oligo with the first and the second targeting probes.

The distance between the first and the second target regions may be 10 nt or less. The first or the second target region may be from 10 nt to 200 nt in length. The first and the second targeting probes may bind to a first and a second binding regions in the first sensing oligo, respectively. The first or the second binding region may be from 10 nt to 100 nt in length.

The sequencing construct may comprise at least a portion of the second sensing oligo and at least a portion of the at least one targeting probe.

The method may further comprise obtaining a sequence read of the sequencing construct.

The method may further comprise analyzing the target nucleic acid based, at least in part, on the sequence read of the sequencing construct. Analyzing the target nucleic acid may comprise quantifying the target nucleic acid.

The method may further comprise amplifying the sequencing construct, thereby generating a sequencing library comprising the amplified sequencing construct.

The second sensing oligo may comprise a primer binding site. In some embodiments, the second sensing oligo is attached to the at least one targeting probe by ligation using a ligase.

In some embodiments, the at least one targeting probe comprises a 5' phosphate.

In some embodiments, when attached, the second sending oligo and the at least one targeting probe form a loop structure.

In some embodiments, the at least one targeting probe comprises a sequencing adaptor.

In some embodiments, the at least one targeting probe comprises a primer binding site. In some embodiments, the at least one targeting probe comprises a barcode. The barcode may comprise a unique molecular identifier.

In some embodiments, the hybridization region in the second sensing oligo is less than 10 nt, less than 5 nt, or less than 3 nt in length.

The first or the second sensing oligo may comprise a hairpin structure when not binding to other molecules. The hairpin structure may open when the first or the second sensing oligo binds to the at least one targeting probe, or when the first and the second sensing oligo bind to each other.

In some embodiments, the target nucleic acid is in a cell, and the method further comprises fixing the cell.

In some embodiments, the first and the second sensing oligos may be comprised in the same molecule.

In some embodiments, the target nucleic acid may comprise mRNA or DNA derived therefrom.

In some embodiments, the adaptor in the second sensing probe is at a 3' side of the hybridization region.

In another aspect, the invention provides a system for analyzing nucleic acids, comprising: a) a first targeting probe comprising: i) a first target binding sequence that hybridizes to a first target region in a target nucleic acid sequence, and ii) a first sequencing adaptor; b) an optional second targeting probe comprising a second target binding sequence that hybridizes to a second target region in the target nucleic acid; c) a first sensing oligo comprising: i) a first binding region that hybridizes to the first targeting probe, and ii) an optional second binding region that hybridizes to the second targeting probe; and d) a second sensing oligo comprising: i) a hybridization region that hybridizes to the first sensing oligo, and ii) a second sequencing adaptor.

In some embodiments, the distance between the first and second target regions is 10 nt or less. In some embodiments, the first or the second target region is from 10 nt to 200 nt in length. In some embodiments, the first or the second binding region is from 10 nt to 100 nt in length.

In some embodiments, the second sensing oligo comprises a primer binding site.

In some embodiments, the at least one targeting probe comprises a 5' phosphate.

In some embodiments, the at least one targeting probe comprises a primer binding site. The at least one targeting probe or sensing oligo may comprise a barcode.

In some embodiments, the barcode may comprise a unique molecular identifier.

In some embodiments, the hybridization region in the second sensing oligo is less than 10 nt, less than 5 nt, or less than 3 nt in length.

In some embodiments, the first or the second sensing oligo comprises a hairpin structure when not binding to other molecules. The hairpin structure may open when the first or the second sensing oligo binds to the at least one targeting probe, or when the first and the second sensing oligo bind to each other.

In some embodiments, the adaptor in the second sensing oligo is at a 3' side of the hybridization region.

In some embodiments, the system may further comprise one or more primers configured to bind to at least a portion of the first targeting probe. In some embodiments, the system may further comprise one or more primers configured bind to at least a portion of the second sensing oligo.

In another aspect, the invention comprises a sequencing library comprising sequencing constructs prepared using the methods described herein.

In some embodiments, the oligos may detect nucleic acids inside of cells, and the cells are first crosslinked and permeabilized prior to applying the oligos.

In yet another aspect, the invention provides a method for generating single-cell molecular analysis comprising; a) delivering one or more proximity dependent probes to a cell population, wherein each proximity dependent probe comprises a target binding region configured to bind one or more target RNAs and a primer binding site region; b) linking bound proximity dependent probes; c) using combinatorial split-and-pool strategies, such as ligation, to add sequential barcodes to the linked proximity dependent probes to attach a unique barcode to the set of probes derived from single cells; d) amplifying the ligated probes using the primer pair, wherein the barcode is incorporated into each resulting amplicon; and e) quantifying target RNAs in each individual cell based at least in part on sequencing the resulting amplicons.

In some embodiments, the method may further comprise delivering DNA-tagged protein binding molecules, amplifying the DNA tags to generate sequencing amplicons and quantifying target protein abundance based at least in part on sequencing of amplicons.

In some embodiments, the protein binding molecule is an aptamer or an antibody.

In some embodiments, the bound proximity dependent probes are linked by ligation, splinted ligation, hybridization, or proximity extension.

In some embodiments, the proximity dependent probes are molecular inversion probes (MIPs), HyPR probes, padlock probes, or split-ligation probes, each probe further comprising a unique molecular identifier (UMI).

In some embodiments, the one or more proximity dependent probes target at least 5, at least 10, at least 20, at least 30, at least 40, at least 50, at least 60, at least 70, at least 80, at least 90, at least 100, at least 200, at least 300, at least 500, at least 1000, or at least 10,000 target RNAs.

In some embodiments, multiple proximity dependent probes bind to the same target RNA. In some embodiments, 2 to 100 proximity dependent probes are used per target RNA.

In yet another aspect, the invention provides a method for generating single-cell molecular analysis comprising; a) delivering one or more proximity dependent probes to a cell population, wherein each proximity dependent probe comprises a target binding region configured to bind one or more target RNAs and a primer binding site region; b) linking bound proximity dependent probes; c) isolating single cells from the cell population in separate individual discrete volumes, the individual discrete volumes further comprising a primer pair and amplification reagents, wherein the primer pair binds to the primer binding sites of the proximity dependent probes, and wherein at least one primer comprises a barcode sequence that uniquely identifies the individual discrete volume; d) amplifying the ligated probes using the primer pair, wherein the barcode is incorporated into each resulting amplicon; and e) quantifying target RNAs in each individual cell based at least in part on sequencing the resulting amplicons.

The method may further comprise delivering DNA-tagged protein binding molecules, amplifying the DNA tags to generate sequencing amplicons and quantifying target protein abundance based at least in part on sequencing of amplicons.

In some embodiments, the protein binding molecule is an aptamer or an antibody.

In some embodiments, the bound proximity dependent probes are linked by ligation, splinted ligation, hybridization, or proximity extension.

In some embodiments, the proximity dependent probes are molecular inversion probes (MIPs), HyPR probes, padlock probes, or split-ligation probes, each probe further comprising a unique molecular identifier (UMI).

In some embodiments, the one or more proximity dependent probes target at least 5, at least 10, at least 20, at least 30, at least 40, at least 50, at least 60, at least 70, at least 80, at least 90, at least 100, at least 200, at least 300, at least 500, at least 1000, or at least 10,000 target RNAs.

In some embodiments, multiple proximity dependent probes bind to the same target RNA. In some embodiments, 2 to 100 proximity dependent probes are used per target RNA.

In some embodiments, the individual discrete volumes are droplets.

In some embodiments, at least one primer of the primer pair is delivered to the individual discrete volume on a bead. In some embodiments, the primer is linked to the bead via a cleavable linker.

In some embodiments, single cells are first crosslinked and/or lysed and then isolated in the individual discrete volumes.

In yet another aspect, the invention provides a method for conducting single-cell molecular analysis, comprising: a) encapsulating individual cells in a hydrogel droplet, the hydrogel droplet further optionally comprising one or more primer pairs, wherein each primer in the one or more primer pairs is linked to the hydrogel matrix by a releasable linker, and wherein each primer pair comprises a target binding region for binding one or more target molecules; b) uniquely identifying each hydrogel droplet; c) releasing the one or more primer pairs from the hydrogel matrix via the releasable linker and amplifying the one or more target molecules using the one or more primer pairs thereby generating DNA and/or cDNA amplicons comprising the barcode sequences; and d) identifying and/or quantifying the one or more target molecules based, at least in part, on sequencing of the DNA and/or cDNA amplicons.

In some embodiments, each hydrogel droplet is uniquely identified by barcoding each primer pair via combinatorial indexing. In some embodiments, each hydrogel droplet is uniquely identified by direct barcoding of target molecules comprising ligation of adapters to the target molecules followed by combinatorial indexing of the adapter molecules. In some embodiments, each hydrogel droplet is uniquely identified by re-encapsulating each cell-containing droplet in an individual discrete volume together with a separate particle containing unique adapter molecules.

In some embodiments, each hydrogel droplet further comprises genotyping primer pairs for amplifying one or more genomic loci, at least one primer pair comprising a barcode sequence uniquely identifying each individual discrete volume, and the method further comprising amplifying the one or more genomic loci and genotyping each individual cell by sequencing the resulting amplicons.

The DNA may first be amplified using nonspecific amplification prior to detection of the one or more genomic loci. The DNA may be amplified using whole genome amplification.

In some embodiments, the one or more primer pairs amplify one or more genomic DNA loci of interest to generate DNA amplicons, and wherein the identifying step comprises determining a genotype of each individual cell by sequencing the resulting DNA amplicons.

In some embodiments, the method may further comprise non-specific DNA amplification prior to amplification with the one or more primer pairs, preferably whole-genome amplification (WGA).

In some embodiments, the method may further comprise crosslinking the cells prior to non-specific DNA amplification and before encapsulating them in hydrogels, and reversing the cross-links prior to performing PCR to amplify the genomic DNA loci.

In some embodiments, reverse crosslinking involves heating and treating with a protease.

In some embodiments, the method may further comprise a second PCR amplification to add sequencing adapters to the DNA amplicons.

In some embodiments, a) one of the primers contains a T7 promoter sequence and adds this T7 promoter sequence to the genomic DNA amplicons during PCR; b) T7 in vitro transcription is used to further amplify the DNA amplicons to generate RNA; c) this RNA is reverse transcribed with an appropriate adapter primer to generate cDNA; and d) the cDNA is finally amplified to add sequencing adapters prior to high-throughput sequencing.

In some embodiments, the hydrogel may further comprise oligo-dT primers linked to the hydrogel. The method may further comprise a) suspending the hydrogels in a reverse transcription mixture; b) reverse transcribing RNA to form cDNA; and c) amplifying the resulting cDNA fragments using PCR.

In some embodiments, the hydrogel further comprises one or more DNA proximity dependent probes that comprise a target binding region configured to bind a target DNA and a primer binding site region that bind to the primers of the one or more primer pairs, and wherein the method further comprises; a) generating single stranded DNA molecules; b) binding the proximity dependent probes to corresponding ssDNA target DNA; c) linking bound proximity dependent probes; d) releasing the one or more primer pairs via releasable linkers and amplifying the linked proximity dependent probes to generate proximity dependent probe amplicons; and e) detecting and/or quantifying the one or more target DNAs by sequencing of the generated proximity dependent probe amplicons.

In some embodiments, generating single stranded DNA molecules comprises digesting double stranded DNA with an exonuclease, preferably a Lambda ssDNA exonuclease.

In some embodiments, the method may further comprise non-specific amplification of dsDNA, preferably using whole genome amplification (WGA).

In some embodiments, the proximity dependent probes are linked by ligation, splinted ligation, hybridization, or proximity extension.

In some embodiments, the proximity dependent probes are molecular inversion probes (MIPs), HyPR probes, padlock probes, or split-ligation probes, each probe further comprising a unique molecular identifier (UMI).

In some embodiments, the DNA amplicons are derived from proximity dependent probes that are hybridized to RNA and then linked through ligation.

In some embodiments, the proximity dependent probes are molecular inversion probes (MIPs), HyPR probes, padlock probes, or split-ligation probes.

In some embodiments, each probe optionally further comprises a unique molecular identifier (UMI).

In some embodiments, the proximity dependent probes are amplified by distributing single cells into discrete volumes along with barcoded particles that are loaded at a ratio of 1-20 particles per discrete volume; and after sequencing a computational algorithm is used to infer which particle barcodes came from the same discrete volume and correspond to the same cell by analyzing the UMIs contained in the proximity-dependent probes.

In some embodiments, one or more proximity dependent probes target at least 1, at least 5, at least 10, at least 20, at least 30, at least 40, at least 50, at least 60, at least 70, at least 80, at least 90, at least 100, at least 200, at least 300, at least 500, at least 1000, or at least 10,000 target RNAs.

In some embodiments, multiple proximity dependent probes bind to the same target RNA. In some embodiments, 2 to 100 proximity dependent probes are used per target RNA.

In some embodiments, different numbers of proximity dependent probes are used per target RNA, in order to balance the signal coming from RNAs with different detection efficiencies or abundancies.

In some embodiments, one or more proximity dependent probes target one or more polymorphic sites in target RNAs to provide an allele-specific RNA readout.

In some embodiments, the proximity dependent probes comprise probes with a different 5' nucleotide directly overlapping the polymorphic site such that only a matching probe will be successfully linked.

In some embodiments, the proximity dependent probes are MIPs with hybridization regions flanking the polymorphic region, and wherein each MIP is extended by reverse transcription and then ligated.

In some embodiments, the method may further comprise rolling circle amplification of ligated MIPs to amplify the signal resulting from a successful ligation event.

In some embodiments, the one or more target RNAs comprise one or more lncRNAs.

In some embodiments, the proximity dependent probes are delivered to a population of fixed cells and linked to form a proximity dependent probe complex prior to encapsulating individual fixed cells in the hydrogel droplet.

In some embodiments, the proximity dependent probe complex contains an acrylate or other moiety to enable crosslinking the probe into the hydrogel upon formation of the hydrogel.

In some embodiments, the proximity probes further contain a releasable linker to enable releasing the proximity-dependent probes from the hydrogel prior to PCR amplification.

In some embodiments, proximity dependent probes are applied and linked after encapsulation of cells in the hydrogel. In some embodiments, the proximity dependent probes are applied and linked after encapsulation of cells in the hydrogel and after digestion of other cellular molecules, and wherein the cellular molecules comprise protein or DNA.

In some embodiments, the method may comprise combining measurements of multiple different modalities, including combinatorial split-and-pool strategies, droplet-based methods, DNA amplification, whole transcriptome sequencing, multiplexed DNA detection using MIPs, or any combination thereof.

In some embodiments, the primer pairs for DNA amplification include one or more pairs that binds one or more target genomic loci, and a second primer set comprising primer pairs that bind a primer binding site on proximity dependent probes, and wherein the method comprises: a) binding one or more proximity dependent probes to one or more RNA targets; b) linking the one or more bound proximity dependent probes; c) suspending hydrogels in a PCR amplification mix; d) amplifying the one or more target genomic loci and the one or more proximity dependent probes targeting RNAs to generate barcoded genomic DNA amplicons and barcoded proximity dependent probe amplicons; e) identifying and/or quantifying the type and/or amount of the one or more target RNAs in each individual cell and genotyping each individual cell by sequencing the barcoded proximity dependent probe amplicons and the barcoded genomic DNA amplicons respectively.

In some embodiments, the proximity dependent probes are delivered to a population of fixed cells and linked prior to encapsulating individual fixed cells in the hydrogel droplet.

In some embodiments, the primer pairs for DNA amplification include one or more pairs that binds one or more target genomic loci, and a second primer set comprising primer pairs that bind a primer binding site on proximity dependent probes, and wherein the method comprises: a) crosslinking and permeabilizing cells; b) binding one or more proximity dependent probes to one or more RNA targets; c) linking the one or more bound proximity dependent probes; d) suspending hydrogels in a PCR amplification mix; e) reversing crosslinks, such as by heating and applying a protease; f) amplifying the one or more target genomic loci and the one or more proximity dependent probes targeting RNAs to generate barcoded genomic DNA amplicons and barcoded proximity dependent probe amplicons; g) optionally performing further amplification steps, such as a second PCR or T7 in vitro transcription; and h) identifying and/or quantifying the type and/or amount of the one or more target RNAs in each individual cell and genotyping each individual cell by sequencing the barcoded proximity dependent probe amplicons and the barcoded genomic DNA amplicons respectively.

In some embodiments, a chained primer strategy is used, and wherein, for each genomic DNA target, a single primer pair is used containing appropriate adapters that can then be amplified by a second primer or primer pair containing cell barcodes, and where that same second primer or primer pair can simultaneously amplify the proximity-dependent probes.

In some embodiments, the hydrogel further comprises oligo-dT primers linked to the hydrogel via a first releasable linker and one or more primer pairs linked to the hydrogel via second releasable linker, and wherein the method further comprises; a) suspending the hydrogels in a reverse transcription mixture; b) releasing the barcoded oligo-dT primers via the first releasable linker and reverse transcribing RNA to form cDNA; c) eluting the cDNA from the hydrogels for amplification to generate cDNA amplicons; d) re-suspending the hydrogels in a PCR amplification mixture; e) releasing the one or more primer pairs from the hydrogel matrix via the second releasable linker and amplifying the one or more genomic DNA loci of interest using the one or more primer pairs to generate barcoded DNA amplicons; and f) quantifying RNA expression in each individual by sequencing of barcoded cDNA amplicons and genotyping each individual cell by sequencing of barcoded DNA amplicons.

In some embodiments, the method may further comprise applying oligonucleotide-tagged protein binding molecules before or after encapsulating cells in hydrogels, amplifying the oligonucleotide tag using one or primer pairs to generate barcoded oligonucleotide tag amplicons, identifying and/or quantitating target protein abundance based at least in part on sequencing the barcoded oligonucleotide tag amplicons.

In some embodiments, the method may further comprise suspending the hydrogels in an additional molecular assay mixture and conducting one or more additional molecular assays. In some embodiments, the one or more additional assays is a chromatin accessibility assay. In some embodiments, the chromatin accessibility assay is ATAC-seq.

In some embodiments, the one or more additional assays is an epigenetic modification assay.

In some embodiments, the one or more additional assays is a chromatin folding assay. In some embodiments, the chromatin folding assay is Hi-C or Hi-C++.

In some embodiments, the hydrogel further comprises a nucleic acid binding molecule, a protein binding molecule, or both for cross-linking nucleic acids and/or proteins to the hydrogel matrix. In some embodiments, the nucleic acid binding molecule is LabelX and the protein binding molecule is an amine reactive acrylate or acrylamide moiety, such as AcX.

In some embodiments, the individual cells are fixed prior to encapsulating in the hydrogel droplet. In some embodiments, the crosslinks are reversed in the fixed cells after encapsulating them in hydrogels.

In some embodiments, the hydrogel comprises acrylamide/bisacrylamide, acrylamide/di-hydroxyethylenebisacrylamide, or acrylamide/N,N'-bis(acryloyl)cystamine. In some embodiments, the ratio of acrylamide to bisacrylamide ranges from 10:1 to 40:1. In some embodiments, the percentage of acrylamide/bisacrylamide ranges from 3% to 20%.

In some embodiments, the cells to be assayed are first exposed to one or more perturbations. In some embodiments, the one or more perturbation comprises exposure to one or more physical perturbations, genetic perturbations, chemical perturbations, or a combination thereof. In some embodiments, the one or more physical perturbations comprises exposure to different temperatures, pressures, flow rates, pHs, growth media compositions, or gas concentrations. In some embodiments, the one or more genetic perturbations comprises gene knock-outs, gene knock-ins, transpositions, inversions, and/or one or more nucleotide insertions, deletions, or substitutions. In some embodiments, the one or more chemical perturbations comprises exposure to one or more therapeutic agents or a concentration range of therapeutic agents. In some embodiments, two or more perturbations are done sequentially and an additional round of combinatorial indexing is done between each perturbation round.

In some embodiments, one or more proximity dependent probes and/or oligonucleotide-tagged protein binding molecules are configured to detect one or more gene expression products in one or more cell pathways. In some embodiments, the one or more cell pathways comprise a cell development pathway, a cancer signaling pathway, or an immune response signaling pathway.

In yet another aspect, the invention provides a molecular assay system comprising; a) a set of proximity dependent probes; and b) a set of primer pairs, wherein each primer pair comprises at least one barcoded primer.

In some embodiments, the proximity dependent probes are molecular inversion probes (MIPs), HyPR probes, padlock probes, or split-ligation probes, each probe further comprising a unique molecular identifier (UMI).

In some embodiments, the set of proximity dependent probes comprise proximity dependent probes for detecting and/or quantitating at least 5, at least 10, at least 20, at least 30, at least 40, at least 50, at least 60, at least 70, at least 80, at least 90, at least 100, at least 200, at least 300, at least 500, at least 1000, or at least 10,000 target RNAs. In some embodiments, 2 to 100 proximity dependent probes are used per target RNA.

In some embodiments, the set of proximity dependent probes detect gene expression markers on one or more cell signaling pathways. In some embodiments, the one or more cell signaling pathways comprises a cell development pathway, a cancer signaling pathway, or an immune response signaling pathway.

In some embodiments, the primer pairs amplify one or more genomic DNA loci and allow for genotyping in combination with targeted RNA detection and quantitation. In some embodiments, the targeted genomic DNA loci include sites of somatic mutations that affect known processes such as proliferation or cancer development.

In some embodiments, the individual discrete volumes are droplets, wherein the system further comprises reagents for droplet formation.

In some embodiments, the system further comprises a means for sorting and or encapsulating individual cells into droplets. The means for sorting and/or encapsulating individual cells may comprise a microfluidic device.

In some embodiments, the system may further comprise reagents for PCR amplification.

In some embodiments, one or both barcoded primers comprise a set of discrete beads, wherein each bead contains a unique barcode. The discrete bead may comprise hydrogel beads, magnetic beads, or other beads.

In some embodiments, the discrete beads may be distributed randomly amongst the droplets together with cells so that each droplet has ~1 cell and ~1 bead with barcodes.

In yet another aspect, the invention provides a molecular assay system comprising droplet forming reagents for formation of hydrogel based droplets that contain cells and/or primers with linkers that link the primer pairs to the hydrogel matrix upon droplet formation.

In some embodiments, the droplet forming reagents further comprise a linker molecule for linking nucleic acids to the hydrogel and/or a linker molecule for linking proteins to the hydrogel and/or primers with releasable linkers that link amplification primers to the hydrogel matrix upon droplet formation.

In some embodiments, the nucleic acid linking molecule is LabelX and the protein linking molecule is AcX.

In some embodiments, the system may further comprise oligo-dT RT primers comprising a releasable linker that links the oligo-dT RT primers to the hydrogel.

In some embodiments, the system may further comprise a set of proximity dependent probes. The proximity dependent probes may be molecular inversion probes (MIPs), HyPR probes, padlock probes, or split-ligation probes, each probe further comprising a unique molecular identifier (UMI).

In some embodiments, the set of proximity dependent probes comprise proximity dependent probes for detecting and/or quantitating at least 1, at least 5, at least 10, at least 20, at least 30, at least 40, at least 50, at least 60, at least 70, at least 80, at least 90, at least 100, at least 200, at least 300, at least 500, at least 1000, or at least 10,000 target RNAs or DNAs.

In some embodiments, 10 to 100 proximity dependent probes are used per target RNA and/or DNA.

In some embodiments, the system may further comprise one or more oligonucleotide tagged protein binding molecules, wherein the oligonucleotide on the oligonucleotide tagged protein binding molecules comprises a primer binding set for the primer pairs or a portion of the primer pairs.

In some embodiments, the set of proximity dependent probes and/or oligonucleotide tagged protein binding molecules detect gene expression markers of one or more cell signaling pathways. The one or more cell signaling pathways may comprise a cell development pathway, a cancer signaling pathway, or an immune response signaling pathway.

In some embodiments, the system may further comprise fixing reagents to fix cells prior to encapsulation in hydrogel droplets. The system may further comprise cross-linking reversing agents to reverse cross-links formed in fixed cells.

In some embodiments, the system may further comprise combinatorial indexing reagents for adding barcode sequences to the one or more primer pairs linked to the hydrogel matrix.

In some embodiments, the system may further comprise barcoding adapters and reagents for ligating the barcoding adapters to target molecules to allow for direct barcoding of target molecules.

In some embodiments, the system may further comprise an exonuclease for converting dsDNA into ssDNA.

In some embodiments, the system may further comprise whole genome amplification regents, PCR amplification reagent, reverse transcription reagents, rolling circle amplification reagents, or a combination thereof.

In some embodiments, the system may further comprise a means for sorting and/or encapsulating individual cells in hydrogel droplets. In some embodiments, the means for sorting and/or encapsulating individual cells in hydrogel droplets comprises a microfluidic device.

In some embodiments, the droplet reagents may comprise acrylamide/bisacrylamide, acrylamide/di-hydroxyethylenebisacrylamide, or acrylamide/N,N'-bis(acryloyl)cystamine. In embodiments, the ratio of acrylamide to bisacrylamide may range from 10:1 to 40:1. The percentage of acrylamide/bisacrylamide may range from 3% to 20%.

In some embodiments, the system may further comprise barcoded beads, wherein the barcoded beads comprise sets of primers that can be co-emulsified with the cell-containing hydrogels.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 12—shows designs of example sensing oligos in an adapted HCR system.

Figure 1:
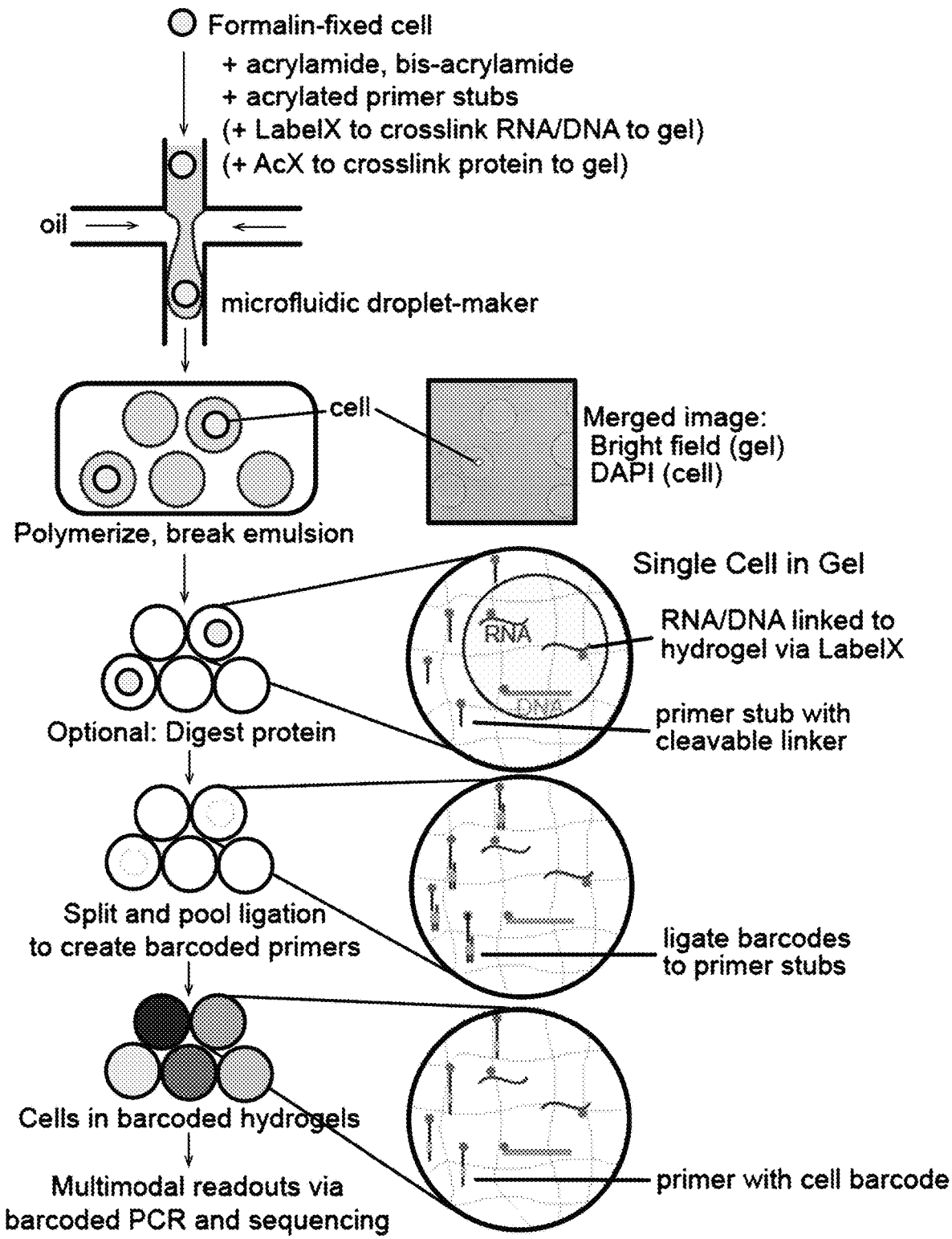
FIG. 1—shows a schematic of the Cell-in-Gel approach showing hydrogel encapsulation of single cells and contents, followed by split-pool barcoding of hydrogel droplets and subsequent readout via high throughput sequencing methods.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

The term "barcode" or "barcode handle sequence" as used herein, refers to any unique, non-naturally occurring, nucleic acid sequence that may be used to identify the originating source of a nucleic acid fragment. Such barcodes may be sequences including but not limited to, TTGAGCCT, AGTTGCTT, CCAGTTAG, ACCAACTG, GTATAACA or CAGGAGCC. Although it is not necessary to understand the mechanism of an invention, it is believed that the barcode sequence provides a high-quality individual read of a barcode associated with a viral vector, labeling ligand, shRNA, sgRNA or cDNA such that multiple species can be sequenced together.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Reference is made to International Patent numbers PCT/US16/059233, filed Oct. 27, 2016, PCT/US2016/059195, filed Oct. 27, 2016, and PCT/US16/059230 filed Oct. 27, 2016.

All publications, published patent documents, and patent applications cited herein are hereby incorporated by reference to the same extent as though each individual publication, published patent document, or patent application was specifically and individually indicated as being incorporated by reference.

Overview

In one aspect, embodiments disclosed herein provide compositions, systems and methods for performing multiple molecular assays in single cells. In certain embodiments, embodiments disclosed herein may allow for quantification of one or more selected RNA fragments, quantification of specific RNA exons or detecting RNA sequence variants, quantifying protein abundance, determination of DNA sequence (including genotyping), DNA accessibility and other molecular assays.

In another aspect, embodiments disclosed herein provide compositions, systems, and methods for single cell encapsulation methods that allow for sequential enzymatic reactions. Simultaneous measurement of multiple types of macromolecules (e.g. RNA and DNA) in the same cell can be challenging. For example, one class of single-cell methods uses microfluidic devices to encapsulate cells in droplets and then performs an enzymatic step to add barcodes to RNA in emulsified droplets. This format poses challenges for multimodal readouts because the molecule biology steps required to read out different types of molecules require different reagents and buffers, which are difficult to change in emulsified droplets and are typically done through complex "picoinjections."

Provided herein are methods for providing multi-modal readouts in single cells, i.e. quantifying specific RNAs, determining DNA sequence, and/or quantifying protein abundance from the same single cells.

In another aspect, the present disclosure provides methods and systems for robust, sensitive, and high-throughput targeted measurements of RNA expression in millions of single cells. In some embodiments, the methods herein combine hybridization of DNA probes with a high throughput sequencing readout for digital expression quantification. The flexible probe design strategy allows for detection about 200 or more chosen transcripts including mRNAs, non-polyadenylated transcripts, and synthetic RNA barcodes, and provides higher detection efficiency (e.g., compared to droplet-based single-cell transcriptomics). For example, the methods and systems may be used for quantifying targeted changes in RNA expression to enable large-scale CRISPR screens, characterization of noncoding genetic variants, and single-cell diagnostics.

In some examples, the methods may include: binding a targeting probe to a target nucleic acid; binding a first sensing oligo to the targeting probe; binding a second sensing oligo to the first sensing oligo, which brings the second sensing oligo close to the targeting probe; ligating the second sensing oligo and the targeting probe to form a sequencing construct. The sequencing construct may be sequenced and the reads may be used for analyzing the target RNA. In some cases, two targeting probes may be used. Such two targeting probes may bind to adjacent target regions in the target nucleic acid.

METHODS AND SYSTEMS FOR ANALYZING NUCLEIC ACIDS

In an aspect, the present disclosure provides methods of analyzing nucleic acids, comprising providing at least one targeting probe to a target nucleic acid, wherein the targeting probe binds to a target region in the target nucleic acid. One may also provide a first sensing oligo, whereby the first sensing oligo binds to the at least one targeting probe. One may also provide a second sensing oligo comprising a sequencing adaptor, whereby the second sensing oligo binds to the first sensing oligo via a hybridization region in the second sensing oligo. One may then attach the second sensing oligo to the at least one targeting probe, thereby generating a sequencing construct.

In another aspect, the present disclosure provides systems for analyzing nucleic acids, comprising a) a first targeting probe; b) an optional second targeting probe comprising a second target binding sequence that hybridizes to a second target region in the target nucleic acid; c) a first sensing oligo; and d) a second sensing oligo. The first targeting probe may comprise i) a first target binding sequence that hybridizes to a first target region in a target nucleic acid sequence, and ii) a first sequencing adaptor. The first sensing oligo may comprise i) a first binding region that hybridizes to the first targeting probe, and ii) an optional second binding region that hybridizes to the second targeting probe. The second sensing oligo may comprise i) a hybridization region that hybridizes to the first sensing oligo, and ii) a second sequencing adaptor.

Targeting Probes

The systems may comprise one or more targeting probes. A targeting probe may be an oligonucleotide, e.g., DNA, RNA, or a hybrid thereof, that is capable of binding to a target nucleic acid. The targeting probe may be single stranded or double stranded. In some cases, the targeting probe may comprise a hairpin structure. In some examples, the targeting probe may be DNA, e.g., single stranded DNA.

The targeting probe may comprise a region for binding to a target nucleic acid. The region may be substantially complementary to a target region in the target nucleic acid. In some cases, the region is completely complementary to a target region. In some cases, the region may be at least 50%, at least 60%, at least 70%, at least 80%, at least 90%, at least 95%, or at least 99% complementary to a target region. In some cases, the targeting probe may further comprise a region for binding to a sensing oligo as described herein.

The target region in a target nucleic acid that can be bound by a targeting probe may be from about 5 nucleotides (nt) to about 500 nt, from about 10 nt to about 300 nt, from about 10 nt to about 200 nt, from about 10 nt to about 100 nt, from about 10 nt to about 50 nt, from about 10 nt to about 40 nt, from about 15 nt to about 35 nt, from about 10 nt to about 20 nt, from about 15 nt to about 25 nt, from about 20 nt to about 30 nt, from about 25 nt to about 35 nt, from about 30 nt to about 40 nt, from about 35 nt to about 45 nt, or from about 40 nt to about 50 nt in length. For example, the targeting region may be about 5, about 10, about 15, about 16, about 17, about 18, about 19, about 20, about 21, about 22, about 23, about 24, about 25, about 26, about 27, about 28, about 29, about 30, about 35, about 40, about 50, about 60, about 70, about 80, about 90, or about 100 nt in length. In some examples, the target region is from about 10 to about 200 nt in length. In some examples, the target region is about 25 nt in length.

In some cases, the systems may comprise one targeting probe, e.g., only one targeting probe. In certain cases, the systems may comprise a plurality of targeting probes, e.g., 2, 3, 4, 5 6 or more. In some examples, the systems comprise 2 targeting probes. In cases where the systems comprise a plurality of targeting probes, the targeting probes may bind to the same target nucleic acid. For example, the targeting probes may bind to target regions adjacent to each other on a target nucleic acid.

In some embodiments, a targeting probe may comprise one or more modifications. For example, the targeting probe may comprise a phosphate. The phosphate may be on the 5' end of the targeting probe. Alternatively or additionally, the phosphate may be on the 3' end of the targeting probe. In some cases, the phosphate may facilitate ligation of the targeting probes to another molecule, e.g., a sensing oligo.

Sensing Oligos

The systems may comprise one or more sensing oligos. A sensing oligo may be an oligonucleotide, e.g., DNA, RNA, or a hybrid thereof, that bind to one or more targeting probes described herein. The sensing oligo may be single stranded or double stranded. In some cases, the sensing oligo may comprise a hairpin structure. In some examples, the sensing oligo may be DNA, e.g., single stranded DNA.

The sensing oligo may comprise one or more binding regions for binding with one or more targeting probes. In some embodiments, a sensing oligo binds to multiple targeting probes. In such cases, the sensing oligo may comprise multiple binding regions, each binding region binding to a targeting probe.

The binding region of a sensing oligo may be substantially complementary to sequence in a targeting probe. In some cases, the region is completely complementary to a sequence in a targeting probe. In some cases, the binding region may be at least 50%, at least 60%, at least 70%, at least 80%, at least 90%, at least 95%, or at least 99% complementary to a sequence in a targeting probe.

A sensing oligo's binding region that binds to a targeting probe may be from about 5 nt to about 500 nt, from about 10 nt to about 300 nt, from about 10 nt to about 200 nt, from about 10 nt to about 100 nt, from about 10 nt to about 50 nt, from about 10 nt to about 40 nt, from about 15 nt to about 35 nt, from about 10 nt to about 20 nt, from about 15 nt to about 25 nt, from about 20 nt to about 30 nt, from about 25 nt to about 35 nt, from about 30 nt to about 40 nt, from about 35 nt to about 45 nt, or from about 40 nt to about 50 nt in length. For example, the binding region may be about 5, about 10, about 15, about 16, about 17, about 18, about 19, about 20, about 21, about 22, about 23, about 24, about 25, about 26, about 27, about 28, about 29, about 30, about 35, about 40, about 50, about 60, about 70, about 80, about 90, or about 100 nt in length. In some examples, the binding region is from about 10 to about 100 nt in length.

In some cases, the systems comprise one sensing oligo, e.g., only one sensing oligo. In certain cases, the systems comprise a plurality of, e.g., 2, 3, 4, 5 6 or more, sensing oligos. In some examples, the systems may comprise 2 sensing oligos. In cases where the systems comprise a plurality of sensing oligos, the sensing oligos may bind to each other.

A sensing oligo may bind to another sensing oligo via a hybridization region. The hybridization region may be 20 nt or less, 18 nt or less, 16 nt or less, 14 nt or less, 12 nt or less, 10 nt or less, 8 nt or less, 6 nt or less, 4 nt or less, 2 nt or less, or 1 nt or less in length. In some examples, a sensing oligo may have a hybridization region that is 10 nt or less in length. In some cases, the hybridization region may be 1, 2, 3, 4, 5, 6, 7, 8, 9, or 10 nt in length. In one example, the hybridization region may be 2 nt in length. In one example, the hybridization region may be 3 nt in length. In some examples, however, a sensing oligo does not have any hybridization region that binds to another sensing oligo.

Binding of Targeting Probe and Target Nucleic Acid

The methods may include providing one or more targeting probes so that the targeting probe(s) binds to a target nucleic acid. In some cases, the target nucleic acid may be DNA, such as genomic DNA, DNA in organelles (e.g., mitochondrial DNA or chloroplast DNA), cell-free DNA, cDNA, synthetic DNA, or any combination thereof. In certain cases, the target nucleic acid may be RNA, such as mRNA, tRNA, rRNA, microRNA, cell-free RNA, non-polyadenylated transcripts, and synthetic RNA. In certain cases, the target nucleic acid may comprise a hybrid of DNA and RNA. In some examples, the target nucleic acid is RNA. In some embodiments, the target nucleic acid comprises mRNA or DNA derived therefrom.

When binding to the targeting probe(s), the target nucleic acid may be in a nucleus, e.g., inside a cell or outside a cell. In some cases, the target nucleic acid may be outside a nucleus when binding to the targeting probe(s). When the target nucleic acid is in a cell or nucleus, the cell or nucleus may be fixed, e.g., using methods described herein.

The method may include providing multiple targeting probes so the multiple targeting probes bind to multiple target regions in the target nucleic acid. For example, the methods may comprise providing a first and a second targeting probes, which bind to a first and a second target regions in the target nucleic acid, respectively.

In some cases, the first and the second target regions may be adjacent to each other. For example, the first and the second target regions may have a distance that is 50 nt or less, 40 nt or less, 30 nt or less, 20 nt or less, 10 nt or less, 9 nt or less, 8 nt or less, 7 nt or less, 6 nt or less, 5 nt or less, 4 nt or less, 3 nt or less, 2 nt or less, or 1 nt or less. In some cases, the first and the second target regions have a distance that is 1 nt, 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, or 20 nt. In some example, the first and the second target regions have a distance of 2 nt.

In certain embodiments, the at least one targeting probe is a first targeting probe, and the method may further comprise providing a second targeting probe, whereby the first and the second targeting probes bind to first and a second target regions in the target nucleic acid, respectively.

The target region in a target nucleic acid that can be bound by a targeting probe may be from about 5 nucleotides (nt) to about 500 nt, from about 10 nt to about 300 nt, from about 10 nt to about 200 nt, from about 10 nt to about 100 nt, from about 10 nt to about 50 nt, from about 10 nt to about 40 nt, from about 15 nt to about 35 nt, from about 10 nt to about 20 nt, from about 15 nt to about 25 nt, from about 20 nt to about 30 nt, from about 25 nt to about 35 nt, from about 30 nt to about 40 nt, from about 35 nt to about 45 nt, or from about 40 nt to about 50 nt in length. For example, the targeting region may be about 5, about 10, about 15, about 16, about 17, about 18, about 19, about 20, about 21, about 22, about 23, about 24, about 25, about 26, about 27, about 28, about 29, about 30, about 35, about 40, about 50, about 60, about 70, about 80, about 90, or about 100 nt in length. In some examples, the target region is from about 10 to about 200 nt in length. In some examples, the target region is about 25 nt in length.

In some embodiments, the target nucleic acid may be in a cell. In some embodiments, the method may further comprise fixing or crosslinking the cell, as described elsewhere herein. In some embodiments, the oligos detect nucleic acids inside of cells, and the cells are first crosslinked and permeabilized prior to applying the oligos.

In some embodiments, the targeting probe may comprise a 5' phosphate.

Binding of Sensing Oligo with Targeting Probe and Another Sensing Oligo

The method may include providing one or more sensing oligos so that the sensing oligo(s) binds to one or more targeting probes. In some cases, the method includes providing a sensing oligo so that that it binds to at least one, e.g., 1, 2, 3, 4, 5, 6, or more targeting probes. In some examples, the sensing oligo binds to one targeting probe. In some examples, the sensing oligo binds to two targeting probes.

In some examples, the sensing oligo binds to a first and a second targeting probes. In such cases, the first and the second targeting probes bind to a first and a second binding regions in the first sensing oligo, respectively.

In some cases, the first and the second binding target regions may be adjacent to each other. For example, the first and the second binding target regions may have a distance that is 50 nt or less, 40 nt or less, 30 nt or less, 20 nt or less, 10 nt or less, 9 nt or less, 8 nt or less, 7 nt or less, 6 nt or less, 5 nt or less, 4 nt or less, 3 nt or less, 2 nt or less, or 1 nt or less. In some cases, first and the second target regions have a distance that is 1 nt, 2 nt, 3 nt, 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, or 20 nt. In some example, the first and the second binding regions has a distance of 2 nt. The second sensing oligo may bind to the first oligo via a hybridization region on the second sensing oligo, which may be less than 10 nt, less than 5 nt or less than 3 nt in length.

The binding of the sensing oligo with the targeting probe(s) may be regulated. In some cases, the binding may be thermodynamically regulated. For example, the binding may be regulated by incubating the reaction at certain temperature.

In some embodiments, the methods include providing multiple sensing oligos, including a first and a second sensing oligos. The first sensing oligo may bind to the targeting probe(s) as described above. The second sensing oligo may bind to the first oligo via a hybridization region on the second sensing oligo.

In certain embodiments, the first and second targeting probes may bind to first and second binding regions in the first sensing oligo, respectively. In specific embodiments, the first or the second binding region may be from 10 nt to 100 nt in length, as described elsewhere herein.

Hairpin Structure and Initiator

A sensing oligo may comprise a hairpin structure, e.g., when not binding to other molecules. The hairpin structure may open when the sensing oligo binds to another molecule, such as a targeting probe or another sensing oligo.

In some cases, the hairpin structure in the sensing oligo may comprise one or more secondary structure units, e.g., one or more loops. the secondary structures may prevent the sensing oligo from binding to another molecule. The secondary structures may be metastable under the reaction conditions in the absence of an initiator nucleic acid. In the presence of an initiator, the secondary structures may change such that the sensing oligo may hybridize to another molecule such as a targeting probe and/or another sensing oligo.

The secondary structure in a sensing oligo may open when it binds to an initiator. The initiator may be a nucleic acid molecule that comprises a region substantially complementary to a portion of the sensing oligo. In some cases, the initiator may be a targeting probe. In certain cases, the initiator may be a sensing oligo.

In other embodiments, the initiator comprises at least a portion of a nucleic acid that is part of a "initiation trigger" such that the initiator is made available when a predetermined physical event occurs. The predetermined event may be the presence of an analyte of interest. In certain embodiments, the predetermined event may be any physical process that exposes the initiator. For example, and without limitation, the initiator may be exposed as a result of a change in temperature, pH, the magnetic field, or conductivity. In each of these embodiments the initiator may be associated with a molecule that is responsive to the physical process. Thus, the initiator and the associated molecule together form the initiation trigger. For example, the initiator may be associated with a molecule that undergoes a conformational change in response to the physical process. The conformational change may expose the. In other embodiments, however, the initiation trigger comprises a single nucleic acid. The initiator region of the nucleic acid is made available in response to a physical change. For example, the conformation of the initiation trigger may change in response to pH to expose the initiator region.

The structure of the trigger may be such that when the analyte of interest is not present (or the other physical event has not occurred), the initiator is not available to hybridize with the sticky end of a monomer. Analyte frees the initiator such that it can interact with a metastable monomer. In some embodiments, analyte causes a conformational change in the trigger that allows the initiator to interact with the sensing oligo.

The initiator may be part of a trigger comprising a nucleic acid that is linked to or associated with a recognition molecule, such as an aptamer, that is capable of interacting with an analyte of interest. The trigger may be designed such that when the analyte of interest interacts with the recognition molecule, the initiator is able to stimulate HCR. Preferably, the recognition molecule is one that is capable of binding the analyte of interest. Recognition molecules include, without limitation, polypeptides, such as antibodies and antibody fragments, nucleic acids, such as aptamers, and small molecules. The use of an initiator bound to an aptamer is described in more detail below.

Sensing oligos with hairpin structures and initiators may include those described in US20180010166A1 and U.S. Pat. No. 7,632,641B2.

In some embodiments, when attached, the second sensing oligo and the at least one targeting probe may form a loop structure. In some embodiments, the first or the second sensing oligo may comprise a hairpin structure when not binding to other molecules. The hairpin structure may open when the first or the second sensing oligo binds to the at least one targeting probe, or when the first and the second sensing oligo bind to each other.

In some embodiments, the first and the second sensing oligos may be comprised in the same molecule.

In some embodiments, the targeting probe or sensing oligo may comprise a barcode as described elsewhere herein.

Ligation

In such cases, the methods may further comprise attaching the second sensing oligo to a targeting probe. The construct resulting from the attachment may be a sequencing construct as described herein. The attachment may be performed by ligation. In some cases, the method may further include modifying (e.g., adding a phosphate to the 5' end) the second sensing oligo and/or the targeting probe to facilitate ligation. In some embodiments, the second sensing oligo may comprise a primer binding site. In some embodiments, the second sensing oligo may be attached to the at least one targeting probe by ligation using a ligase as described herein.

As used herein, the term "ligation" refers to joining two or more nucleic acid molecules. The ligation may be performed using a ligase. A ligase may refer to an enzyme that is capable of ligating nucleic acid. For example, a ligase may be capable of ligating the 3'-end of an acceptor polynucleotide to a the 5'-end of a donor polynucleotide. Examples of ligases include bacteriophage T4 DNA ligase, *Escherichia coli* (*E. coli*) DNA ligase, *Aquifex aeolicus* DNA ligase, *Thermus aquaticus*(Taq) DNA ligase, 9° N™ DNA ligase, *Methanobacterium thermoautotrophicum* RNA ligase, *Ferroplasma acidiphilum* DNA ligase, Human DNA ligase I, Human DNA ligase II, Human DNA ligase III, Human DNA ligase IV, Vaccinia virus DNA ligase, *Chlorella* virus DNA ligase, *Pyrococcus furiosis* DNA ligase, *Haloferax volcanii* DNA ligase, *Acidianus ambivalens* DNA ligase, *Archaeoglobus fulgidus* DNA ligase, *Aeropyrum pernix* DNA ligase, *Cenarcheon symbiosum* DNA ligase, *Haloarcula marismortui* DNA ligase, *Ferroplasma acidarmanus* DNA ligase, *Natronomonas pharaonis* DNA ligase, *Haloquadratum walsbyi* DNA ligase, *Halobacterium salinarum* DNA ligase, *Methanosarcina acetivorans* DNA ligase, *Methanosarcina barkeri* DNA ligase, *Methanococcoides burtonii* DNA ligase, *Methanospirillum hungatei* DNA ligase, *Methanocaldococcus jannaschii* DNA ligase, *Methanopyrus kandleri* DNA ligase, *Methanosarcina mazei* DNA ligase, *Methanococcus maripaludis* DNA ligase, *Methanosaeta thermophile* DNA ligase, *Methanosphaera stadtmanae* DNA ligase, *Methanothermobacter thermautotrophicus* DNA ligase, *Nanoarchaeum equitans* DNA ligase, *Pyrococcus abyssi* DNA ligase, *Pyrobaculum aerophilum* DNA ligase, *Pyrococcus horikoshii* DNA ligase, *Picrophilus torridus* DNA ligase, *Sulfolobus acidocaldarius* DNA ligase, *Sulfolobus shibatae* DNA ligase, *Sulfolobus solfataricus* DNA ligase, *Sulfolobus tokodaii* DNA ligase, *Thermoplasma acidophilum* DNA ligase, *Thermococcus fumicolans* DNA ligase, *Thermococcus kodakarensis* DNA ligase, *Thermococcus* sp. NA1 DNA ligase, *Thermoplasma volcanium* DNA ligase, *Staphylococcus aureus* DNA ligase, *Thermus scotoductus* NAD+-DNA ligase, T4 RNA ligase, *Staphylococcus aureus* DNA ligase, *Methanobacterium thermoautotrophicum* DNA ligase, *Thermus* species AK16D DNA ligase, *Haemophilus influenzae* DNA ligase, *Thermus thermophilus* DNA ligase, bacteriophage T7 DNA ligase, *Haemophilus influenzae* DNA ligase, *Mycobacterium tuberculosis* DNA ligase, *Deinococcus radiodurans* RNA ligase, *Methanobacterium thermoautotrophicum* RNA ligase, *Rhodothermus marinus* RNA ligase, *Trypanosoma brucei* RNA ligase, bacteriophage T4 RNA ligase 1, Ampligase, and bacteriophage T4 RNA ligase 2. In some examples, the ligase may be T4 ligase. In some examples, the ligase may be T7 ligase.

Amplification

In some embodiments, the sequencing constructs generated herein may be amplified. The amplification may be performed using amplification primers. The primers may bind to primer binding site(s), adaptor(s), and/or barcode(s) on the sequencing construct.

The amplification may be performed using methods described herein. Examples of amplification techniques that can be used include, but are not limited to, PCR, quantitative PCR, quantitative fluorescent PCR (QF-PCR), multiplex fluorescent PCR (MF-PCR), real time PCR, reverse transcription PCR (RT-PCR), single cell PCR, restriction fragment length polymorphism PCR (PCR-RFLP), hot start PCR, nested PCR, in situ polony PCR, in situ rolling circle amplification (RCA), bridge PCR, picotiter PCR, and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR), and nucleic acid sequence-based amplification (NASBA).

In some embodiments, the systems and methods described herein may comprise one or more primers configured to bind to at least a portion of the first targeting probe. In some embodiments, the systems and methods described herein may comprise one or more primers configured to bind to at least a portion of the second sensing oligo.

Sequencing

The methods herein may further include sequencing one or more of the sequencing constructs (and/or amplicons thereof), or a portion thereof. In some embodiments, the sequencing construct may comprise at least a portion of the second sensing oligo and at least a portion of the at least one targeting probe, as described herein.

In some cases, the sequencing may be next generation sequencing. The terms "next-generation sequencing" or "high-throughput sequencing" refer to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies or single-molecule fluorescence-based method commercialized by Pacific Biosciences. Any method of sequencing known in the art can be used before and after isolation. In certain embodiments, a sequencing library is generated and sequenced.

At least a part of the sequencing constructs generated by the methods herein may be sequenced to produce a plurality of sequence reads. The fragments may be sequenced using any convenient method. For example, the fragments may be sequenced using Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure et al (Science 2005 309: 1728-32); Imelfort et al (Brief Bioinform. 2009 10:609-18); Fox et al (Methods Mol Biol. 2009; 553:79-108); Appleby et al (Methods Mol Biol. 2009; 513:19-39) and Morozova et al (Genomics. 2008 92:255-64), which are incorporated by reference for the general descriptions of the methods and the particular steps of the methods, including all starting products, methods for library preparation, reagents, and final products for each of the steps. As would be apparent, forward and reverse sequencing primer sites that are compatible with a selected next generation sequencing platform can be added to the ends of the fragments during the amplification step. In certain embodiments, the fragments may be amplified using PCR primers that hybridize to the tags that have been added to the fragments, where the primer used for PCR have 5' tails that are compatible with a particular sequencing platform. In certain cases, the primers used may contain a molecular barcode (an "index") so that different pools can be pooled together before sequencing, and the sequence reads can be traced to a particular sample using the barcode sequence.

In some cases, the sequencing may be performed at certain "depth." The terms "depth" or "coverage" as used herein refers to the number of times a nucleotide is read during the sequencing process. In regards to single cell RNA sequencing, "depth" or "coverage" as used herein refers to the number of mapped reads per cell. Depth in regards to genome sequencing may be calculated from the length of the original genome (G), the number of reads (N), and the average read length (L) as N×L/G. For example, a hypothetical genome with 2,000 base pairs reconstructed from 8 reads with an average length of 500 nucleotides will have 2× redundancy.

In some cases, the sequencing herein may be low-pass sequencing. The terms "low-pass sequencing" or "shallow sequencing" as used herein refers to a wide range of depths greater than or equal to 0.1× up to 1×. Shallow sequencing may also refer to about 5000 reads per cell (e.g., 1,000 to 10,000 reads per cell).

In some cases, the sequencing herein may deep sequencing or ultra-deep sequencing. The term "deep sequencing" as used herein indicates that the total number of reads is many times larger than the length of the sequence under study. The term "deep" as used herein refers to a wide range of depths greater than 1× up to 100×. Deep sequencing may also refer to 100× coverage as compared to shallow sequencing (e.g., 100,000 to 1,000,000 reads per cell). The term "ultra-deep" as used herein refers to higher coverage (>100-fold), which allows for detection of sequence variants in mixed populations.

In some embodiments, the method may further comprise analyzing the target nucleic acid based, at least in part, on the sequence read of the sequencing construct, as described herein. In some embodiments, analyzing the target nucleic acid may comprise quantifying the target nucleic acid. In some embodiments, the method comprises amplifying the sequencing construct, thereby generating a sequencing library comprising the amplified sequencing construct.

Sequencing Construct

The system may further comprise one or more sequencing constructs. A sequencing construct is a polynucleotide that can be sequenced. In some embodiments, a sequencing construct may comprise at least a portion of a sensing oligo and at least a portion of a targeting probe. The sequencing construct may comprise one or more sequencing adaptors, one or more barcodes, and one or more target region of interest.

In some cases, the systems may comprise a sequencing library comprising a plurality of sequencing constructs or amplicons thereof.

Adaptors

The targeting probe herein may comprise one or more adaptors. Alternatively or additionally, the sensing oligo may comprise one or more adaptors. In some examples, a targeting probe may comprise an adaptor at its 5' end and a sensing oligo may comprise an adaptor at its 5' end.

An adaptor may be an oligonucleotide that can be attached to one or more nucleic acids. The adaptor may comprise a plurality of oligonucleotides. The adaptor may comprise DNA, RNA, or hybrid thereof. The adaptor may be single stranded, double-stranded, a mixture thereof. The adaptor may comprise a molecular barcode, sample index, primer sequence, linker sequence, or a combination thereof. The molecular barcode may be adjacent to the sample index. The molecular barcode may be adjacent to the primer sequence. The sample index may be adjacent to the primer sequence. A linker sequence may connect the molecular barcode to the sample index. A linker sequence may connect the molecular barcode to the primer sequence. A linker sequence may connect the sample index to the primer sequence.

An adaptor may be a molecule configured to accept or receive a barcode. In some examples, the adaptor may comprise an overhang, and the barcode may comprise a sequence capable of hybridizing to the overhang. For example, an adaptor may include a single-stranded nucleic acid sequence (for example, an overhang) capable of hybridizing to a given barcode (for example, a barcode), for example, via a sequence complementary to a portion or the entirety of the nucleic acid barcode. In certain embodiments, this portion of the barcode is a standard sequence held constant between individual barcodes. The hybridization couples the adaptor to the barcode. In some embodiments, the adaptor may be associated with (for example, attached to) a target molecule. As such, the adaptor may serve as the means through which a barcode is attached to a target molecule. An adaptor may be attached to a target molecule according to methods known in the art. For example, a barcode receiving adaptor may be attached to a polypeptide target molecule at a cysteine residue (for example, a C-terminal cysteine residue). An adaptor may be used to identify a particular condition related to one or more target molecules, such as a cell of origin or a discreet volume of origin. For example, a target molecule can be a cell surface protein expressed by a cell, which receives a cell-specific adapter. The barcode receiving adaptor can be conjugated to one or more barcodes as the cell is exposed to one or more conditions, such that the original cell of origin for the target molecule, as well as each condition to which the cell was exposed, can be subsequently determined by identifying the sequence of the barcode receiving adaptor/barcode concatemer.

Sequencing Adaptor

In some embodiments, the adaptor may be a sequencing adaptor. The term "sequencing adaptor," as used herein, generally refers to a molecule (e.g., polynucleotide) that is adapted to permit a sequencing instrument to sequence a target polynucleotide, such as by interacting with the target polynucleotide to enable sequencing. The sequencing adaptor may permit the target polynucleotide to be sequenced by the sequencing instrument. In an example, the sequencing adaptor may comprise a nucleotide sequence that hybridizes or binds to a capture polynucleotide attached to a solid support of a sequencing system, such as a flow cell. In another example, the sequencing adaptor comprises a nucleotide sequence that hybridizes or binds to a polynucleotide to generate a hairpin loop, which permits the target polynucleotide to be sequenced by a sequencing system. The sequencing adaptor can include a sequencer motif, which can be a nucleotide sequence that is complementary to a flow cell sequence of other molecule (e.g., polynucleotide) and usable by the sequencing system to sequence the target polynucleotide. The sequencer motif can also include a primer sequence for use in sequencing, such as sequencing by synthesis. The sequencer motif can include the sequence(s) needed to couple a library adaptor to a sequencing system and sequence the target polynucleotide. In some cases, the targeting probe may comprise a sequencing adaptor, e.g., at its 5' end. In certain cases, the sensing oligo may comprise a sequencing adaptor, e.g., at its 5'e end.

In some cases, the sequencing adaptor may be from about 5 nt to about 50 nt, from about 5 nt to about 40 nt, from about 5 nt to about 30 nt, from about 5 nt to about 15 nt, from about 10 nt to about 20 nt, from about 15 nt to about 25 nt, from about 20 nt to about 30 nt in length. In some examples, the sequencing adaptor may be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nt in length.

In certain embodiments, the at least one targeting probe includes or is linked to sequencing adapters (for example, universal primer recognition sequences) such that the probe and sequencing adapter elements are both coupled to the target molecule. In particular examples, the sequence of the probe is amplified, for example using PCR. In some embodiments, the targeting probe may comprise a primer binding site. As such, the targeting probe may comprise a barcode.

In some embodiments, the adaptor in the second sensing probe is at a 3' side of the hybridization region.

Primer Binding Sites

The targeting probe and/or the sensing oligo may comprise one or more primer binding sites. The primer binding site may be a sequence capable of hybridizing with one or more primers, e.g., sequencing primers, amplification primers, etc. In some examples, a primer binding site may be in an adaptor described herein.

Primers

The system may further comprise one or more primers. The primers may be used for amplification, sequencing, nucleic acid detecting, nucleic acid capturing, or a combination thereof. The primers may bind to the primer binding sites described herein. In some cases, a primer may be configured to bind to at least a portion of a targeting probe. In some cases, a primer may be configured to bind to at least a portion of the second sensing oligo.

Barcode

The targeting probe and/or the sensing oligo may comprise one or more barcode as described herein. In some cases, the barcode may comprise a unique molecular identifier (UMI) as defined herein. In one example, the targeting probe comprises a UMI.

The term "barcode" as used herein refers to a short sequence of nucleotides (for example, DNA or RNA) that is used as an identifier for an associated molecule, such as a target molecule and/or target nucleic acid, or as an identifier of the source of an associated molecule, such as a cell-of-origin. A barcode may also refer to any unique, non-naturally occurring, nucleic acid sequence that may be used to identify the originating source of a nucleic acid fragment. Barcoding may be performed based on any of the compositions or methods disclosed in patent publication WO 2014047561 A1, Compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell. A nucleic acid barcode or can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. Target molecule and/or target nucleic acids can be labeled with multiple nucleic acid barcodes in combinatorial fashion, such as a nucleic acid barcode concatemer. Typically, a nucleic acid barcode is used to identify a target molecule and/or target nucleic acid as being from a particular discrete volume, having a particular physical property (for example, affinity, length, sequence, etc.), or having been subject to certain treatment conditions. Target molecule and/or target nucleic acid can be associated with multiple nucleic acid barcodes to provide information about all of these features (and more).

In some embodiments, the barcode may comprise a unique molecular identifier (UMI). The term "unique molecular identifiers" as used herein refers to a sequencing linker or a subtype of nucleic acid barcode used in a method that uses molecular tags to detect and quantify unique amplified products. A UMI is used to distinguish effects through a single clone from multiple clones. The term "clone" as used herein may refer to a single mRNA or target nucleic acid to be sequenced. The UMI may also be used to determine the number of transcripts that gave rise to an amplified product, or in the case of target barcodes as described herein, the number of binding events. In preferred embodiments, the amplification is by PCR, multiple displacement amplification (MDA), or isothermal amplification.

METHODS FOR GENERATING SINGLE-CELL MOLECULAR ANALYSIS

Split and Pool Methods

In some embodiments, the invention provides methods for generating single-cell molecular analysis comprising; a) delivering one or more proximity dependent probes to a cell population, wherein each proximity dependent probe comprises a target binding region configured to bind one or more target RNAs and a primer binding site region; b) linking bound proximity dependent probes; c) using combinatorial split-and-pool strategies, such as ligation, to add sequential barcodes to the linked proximity dependent probes to attach a unique barcode to the set of probes derived from single cells; d) amplifying the ligated probes using the primer pair, wherein the barcode is incorporated into each resulting amplicon; and e) quantifying target RNAs in each individual cell based at least in part on sequencing the resulting amplicons.

Proximity dependent probes of the art are generally used in pairs, and individually consist of an analyte-binding domain with specificity to the target analyte, and a nucleic acid domain coupled thereto. The analyte-binding domain can be for example a nucleic acid "aptamer" (Fredriksson et al (2002) Nat Biotech 20:473-477) or can be proteinaceous, such as a monoclonal or polyclonal antibody (Gullberg et al (2004) Proc Natl Acad Sci USA 101:8420-8424). The respective analyte-binding domains of each proximity probe pair may have specificity for different binding sites on the analyte, which analyte may consist of a single molecule or a complex of interacting molecules, or may have identical specificities, for example in the event that the target analyte exists as a multimer. When a proximity probe pair comes into close proximity with each other, which will primarily occur when both are bound to their respective sites on the same analyte molecule, the nucleic acid domains are able to be joined to form a new nucleic acid sequence by means of a ligation reaction. This may be templated by a splint oligonucleotide subsequently added to the reaction, said splint oligonucleotide containing regions of complementarity for the ends of the respective nucleic acid domains of the proximity probe pair. The new nucleic acid sequence thereby generated serves to report the presence or amount of analyte in a sample, and can be qualitatively or quantitatively detected, for example by real-time, quantitative PCR (q-PCR). Generation of a positive signal is generally dependent on binding/hybridizing in close enough proximity so that the probes can be linked/connected by means including, but not necessarily limited to, extension, ligation, and hybridization.

Methods described for proximity ligation assay (PLA) or proximity extension assay (PEA) may be found in Fredriksson S, et al. (2002) Protein detection using proximity-dependent DNA ligation assays; Nature biotechnology 20: 473-477; Gullberg M, et al. (2004) Cytokine detection by antibody-based proximity ligation; Proceedings of the National Academy of Sciences of the United States of America 101: 8420-8424; and Lundberg M, et al. (2011) Homogeneous antibody-based proximity extension assays provide sensitive and specific detection of low-abundant proteins in human blood; Nucleic acids research 39(15): e102. PEA is based on pairs of antibodies that are linked to oligonucleotides having slight affinity to one another (PEA probes). Upon target binding the probes are brought in proximity, and the two oligonucleotides are extended by a DNA polymerase forming a unique amplification identifier that now acts as a unique surrogate marker for the specific antigen.

In specific embodiments, each proximity dependent probe comprises a target binding region configured to bind a target RNA and a primer binding site region. In specific embodiments, the bound proximity dependent probes are linked.

In some embodiments, one or more proximity dependent probes may target at least 5, at least 10, at least 20, at least 30, at least 40, at least 50, at least 60, at least 70, at least 80, at least 90, at least 100, at least 200, at least 300, at least 500, at least 1000, or at least 10,000 target RNAs.

In some embodiments, multiple proximity dependent probes may bind to the same target RNA. In some embodiments, 5, 10, 20, 30, 40, 50, 60, 70, 80, 90, 100, 200, 300, 500, or 1000 proximity dependent probes may be used per target RNA. In some embodiments, increasing the number of unique MIPs or probes per target gene may lead to higher sensitivity of the probes, thus allowing for the study of target genes that are expressed at a very low level.

In some embodiments, 2 to 100 proximity dependent probes may be used per target RNA.

In some embodiments, Split-Pool Recognition of Interactions by Tag Extension (SPRITE) may be envisioned, allowing one to map RNA and DNA interactions in 3-dimensional spatial proximity with single molecule precision. In the SPRITE method, interacting molecules are crosslinked in cells, cells are lysed, nuclei isolated, and chromatin is digested to isolate crosslinked complexes that are present in 3D proximity in vivo. SPRITE uses a split-and-pool strategy to uniquely barcode all molecules within a crosslinked complex by repeatedly splitting all complexes into a 96-well plate (split), ligating a unique tag sequence within each well (tag), and then pooling these complexes into a single tube (pool). This split, tag, and pool process is repeated several times (usually 6-8 times) such that the final RNA and DNA products contain a series of tags ligated to each molecule, which may be referred to as a barcode. Because all molecules in a crosslinked complex are tethered together, they sort into the same well of a 96-well plate during each round of this split-pool process and will therefore obtain the same unique tags. Conversely, molecules that are not crosslinked together (i.e. in separate complexes) will sort independently from each other during each round of split-and-pool tagging. In this way, interacting molecules can be identified by sequencing DNA and RNA and matching their associated barcodes.

In SPRITE, cells may be crosslinked using a mixture of formaldehyde and DSG (protein-protein crosslinker), which has previously been demonstrated to be ideal for mapping RNA-DNA interactions. Nuclei are isolated from crosslinked cells, DNA and RNA are fragmented using controlled enzymatic digestion, and a double stranded DNA adapter and a single stranded adaptor with a partially double-stranded DNA overhang to RNA (RPM) are ligated to DNA (DPM). These adapters are designed to contain the same single stranded overhang ("sticky end"), allowing ligation of the same set of tags to RNA and DNA molecules with high ligation efficiency (>95%). The sample is split into 96 wells and, in each well, ligation of a unique tag to the DPM and RPM adapters is performed. Two sets of barcode sequences are designed, called the "odd" and "even" set—the odd set contains a sticky end that can only bind to the even barcodes and vice versa. This design allows the use an arbitrary number of barcoding rounds with 2 sets of barcode sequences while avoiding chimeras in each round. All 96 samples are pooled into a single tube and the sample is re-split into 96 wells at each step alternating between ligations of an even or odd barcode. This split-and-pool procedure is then repeated between 6-8 rounds, depending on the anticipated complexity of the samples utilized—the more cells that are used, the more rounds needed. The RNA is reverse transcribed into a cDNA using the double stranded overhang already present from the RPM and barcodes. The RNA and DNA fragments are PCR amplified and paired-end sequencing is performed to read out the sequence of the RNA or DNA (read 1) and its associated molecular interaction barcode (read 2). Single molecule spatial clusters are defined by: (i) identifying the ligated tags for each read-pair after correcting for any sequencing errors, (ii) defining the identity of the molecule as RNA or DNA by identification of the RPM or DPM adaptor, respectively, (iii) mapping the molecule to the reference genome (for DNA) or transcribed sequences (for RNA), and (iv) combining all DNA and RNA molecules containing the same barcodes into a single "cluster".

There are several features that make SPRITE a suitable technology for the present invention. SPRITE can accurately map DNA-DNA, RNA-DNA, and RNA-RNA interactions in the same cells, SPRITE provides 3-dimensional spatial resolution of these interactions, and SPRITE can simultaneously measure higher-order, beyond pairwise, spatial contacts with single molecule precision.

After sequential addition of barcodes to the linked proximity dependent probes, the ligated probes may be amplified using a primer pair, as described elsewhere herein. As such, the barcode is incorporated into each resulting amplicon and the target RNAs may be quantified in each individual cell based at least in part on sequencing the resulting amplicons, as described elsewhere herein.

The method may further comprise delivering DNA-tagged protein binding molecules, amplifying the DNA tags to generate sequencing amplicons and quantifying target protein abundance based at least in part on sequencing of amplicons.

In specific embodiments, DNA-tagged protein binding molecules may be delivered to the cell population. Any suitable protein-binding molecule may be used, such as for example, but not necessarily limited to, aptamers, antibodies, DNA-conjugated lectins, or affinity reagents. The DNA tags may then be amplified using any suitable amplification technique as described herein, and the resulting sequencing amplicons may be used to quantify target protein abundance based at least in part on sequencing of amplicons.

Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, cells, tissues and organisms. Nucleic acid aptamers have specific binding affinity to molecules through interactions other than classic Watson-Crick base pairing. Aptamers are useful in biotechnological and therapeutic applications as they offer molecular recognition properties similar to antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. In certain embodiments, RNA aptamers may be expressed from a DNA construct. In other embodiments, a nucleic acid aptamer may be linked to another polynucleotide sequence. The polynucleotide sequence may be a double stranded DNA polynucleotide sequence. The aptamer may be covalently linked to one strand of the polynucleotide sequence. The aptamer may be ligated to the polynucleotide sequence. The polynucleotide sequence may be configured, such that the polynucleotide sequence may be linked to a solid support or ligated to another polynucleotide sequence.

Aptamers, like peptides generated by phage display or monoclonal antibodies ("mAbs"), are capable of specifically binding to selected targets and modulating the target's activity, e.g., through binding, aptamers may block their target's ability to function. A typical aptamer is 10-15 kDa in size (30-45 nucleotides), binds its target with sub-nanomolar affinity, and discriminates against closely related targets (e.g., aptamers will typically not bind other proteins from the same gene family). Structural studies have shown that aptamers are capable of using the same types of binding interactions (e.g., hydrogen bonding, electrostatic complementarity, hydrophobic contacts, steric exclusion) that drives affinity and specificity in antibody-antigen complexes.

Antibodies are polypeptide ligands comprising at least a light chain and/or heavy chain immunoglobulin variable region (or fragment thereof) which specifically recognizes and binds an epitope of an antigen, such as a protein, or a fragment thereof. Antibodies can include a heavy and a light chain, each of which has a variable region, termed the variable heavy (VH) region and the variable light (VL) region. The term also includes recombinant forms such as chimeric antibodies (for example, humanized murine antibodies), heteroconjugate antibodies (such as, bispecific antibodies). An antibody or fragment thereof may be multispecific, for example, bispecific. Antibodies include all known forms of antibodies and other protein scaffolds with antibody-like properties. For example, the antibody can be a monoclonal antibody, a polyclonal antibody, human antibody, a humanized antibody, a bispecific antibody, a monovalent antibody, a chimeric antibody, an immunoconjugate, or a protein scaffold with antibody-like properties, such as fibronectin or ankyrin repeats. The antibody can have any of the following isotypes: IgG (for example, IgG1, IgG2, IgG3, and IgG4), IgM, IgA (for example, IgA1, IgA2, and IgAsec), IgD, or IgE.

In most mammals, including humans, whole antibodies have at least two heavy (H) chains and two light (L) chains connected by disulfide bonds. Each heavy chain includes a heavy chain variable region (VH) and a heavy chain constant region (CH). However, single chain VHH variants, such as found in camelids, and fragments thereof, are also included. The heavy chain constant region includes three domains, CH1, CH2, and CH3 and a hinge region between CH1 and CH2. Each light chain includes a light chain variable region (VL) and a light chain constant region. The light chain constant region includes the domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

Included are intact immunoglobulins and the variants and portions of them well known in the art, such as Fab fragments, Fab' fragments, F(ab)'2 fragments, single chain Fv proteins ("scFv"), and disulfide stabilized Fv proteins ("dsFv") Fd, Feb, or SMIP. An antibody fragment may be, for example, a diabody, triabody, affibody, nanobody, aptamer, domain antibody, linear antibody, single-chain antibody, or multispecific antibodies formed from antibody fragments. Examples of antibody fragments include: (i) a Fab fragment: a monovalent fragment consisting of VL, VH, CL, and CH1 domains; (ii) a F(ab')2 fragment: a bivalent fragment including two Fab fragments linked by a disulfide bridge at the hinge region; (iii) a Fd fragment: a fragment consisting of VH and CH1 domains; (iv) a Fv fragment: a fragment consisting of the VL and VH domains of a single arm of an antibody; (v) a dAb fragment: a fragment including VH and VL domains; (vi) a dAb fragment: a fragment consisting of a VH domain or a VHH domain (such a Nanobody™); (vii) a dAb fragment: a fragment consisting of a VH or a VL domain; (viii) an isolated complementarity determining region (CDR); and (ix) a combination of two or more isolated CDRs which may optionally be joined by a synthetic linker. Furthermore, although the two domains of the Fv fragment, VL and VH, are coded for by separate genes, they can be joined, using recombinant methods, for example, by a synthetic linker that enables them to be made as a single protein chain in which the VL and VH regions pair to form monovalent molecules (known as single chain Fv (scFv)). Antibody fragments may be obtained using conventional techniques known to those of skill in the art, and may, in some instances, be used in the same manner as intact antibodies. Antigen-binding fragments may be produced by recombinant DNA techniques or by enzymatic or chemical cleavage of intact immunoglobulins. An antibody fragment may further include any of the antibody fragments described above with the addition of additional C-terminal amino acids, N-terminal amino acids, or amino acids separating individual fragments.

An antibody may be referred to as chimeric if it includes one or more variable regions or constant regions derived from a first species and one or more variable regions or constant regions derived from a second species. Chimeric antibodies may be constructed, for example, by genetic engineering. A chimeric antibody may include immunoglobulin gene segments belonging to different species (for example, from a mouse and a human).

A human antibody refers to a specific binding agent having variable regions in which both the framework and CDR regions are derived from human immunoglobulin sequences. Furthermore, if the antibody contains a constant region, the constant region also is derived from a human immunoglobulin sequence. A human antibody may include amino acid residues not identified in a human immunoglobulin sequence, such as one or more sequence variations, for example, mutations. A variation or additional amino acid may be introduced, for example, by human manipulation. A human antibody of the present disclosure is not chimeric.

Antibodies may be humanized, meaning that an antibody that includes one or more complementarity determining regions (for example, at least one CDR) substantially derived from a non-human immunoglobulin or antibody is manipulated to include at least one immunoglobulin domain having a variable region that includes a variable framework region substantially derived from a human immunoglobulin or antibody.

Methods for attaching nucleic acids to antibodies are well known in the art, and any suitable approach is encompassed within the presently disclosed methods, compositions, and kits (see, e.g., WO2016100976 A2). For example, in some embodiments antibodies may be attached to nucleic acid molecules using the methods described in Gullberg, et al. (2004), PNAS 101(22):8420-8424, and Boozer, et al. (2004), Analytical Chemistry 76(23):6967-6972, both of which are incorporated herein by reference. In some embodiments, antibodies may be attached to nucleic acid molecules by random coupling to free amines. In some embodiments, the antibodies may be attached to nucleic acid molecules by random coupling to free amines using a 10-to-1 ratio of nucleic acid to antibody. In some embodiments, antibodies may be attached to nucleic acid molecules using the methods described in Kozlov, et al. (2004), Biopolymers, 73 621-630, which is incorporated herein by reference. In some embodiments, antibodies may be attached to nucleic acid molecules using hydrazine chemistry. In some embodiments, antibodies may be attached to nucleic acid molecules using "tadpoles" as described in Nolan (2005), Nature Methods 2: 11-12, which is incorporated herein by reference. In general, antibodies may be attached to nucleic acid molecules using any suitable method known in the art for generating engineered antibodies, including the methods described herein.

In some embodiments, cells can be stained with a sample specific barcoded antibody using methods and oligo linked antibodies similar to those described previously that target an epitope accessible from staining buffer (Stoeckius et al., Simultaneous epitope and transcriptome measurement in single cells. Nat Methods. 2017 September; 14(9):865-868).

In certain embodiments, a streptavidin-biotin interaction may be used to link oligonucleotides to antibodies. In certain embodiments, the antibody-oligonucleotide includes a disulfide link at the 5' end of the oligonucleotide which allows the oligo to be released from the antibody with reducing agents. In certain embodiments, highly specific, FACS optimized monoclonal or polyclonal antibodies are selected.

Antibodies may be conjugated to oligonucleotides containing sample barcode sequences and a polyA tail. Oligonucleotides may be conjugated to antibodies by streptavidin-biotin conjugation using the LYNX Rapid Streptavidin Antibody Conjugation Kit (Bio-Rad, USA), according to manufacturer's instructions with modifications. Specifically, Applicants can label 15 μg of antibody with 10 μg of streptavidin. At this ratio, up to two streptavidin tetramers can theoretically be conjugated to one antibody, which results in 4-8 binding sites for biotin on each antibody. DNA-oligonucleotides can be purchased and/or synthesized with a 5' biotin modification or with a 5' amine modification and biotinylated using NHS-chemistry according to manufacturer's instructions (EZ Biotin S-S NHS, Thermo Fisher Scientific, USA). The disulfide bond allows separation of the oligo from the antibody with reducing agents. Separation of the oligo from the antibody may not be needed for all applications. Excess Biotin-NHS can be removed by gel filtration (Micro Biospin 6, Bio-Rad) and ethanol precipitation. Streptavidin-labelled antibodies can be incubated with biotinylated oligonucleotides in excess (1.5× theoretically available free streptavidin) overnight at 4° C. in PBS containing 0.5M NaCl and 0.02% Tween. Unbound oligo can be removed from antibodies using centrifugal filters with a 100 KDa MW cutoff (Millipore, USA). Removal of excess oligo can be verified by 4% agarose gel electrophoresis. Antibody-oligo conjugates can be stored at 4° C. supplemented with sodium azide and BSA.

Cells can be labeled with oligonucleotide linked antibodies by resuspending cells in cold PBS containing 2% BSA and 0.01% Tween (PBT) and filtering through 40 μm cell strainers (Falcon, USA) to remove potential clumps and large particles. Cells can be incubated for 10 minutes with Fc receptor block (TruStain FcX, BioLegend, USA) to block non-specific antibody binding. Subsequently cells can be incubated in with mixtures of barcoded antibodies for 5-30 minutes at 4° C. Cells can be washed 1-3× by resuspension in PBS containing 2% BSA and 0.01% Tween, followed by centrifugation (about 480 × g 5 minutes) and supernatant exchange. After the final wash, cells can be resuspended at appropriate cell concentration for library construction applications (e.g., Drop-seq, 10× Genomics, or split-pool applications).

In some embodiments, the invention may include specific binding molecules that bind substantially or preferentially only to a defined target such as a polypeptide protein, enzyme, polysaccharide, oligonucleotide, DNA, RNA, recombinant vector or a small molecule. In an example, a "capture moiety specific binding molecule" is capable of binding to a capture moiety that is linked to a nucleic acid, such as a nucleic acid barcode.

A nucleic acid-specific binding molecule binds substantially only to the defined nucleic acid, such as RNA, or to a specific region within the nucleic acid. In some embodiments a specific binding molecule is a nucleic acid barcode, that specifically binds to a target nucleic acid of interest.

A protein-specific binding molecule binds substantially only the defined protein, or to a specific region within the protein. For example, a "specific binding molecule" includes antibodies and other agents that bind substantially to a specified polypeptide. Antibodies can be monoclonal or polyclonal antibodies that are specific for the polypeptide, as well as immunologically effective portions ("fragments") thereof. The determination that a particular molecule binds substantially only to a specific polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999).

In specific embodiments, the DNA tags may be amplified to generate sequencing amplicons and the target protein abundance may be quantified based at least in part on sequencing of amplicons.

The bound proximity dependent probes may be linked by ligation, splinted ligation, hybridization, or proximity extension, as described in, but not necessarily limited to, Gullberg et al. (PNAS 101(22):8420-8424 (2004)); Fredriksson et al. (Nat Biotechnol 20(5):473-477 (2002)); Soderberg et al. Nat Methods 3(12):995-1000 (2006)); Greenwood et al. Biomol Detect Quantif 4:10-16 (2015); Maroney et al. Nat Protocol 3(2):279-287 (2008).

In certain example embodiments, the methods for genotyping single cells rely, at least in part, on ligation dependent probes. A ligation dependent probe is a probe that comprises a target binding region configured to bind a target polynucleotide and a primer binding site region. Ligation dependent probes may be used in a set of two or more. Ligation dependent probes may comprise a set of individual ligation dependent probes, with each individual ligation dependent probe configured to hybridize to a specific target nucleic acid sequence on a target polynucleotide. Target sequences on the target polynucleotide are selected to be close enough in distance on the target polynucleotide such that ligation dependent probes hybridized to said target nucleic acid sequences may be subsequently ligated together. Accordingly, in certain embodiments, ligation dependent probe pairs may bind within 1 nucleotides of on another. In some embodiments, the ligation dependent probe pairs may bind within 2 to 500 nucleotides of one another, the gap between which is filled through polymerase extension, or another polynucleotide filler, prior to ligation. Alternatively, a ligation dependent probe may be a single molecule comprising two or more target binding regions connected by linker sequences. The target binding regions comprise a nucleic acid sequence selected to hybridize to a target region on a target polynucleotide. Linker sequences are selected such that the molecule may adapt a conformation that allows the individual target binding regions to hybridize to adjacent regions on the target polynucleotide. Target sequences on the target polynucleotide are selected to be close enough in distance on the target polynucleotide such that ligation dependent probes hybridized to said target nucleic acid sequences may be subsequently ligated together. Accordingly, in certain embodiments, ligation dependent probe pairs may bind within 1, 2, 3, 4, or 5 nucleotides of one another. In certain example embodiments, the ligation dependent probes comprising two or more target binding regions may be based on molecule inversion probes (MIP), or "padlock probes." See e.g. Niedzicka et al. Sci Rep. 2016; 6:24501.

In the case of MIPs, padlock probes, and rolling circle probes, constructs for generating labeled target sequences are formed by circularizing a linear version of the probe in a template-driven reaction on a target polynucleotide followed by digestion of non-circularized polynucleotides in the reaction mixture, such as target polynucleotides, unligated probe, probe concatemers, and the like, with an exonuclease, such as exonuclease I.

Ligation dependent probes may be RNA, DNA, or a combination thereof. Ligation dependent probes may vary in length from 10 to 200 nucleotides. To allow for amplification, the ligation dependent probes may further comprise a primer binding site. The same or different primer binding site may be found on each ligation dependent probe. In certain embodiments, a set of ligation dependent probes, each ligation dependent probe comprising target binding region to a different target nucleic acid sequence on the same or different target polynucleotide, but the same primer binding set on each ligation dependent probe.

In one embodiment, the ligation dependent probes are designed to bind one or more target RNA molecules in a cell. The ligation dependent probes may be configured to bind to select RNA fragments or RNA exons for the purpose of quantifying the amount of the selected RNA fragment or exon in a sample, or configured to hybridize to a specific RNA sequence variant to detect and identify the presence of said variant in a sample.

Ligation dependent probes are delivered to a sample containing the target molecules of interest. The method of delivery will depend on the sample type. Samples sources may include biological samples of a subject, or environmental samples. These samples may be solids or liquids. The biological samples may include, but are not limited to, animal tissues such as those obtained by biopsy or post mortem, including saliva, blood, semen, plasma, sera, stool, urine, sputum, mucous, lymph, synovial fluid, spinal fluid, cerebrospinal fluid, a swab from skin or a mucosal membrane, or combination thereof. Other biological samples may include plant tissues such as leaves, roots, stems, fruit, and seeds, or sap or other liquids obtained when plant tissues are cut or plant cells are lysed or crushed. Environmental samples may include surfaces or fluids. In an example embodiment, the environmental sample is taken from a solid surface, such as a surface used in the preparation of food or other sensitive compositions and materials.

In specific embodiments, each ligation dependent probe comprises a UPS, a reverse priming site and a target binding region configured to hybridize to adjacent sites on a target DNA of interest, optionally a UMI.

In some embodiments, the ligation dependent probes may be split-ligation probes, each probe further comprising a unique molecular identifier (UMI). The term "unique molecular identifiers" (UMI) as used herein refers to a sequencing linker or a subtype of nucleic acid barcode used in a method that uses molecular tags to detect and quantify unique amplified products. A UMI is used to distinguish effects through a single clone from multiple clones. The term "clone" as used herein may refer to a single mRNA or target nucleic acid to be sequenced. The UMI may also be used to determine the number of transcripts that gave rise to an amplified product, or in the case of target barcodes as described herein, the number of binding events. In preferred embodiments, the amplification is by PCR, multiple displacement amplification (MDA), or isothermal amplification.

In certain embodiments, an UMI with a random sequence of between 4 and 20 base pairs is added to a template, which is amplified and sequenced. In preferred embodiments, the UMI is added to the 5' end of the template. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (See e.g., Islam S. et al., 2014. Nature Methods No:11, 163-166). Not being bound by a theory, the UMI's are designed such that assignment to the original can take place despite up to 4-7 errors during amplification or sequencing. Not being bound by a theory, an UMI may be used to discriminate between true barcode sequences.

UMIs can be used, for example, to normalize samples for variable amplification efficiency. For example, in various embodiments, featuring a solid or semisolid support (for example a hydrogel bead), to which nucleic acid barcodes (for example a plurality of barcodes sharing the same sequence) are attached, each of the barcodes may be further coupled to a unique molecular identifier, such that every barcode on the particular solid or semisolid support receives a distinct unique molecule identifier. A unique molecular identifier can then be, for example, transferred to a target molecule with the associated barcode, such that the target molecule receives not only a nucleic acid barcode, but also an identifier unique among the identifiers originating from that solid or semisolid support.

Each member of a given population of UMIs, on the other hand, is typically associated with (for example, covalently bound to or a component of the same molecule as) individual members of a particular set of identical, specific (for example, discreet volume-, physical property-, or treatment condition-specific) nucleic acid barcodes. Thus, for example, each member of a set of origin-specific nucleic acid barcodes, or other nucleic acid identifier or connector oligonucleotide, having identical or matched barcode sequences, may be associated with (for example, covalently bound to or a component of the same molecule as) a distinct or different UMI.

Droplet-Based Methods

In some embodiments, the invention provides methods for generating single-cell molecular analysis comprising; a) delivering one or more proximity dependent probes to a cell population, wherein each proximity dependent probe comprises a target binding region configured to bind one or more target RNAs and a primer binding site region; b) linking bound proximity dependent probes; c) isolating single cells from the cell population in separate individual discrete volumes, the individual discrete volumes further comprising a primer pair and amplification reagents, wherein the primer pair binds to the primer binding sites of the proximity dependent probes, and wherein at least one primer comprises a barcode sequence that uniquely identifies the individual discrete volume; d) amplifying the ligated probes using the primer pair, wherein the barcode is incorporated into each resulting amplicon; and e) quantifying target RNAs in each individual cell based at least in part on sequencing the resulting amplicons.

An "individual discrete volume" is a discrete volume or discrete space, such as a container, receptacle, or other defined volume or space that can be defined by properties that prevent and/or inhibit migration of nucleic acids and reagents necessary to carry out the methods disclosed herein, for example a volume or space defined by physical properties such as walls, for example the walls of a well, tube, or a surface of a droplet, which may be impermeable or semipermeable, or as defined by other means such as chemical, diffusion rate limited, electro-magnetic, or light illumination, or any combination thereof. By "diffusion rate limited" (for example diffusion defined volumes) is meant spaces that are only accessible to certain molecules or reactions because diffusion constraints effectively defining a space or volume as would be the case for two parallel laminar streams where diffusion will limit the migration of a target molecule from one stream to the other. By "chemical" defined volume or space is meant spaces where only certain target molecules can exist because of their chemical or molecular properties, such as size, where for example gel beads may exclude certain species from entering the beads but not others, such as by surface charge, matrix size or other physical property of the bead that can allow selection of species that may enter the interior of the bead. By "electro-magnetically" defined volume or space is meant spaces where the electro-magnetic properties of the target molecules or their supports such as charge or magnetic properties can be used to define certain regions in a space such as capturing magnetic particles within a magnetic field or directly on magnets. By "optically" defined volume is meant any region of space that may be defined by illuminating it with visible, ultraviolet, infrared, or other wavelengths of light such that only target molecules within the defined space or volume may be labeled. One advantage to the used of non-walled, or semipermeable is that some reagents, such as buffers, chemical activators, or other agents may be passed out through the discrete volume, while other material, such as target molecules, maybe maintained in the discrete volume or space. Typically, a discrete volume will include a fluid medium, (for example, an aqueous solution, an oil, a buffer, and/or a media capable of supporting cell growth) suitable for labeling of the target molecule with the indexable nucleic acid identifier under conditions that permit labeling. Exemplary discrete volumes or spaces useful in the disclosed methods include droplets (for example, microfluidic droplets and/or emulsion droplets), hydrogel beads or other polymer structures (for example poly-ethylene glycol di-acrylate beads or agarose beads), tissue slides (for example, fixed formalin paraffin embedded tissue slides with particular regions, volumes, or spaces defined by chemical, optical, or physical means), microscope slides with regions defined by depositing reagents in ordered arrays or random patterns, tubes (such as, centrifuge tubes, microcentrifuge tubes, test tubes, cuvettes, conical tubes, and the like), bottles (such as glass bottles, plastic bottles, ceramic bottles, Erlenmeyer flasks, scintillation vials and the like), wells (such as wells in a plate), plates, pipettes, or pipette tips among others. In certain example embodiments, the individual discrete volumes are the wells of a microplate. In certain example embodiments, the microplate is a 96 well, a 384 well, or a 1536 well microplate.

Each individual discrete volume further comprises a primer pair and amplification reagents. The primer pair comprises a nucleic acid sequence designed to hybridize to the primer binding sites of the ligation dependent probes. Where the same primer binding site is found on each ligation dependent probe, then each individual discrete volume may be loaded with the same primer pair. In specific embodiments, each individual discrete volume may further comprise primer pairs for genotyping one or more genomic loci on target nucleic acids. In some embodiments, genotyping multiple genomic loci can be achieved by use of multiple primer pairs. Thus, each primer pair may comprise a barcode sequence that uniquely identifies each individual discrete volume. In alternative embodiments, multiple genomic loci can be genotyped by use of bridged amplification strategies, by creating amplified product from target nucleic acids with primers containing one variable portion of sequence specific to the target nucleic acid and another constant portion, followed by subsequent amplification by a second set of primers that recognize the constant portions of the first set of primers.

As described elsewhere herein, the term "barcode" as used herein refers to a short sequence of nucleotides (for example, DNA or RNA) that is used as an identifier for an associated molecule, such as a target molecule and/or target nucleic acid, or as an identifier of the source of an associated molecule, such as a cell-of-origin.

In specific embodiments, at least one primer comprises a barcode sequence that uniquely identifies the individual discrete volume.

One or more nucleic acid identifiers (for example a nucleic acid barcode) can be attached, or "tagged," to a target molecule. This attachment can be direct (for example, covalent or noncovalent binding of the nucleic acid identifier to the target molecule) or indirect (for example, via an additional molecule). Such indirect attachments may, for example, include a barcode bound to a specific-binding agent that recognizes a target molecule. In certain embodiments, a barcode is attached to protein G and the target molecule is an antibody or antibody fragment. Attachment of a barcode to target molecules (for example, proteins and other biomolecules) can be performed using standard methods well known in the art. For example, barcodes can be linked via cysteine residues (for example, C-terminal cysteine residues). In other examples, barcodes can be chemically introduced into polypeptides (for example, antibodies) via a variety of functional groups on the polypeptide using appropriate group-specific reagents (see for example www.drmr.com/abcon). In certain embodiments, barcode tagging can occur via a barcode receiving adapter associate with (for example, attached to) a target molecule, as described herein.

The primers are used to amplify the ligation dependent probes. The primer pairs may bind the primer binding sites of the ligation dependent probes. Various amplification strategies may be used, such as PCR, multiple displacement amplification (MDA), rolling circle amplification (RCA), ligase chain reaction (LCR), loop-mediated isothermal amplification, helicase-dependent amplification, recombinase polymerase amplification, nucleic acid sequence-based amplification, or ramification amplification method (RAM).

Accordingly, in certain example embodiments the systems disclosed herein may include amplification reagents. Different components or reagents useful for amplification of nucleic acids are described herein. For example, an amplification reagent as described herein may include a buffer, such as a Tris buffer. A Tris buffer may be used at any concentration appropriate for the desired application or use, for example including, but not limited to, a concentration of 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 25 mM, 50 mM, 75 mM, 1 M, or the like. One of skill in the art will be able to determine an appropriate concentration of a buffer such as Tris for use with the present invention.

A salt, such as magnesium chloride ($MgCl_2$), potassium chloride (KCl), or sodium chloride (NaCl), may be included in an amplification reaction, such as PCR, in order to improve the amplification of nucleic acid fragments. Although the salt concentration will depend on the particular reaction and application, in some embodiments, nucleic acid fragments of a particular size may produce optimum results at particular salt concentrations. Larger products may require altered salt concentrations, typically lower salt, in order to produce desired results, while amplification of smaller products may produce better results at higher salt concentrations. One of skill in the art will understand that the presence and/or concentration of a salt, along with alteration of salt concentrations, may alter the stringency of a biological or chemical reaction, and therefore any salt may be used that provides the appropriate conditions for a reaction of the present invention and as described herein.

In some embodiments, amplification reagents as described herein may be appropriate for use in hot-start amplification. Hot start amplification may be beneficial in some embodiments to reduce or eliminate dimerization of adaptor molecules or oligos, or to otherwise prevent unwanted amplification products or artifacts and obtain optimum amplification of the desired product. Many components described herein for use in amplification may also be used in hot-start amplification. In some embodiments, reagents or components appropriate for use with hot-start amplification may be used in place of one or more of the composition components as appropriate. For example, a polymerase or other reagent may be used that exhibits a desired activity at a particular temperature or other reaction condition. In some embodiments, reagents may be used that are designed or optimized for use in hot-start amplification, for example, a polymerase may be activated after transposition or after reaching a particular temperature. Such polymerases may be antibody-based or aptamer-based. Polymerases as described herein are known in the art. Examples of such reagents may include, but are not limited to, hot-start polymerases, hot-start dNTPs, and photo-caged dNTPs. Such reagents are known and available in the art. One of skill in the art will be able to determine the optimum temperatures as appropriate for individual reagents.

Amplification of nucleic acids may be performed using specific thermal cycle machinery or equipment, and may be performed in single reactions or in bulk, such that any desired number of reactions may be performed simultaneously. In some embodiments, amplification may be performed using microfluidic or robotic devices, or may be performed using manual alteration in temperatures to achieve the desired amplification. In some embodiments, optimization may be performed to obtain the optimum reactions conditions for the particular application or materials. One of skill in the art will understand and be able to optimize reaction conditions to obtain sufficient amplification.

In specific embodiments, the ligated probes may be amplified using the primer pair. In specific embodiments, the barcode may be incorporated into each resulting amplicon.

PCR may be performed in the individual discrete volumes, generating cell-barcoded amplicons as previously described, and the resulting amplicons may be sequenced.

To identify and/or quantify the target polynucleotides present in the sample, single cell sequencing of the resulting amplification products ("amplicons") may be used. In some examples, an amplicon is a nucleic acid from a cell, or acellular system, such as mRNA or DNA that has been amplified. The amplicons will incorporate the primer barcode and UMI allowing for the identification of individual molecular species, the individual discrete volume of origin i.e. cell, and a relative assessment of quantity of each molecule. In certain embodiments, the invention involves high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO 2014210353 A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; and Rosenberg et al., 2017, "Scaling single cell transcriptomics through split pool barcoding" bioRxiv preprint first posted online Feb. 2, 2017, doi: dx.doi.org/10.1101/105163, all the contents and disclosure of each of which are herein incorporated by reference in their entirety.

The method may further comprise quantifying target RNA and/or genotyping target DNA loci based in part on sequencing the barcode of each amplicon. In one exemplary embodiment, RNA is detected and quantified by sequencing ligation dependent probes, and DNA is simultaneously detected by sequencing of genomic DNA PCR amplicons. Other exemplary sequencing techniques which may be used include high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352): 661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

The term "nonspecific amplification" refers to amplification products that result from primers hybridizing to sequences other than the target sequence and then serving as a substrate for primer extension. The resulting products are not the intended products of the amplification process.

In specific embodiments, DNA is first amplified using nonspecific amplification prior to detection of the one or more genomic loci.

In specific embodiments, DNA is amplified using whole genome amplification (WGA). WGA may be achieved by any means known in the art. WGA results in the amplification either of complete pools of DNA or of unknown intervening sequences between specific primer binding sites. The amplification of complete pools of DNA, termed known amplification (Lüidecke et al., 1989) or general amplification (Telenius et al., 1992), can be achieved by different means. Common to all approaches is the capability of the amplification system to unanimously amplify DNA fragments in the reaction mixture without preference for specific DNA sequences. The structure of primers used for WGA is described as totally degenerate (i.e., all nucleotides are termed N,N=A, T, G, C), partially degenerate (i.e., several nucleotides are termed N) or non-degenerate (i.e., all positions exhibit defined nucleotides).

WGA involves converting total genomic DNA to a form which can be amplified by PCR (Kinzler and Vogelstein, 1989). In this technique, total genomic DNA is fragmented via shearing or enzymatic digestion with, for instance, a restriction enzyme such as MboI, to an average size of 200-300 base pairs. The ends of the DNA are made blunt by incubation with the Klenow fragment of DNA polymerase. The DNA fragments are ligated to catch linkers consisting of a 20 base pair DNA fragment synthesized in vitro. To select against the "catch" linkers that were self-ligated, the ligation product is cleaved with XhoI. Each catch linker has one half of an XhoI site at its termini; therefore, XhoI cleaves catch linkers ligated to themselves but will not cleave catch linkers ligated to most genomic DNA fragments. The linked DNA is in a form that can be amplified by PCR using the catch oligomers as primers. The DNA of interest can then be selected via binding to a specific protein or nucleic acid and recovered. The small amount of DNA fragments specifically bound can be amplified using PCR. The steps of selection and amplification may be repeated as often as necessary to achieve the desired purity.

Methods using hybridization of probes to RNA may be multiplexed with other assays as described further below.

Such methods may further comprise delivering DNA-tagged protein binding molecules, amplifying the DNA tags to generate sequencing amplicons and quantifying target protein abundance based at least in part on sequencing of amplicons.

As described elsewhere herein, the protein binding molecule may be an aptamer or an antibody.

As described elsewhere herein, the bound proximity dependent probes may be linked by ligation, splinted ligation, hybridization, or proximity extension.

As described elsewhere herein, the proximity dependent probes may be molecular inversion probes (MIPs), HyPR probes, padlock probes, or split-ligation probes, each probe further comprising a unique molecular identifier (UMI).

As described elsewhere herein, the one or more proximity dependent probes may target at least 5, at least 10, at least 20, at least 30, at least 40, at least 50, at least 60, at least 70, at least 80, at least 90, at least 100, at least 200, at least 300, at least 500, at least 1000, or at least 10,000 target RNAs.

As described elsewhere herein, multiple proximity dependent probes may bind to the same target RNA.

As described elsewhere herein, 2 to 100 proximity dependent probes may be used per target RNA.

The individual discrete volumes may be droplets. At least one primer of the primer pair may be delivered to the individual discrete volume on a bead. As described elsewhere herein, the primer may be linked to the bead via a cleavable linker. The single cells may first be crosslinked and/or lysed and then isolated in the individual discrete volumes.

SINGLE CELL INFORMATION OBTAINED VIA COMBINATORIAL INDEXING OR DROPLET PCR

In other embodiments, the invention provides modular methods for conducting single-cell molecular analysis, comprising a) encapsulating individual cells in a hydrogel droplet, the hydrogel droplet further optionally comprising one or more primer pairs, wherein each primer in the one or more primer pairs is linked to the hydrogel matrix by a releasable linker, and wherein each primer pair comprises a target binding region for binding one or more target molecules; b) uniquely identifying each hydrogel droplet; c) releasing the one or more primer pairs from the hydrogel matrix via the releasable linker and amplifying the one or more target molecules using the one or more primer pairs thereby generating DNA and/or cDNA amplicons comprising the barcode sequences; and d) identifying and/or quantifying the one or more target molecules based, at least in part, on sequencing of the DNA and/or cDNA amplicons.

The methods are modular in that they have multi-part components to effect different outcomes or to optimize a particular outcome. In embodiments, the methods are also scalable, to allow for analysis of potentially large amounts of data.

Preparation of Hydrogel Droplets for Performing Single Cell Assays

In certain example embodiments, individual cells may be encapsulated in hydrogels. The term "hydrogel" refers to any network of polymer chains that are hydrophilic, and sometimes found as a colloidal gel, in which water is the dispersion medium. Hydrogels are highly absorbent (they can contain over 90% water) natural or synthetic polymeric networks. Hydrogels also possess a degree of flexibility very similar to natural tissue, due to their significant water content. Hydrogel may include polyvinyl alcohol, sodium polyacrylate, acrylate polymers, copolymers with an abundance of hydrophilic groups, agarose, methylcellulose, hyaluronan, and other naturally derived polymers.

Hydrogels may be prepared by any means known in the art. Exemplary hydrogels may include acrylamide/bisacrylamide. The ratio of ratio of acrylamide to bisacrylamide may range from 10:1 to 40:1. In some embodiments, the percentage of acrylamide/bisacrylamide may range from 3% to 20%. In more specific embodiments, the percentage of acrylamide/bisacrylamide may range from 4% to 10%. In some embodiments, the hydrogel may include acrylamide/di-hydroxyethylenebisacrylamide. In some embodiments, the hydrogel may include acrylamide/N,N'-bis(acryloyl)cystamine. In some embodiments, cellular biomolecules may be covalently linked to the hydrogel.

In some embodiments, the hydrogel may further comprise primer pairs comprising releasable linkers, wherein the primers are barcoded using combinatorial indexing, and wherein said barcoded primers are incorporated into DNA or cDNA amplicons by the amplification step. Releasable linkers include, but are not necessarily limited to, cleavable linkers, such as photocleavable linkers, enzymatically cleavable linkers, chemically releasable linkers.

Hydrogelled single cells may be prepared by any means known in the art. As an exemplary protocol, an adaptation of a previously described protocol is listed below (doi: 10.103/nprot.2014.123):

| Make HM solution (400 mL) | | |
|---|---|---|
| 1. | Mix | For 4%/0.05% |
| | 40% wt/vol acrylamide | 40 mL |
| | 2% (wt/vol) bisacrylamide | 10 mL |
| | 10X PBS | 40 mL |
| | 16% (wt/vol) PFA | 100 mL |
| | Distilled water | 210 mL |
| | 0.1% (w/v) ammonium persulfate VA-044 thermal initiator | 1 g |

| -continued | | |
|---|---|---|
| 2. | Keep reagents on ice | |
| 3. | Make 10 ml aliquots and freeze at Make SBC solution | −20° C. |
| 4. | Prepare stock of 20% (wt/vol) SDS in $H_2O$ (store at RT for weeks) | For 4%/0.05% |
| | 40% wt/vol acrylamide | 40 mL |
| 5. | Prepare 1M boric acid buffer (pH adjusted to 8.5). 10 g boric acid, 61.83 g NaOH. Dissolve in 700-800 mL, pH 8.5, and Q.S. to 1 L. with a little heat | |
| 6. | Freshly prepare clearing buffer by diluting 4&5 five-fold in distilled water and combine them | |

Procedure

7. Prepare the HM stock solution by thawing frozen vials on ice or in a refrigerator. Gently mix the thawed monomer solution by inverting. Keep all reagents on ice during the whole procedure. CRITICAL STEP Make sure that there is no precipitation floating in the monomer solution; this is an indicator of spontaneous polymerization of the stored monomer solution 8. Incubate the cell in HM (0.5-1 k cells/L)

9. Put samples in coolrack, open cap, and leave in desiccator vacuum for 10 minutes 10. Disconnect vacuum, keep nitrogen just above atmospheric pressure run microfluidic droplet formation whereby microfluidic channel size is adapted to generate droplets slightly larger than the cell size, 11. Use Biorad oil for droplet generation spiked with 0.4% TMED 12. Incubate at 60 C in thermocycler overnight 13. Wash sample twice with SBC buffer for 1 h at room temperature to dialyzed the remaining PFA, initiator and monomer.

14. Passive clearing of hydrogel-embedded tissue by gentle shaking in SBC buffer at 37/60 C for 2-6 hours 15. Wash with boric acid buffer (0.2M/pH 8.5 with 0.1% (vol/vol) Triton X-100) for 1-3 h at 37 C 16. Resuspend cells in PBST (0.1% Triton X in 1×PBS) for 30 min 17. Incubate in antibody/PST solution for 2-6 hours at 37 C, DAP (1 ug/ml), can also be added at this step 18. Wash off the antibodies with PBST at 4 C for 2 hours.

19. Samples can be stored in PBST (with 0.01% (wt/vol) sodium azide) at 4 C for up to a week In certain example embodiments, the sample comprises fixed cells. As described previously, any standard fixation methods known in the art may be used. Fixation of cells or tissue may involve but is not necessarily limited to, the use of cross-linking agents, such as formaldehyde, and may involve embedding cells or tissue in a paraffin wax or polyacrylamide support matrix (Chung K, et al. Nature. 2013 May 16; 497(7449): 322-7). Standard methods for delivery of nucleic acid based probes to fixed cells may be used. Example methods for delivering to fixed cells may be found in U.S. Patent Application Publication No. 2017/0067096 A1, International Patent Application No. PCT/US2015/016788, and U.S. Patent Application no. 2016/0305856 A1, each of which is incorporated herein by reference.

In some embodiments, the cells or population of cells may be obtained from a biological sample. The biological sample may be obtained from a subject suffering from a disease. The biological sample may be a tumor sample. The tumor may be any tumor. This may include, without limitation, liquid tumors such as leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, or multiple myeloma.

The tumor may also include, without limitation, solid tumors such as sarcomas and carcinomas. Examples of solid tumors include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, epithelial carcinoma, bronchogenic carcinoma, hepatoma, colorectal cancer (e.g., colon cancer, rectal cancer), anal cancer, pancreatic cancer (e.g., pancreatic adenocarcinoma, islet cell carcinoma, neuroendocrine tumors), breast cancer (e.g., ductal carcinoma, lobular carcinoma, inflammatory breast cancer, clear cell carcinoma, mucinous carcinoma), ovarian carcinoma (e.g., ovarian epithelial carcinoma or surface epithelial-stromal tumour including serous tumour, endometrioid tumor and mucinous cystadenocarcinoma, sex-cord-stromal tumor), prostate cancer, liver and bile duct carcinoma (e.g., hepatocellular carcinoma, cholangiocarcinoma, hemangioma), choriocarcinoma, seminoma, embryonal carcinoma, kidney cancer (e.g., renal cell carcinoma, clear cell carcinoma, Wilm's tumor, nephroblastoma), cervical cancer, uterine cancer (e.g., endometrial adenocarcinoma, uterine papillary serous carcinoma, uterine clear-cell carcinoma, uterine sarcomas and leiomyosarcomas, mixed mullerian tumors), testicular cancer, germ cell tumor, lung cancer (e.g., lung adenocarcinoma, squamous cell carcinoma, large cell carcinoma, bronchioloalveolar carcinoma, non-small-cell carcinoma, small cell carcinoma, mesothelioma), bladder carcinoma, signet ring cell carcinoma, cancer of the head and neck (e.g., squamous cell carcinomas), esophageal carcinoma (e.g., esophageal adenocarcinoma), tumors of the brain (e.g., glioma, glioblastoma, astrocytoma, medulloblastoma, craniopharyngioma, ependymoma, pinealoma, hemangioblastoma, acoustic neuroma, oligodendroglioma, schwannoma, meningioma), neuroblastoma, retinoblastoma, neuroendocrine tumor, melanoma, cancer of the stomach (e.g., stomach adenocarcinoma, gastrointestinal stromal tumor), or carcinoids. Lymphoproliferative disorders are also considered to be proliferative diseases.

The method may further comprise barcoding target nucleic acids using unique nucleic acid identifiers, for example origin-specific barcodes and the like. The nucleic acid identifiers, nucleic acid barcodes, can include a short sequence of nucleotides that can be used as an identifier for an associated molecule, location, or condition. In certain embodiments, the nucleic acid identifier further includes one or more unique molecular identifiers and/or barcode receiving adapters. A nucleic acid identifier can have a length of about, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 base pairs (bp) or nucleotides (nt). In certain embodiments, a nucleic acid identifier can be constructed in combinatorial fashion by combining randomly selected indices (for example, about 1, 2, 3, 4, 5, 6, 7, 8, 9, or 10 indexes). Each such index is a short sequence of nucleotides (for example, DNA, RNA, or a combination thereof) having a distinct sequence. An index can have a length of about, for example, 4, 5, 6, 7, 8, 9, 10, 11, 12, 13, 14, 15, 16, 17, 18, 19, 20, 21, 22, 23, 24, or 25 bp or nt. Nucleic acid identifiers can be generated, for example, by split-pool synthesis methods, such as those described, for example, in International Patent Publication Nos. WO 2014/047556 and WO 2014/143158, each of which is incorporated by reference herein in its entirety, or by split-pool ligation methods as described in Quinodoz et al. (Biorxiv "Higher-order inter-chromosomal hubs shape 3-dimensional genome organization in the nucleus" (2017)).

In certain example embodiments, the method further comprises introducing amplification reagents to the hydrogel droplet. Labeled target molecules and/or target nucleic acids associated origin-specific nucleic acid barcodes (optionally in combination with other nucleic acid barcodes as described herein) can be amplified by methods known in the art, such as polymerase chain reaction (PCR). For example, the nucleic acid barcode can contain universal primer recognition sequences (or universal primer binding sequences (UBS)) that can be bound by a PCR primer for PCR amplification and subsequent high-throughput sequencing. In certain embodiments, the nucleic acid barcode includes or is linked to sequencing adapters (for example, universal primer recognition sequences) such that the barcode and sequencing adapter elements are both coupled to the target molecule. In particular examples, the sequence of the origin specific barcode is amplified, for example using PCR. In some embodiments, an origin-specific barcode further comprises a sequencing adaptor. In some embodiments, an origin-specific barcode further comprises universal priming sites (UPS). A nucleic acid barcode (or a concatemer thereof), a target nucleic acid molecule (for example, a DNA or RNA molecule), a nucleic acid encoding a target peptide or polypeptide, and/or a nucleic acid encoding a specific binding agent may be optionally sequenced by any method known in the art, for example, methods of high-throughput sequencing, also known as next generation sequencing or deep sequencing. A nucleic acid target molecule labeled with a barcode (for example, an origin-specific barcode) can be sequenced with the barcode to produce a single read and/or contig containing the sequence, or portions thereof, of both the target molecule and the barcode. Exemplary next generation sequencing technologies include, for example, Illumina sequencing, Ion Torrent sequencing, 454 sequencing, SOLiD sequencing, and nanopore sequencing amongst others. In some embodiments, the sequence of labeled target molecules is determined by non-sequencing based methods. For example, variable length probes or primers can be used to distinguish barcodes (for example, origin-specific barcodes) labeling distinct target molecules by, for example, the length of the barcodes, the length of target nucleic acids, or the length of nucleic acids encoding target polypeptides. In other instances, barcodes can include sequences identifying, for example, the type of molecule for a particular target molecule (for example, polypeptide, nucleic acid, small molecule, or lipid). For example, in a pool of labeled target molecules containing multiple types of target molecules, polypeptide target molecules can receive one identifying sequence, while target nucleic acid molecules can receive a different identifying sequence. Such identifying sequences can be used to selectively amplify barcodes labeling particular types of target molecules, for example, by using PCR primers specific to identifying sequences specific to particular types of target molecules. For example, barcodes labeling polypeptide target molecules can be selectively amplified from a pool, thereby retrieving only the barcodes from the polypeptide subset of the target molecule pool.

In some embodiments, the oligonucleotides are introduced into the droplets by initially attaching the oligonucleotides to a particle (e.g., a hydrogel or a polymeric particle), then subsequently releasing the oligonucleotides from the particle after the particle has been incorporated into a droplet. See, e.g., U.S. Pat. Appl. Ser. No. 62/072,944, filed Oct. 30, 2014 or PCT Appl. Ser. No. PCT/US2015/026443, filed on Apr. 17, 2015, entitled "Systems and Methods for Barcoding Nucleic Acids," each incorporated herein by reference. The oligonucleotides are conjugated to the solid support (bead) in a releasable fashion, for instance by a photocleavable linker, an enzymatically cleavable linker, chemically releasable linker. The linker may also include an acrylamide moiety in order to link the solid support comprising a hydrogel. For example, in certain embodiments, the oligonucleotides may also contain a cleavable sequence or linker, or otherwise be releasable from the particles. In certain embodiments, the oligonucleotide may contain one or more cleavable linkers, e.g., that can be cleaved upon application of a suitable stimulus. For example, the cleavable sequence may be a photocleavable linker that can be cleaved by applying light or a cleavable linker that can be cleaved by applying a suitable chemical or enzyme.

The first and second barcode primers may be differentially cleavable. In certain embodiments, the second oligonucleotide linker is differentially cleavable as compared to the first oligonucleotide linker, whereby each linker is capable of cleavage at experimentally defined times.

Specific embodiments comprise an oligonucleotide-labeled bead with a cleavable linker directly attached to the bead, a cell barcode sequence, wherein the cell barcode sequence is the same across all oligonucleotides on said bead, but varies among the oligonucleotides on any other individual bead; and a universal primer binding sequence (UBS), wherein the UBS can hybridize to a universal primer site (UPS).

In certain other example embodiments, a recombinase polymerase amplification (RPA) reaction may be used to amplify the target nucleic acids. RPA reactions employ recombinases which are capable of pairing sequence-specific primers with homologous sequence in duplex DNA. If target DNA is present, DNA amplification is initiated and no other sample manipulation such as thermal cycling or chemical melting is required. The entire RPA amplification system is stable as a dried formulation and can be transported safely without refrigeration. RPA reactions may also be carried out at isothermal temperatures with an optimum reaction temperature of 37-42° C. The sequence specific primers are designed to amplify a sequence comprising the target nucleic acid sequence to be detected. In certain example embodiments, a RNA polymerase promoter, such as a T7 promoter, is added to one of the primers. This results in an amplified double-stranded DNA product comprising the target sequence and a RNA polymerase promoter. After, or during, the RPA reaction, a RNA polymerase is added that will produce RNA from the double-stranded DNA templates. The amplified target RNA can then in turn be detected by the CRISPR effector system. In this way target DNA can be detected using the embodiments disclosed herein. RPA reactions can also be used to amplify target RNA. The target RNA is first converted to cDNA using a reverse transcriptase, followed by second strand DNA synthesis, at which point the RPA reaction proceeds as outlined above.

In some embodiments, macromolecules are covalently fixed to the hydrogel using LabelX (for nucleic acids) or AcX (for proteins). Methods for making LabelX and/or AcX are known in the art and may be found in Chen et al. (Science 347(6221):543-548; 2015), Chen et al. (Nat Methods 13:679-684; 2016), and Tillberg et al. (Nat Biotechnol 34:987-992; 2016). In some embodiments, cell fixation is reversed using proteinase K treatment, heat treatment, and/or other methods specific to the fixation protocol.

In one exemplary embodiment, the hydrogel particles or polymer matrices are split into pools, each pool containing a unique index A and each ligation handle is ligated to a sequence in index A. All particles are then pooled and re-split into new pools containing a unique index B. After ligation, all of the particles are pooled again and re-split into new pools containing a unique index C. If each index has 100 unique sequences and for each cycle the particles are split into 100 pools each containing a unique sequence, then after 3 cycles of split and pool ligation, the barcode on any given particle possess the same one of 100$^3$=1,000,000 possible barcodes, but different particles have different sequences.

In specific embodiments, the one or more primer pairs may be released from the hydrogel matrix via the releasable linker and the one or more target molecules may be amplified using the one or more primer pairs, thereby generating DNA and/or cDNA amplicons comprising the barcode sequences. In specific embodiments, the one or more target molecules may be identified and/or quantified based, at least in part, on sequencing of the DNA and/or cDNA amplicons. As described previously, and sequencing method known in the art may be used.

Barcode primers may further comprise an oligo-dT sequence as described in the examples. Barcode primers may further comprise a T7 RNAP promoter. In specific embodiments, the hydrogel may further comprise oligo-dT primers linked to the hydrogel via a first releasable linker and one or more primer pairs linked to the hydrogel via a second releasable linker. In some embodiments, the hydrogels may be suspended in a reverse transcription mixture. The barcoded oligo-dT primers may be released via the first releasable linker and RNA may be reverse transcribed to form cDNA. The cDNA may be eluted from the hydrogels for T7 transcription and amplification to generate cDNA amplicons as described previously. The hydrogels may then be re-suspended in a PCR amplification mixture. The one or more primer pairs may be released from the hydrogel matrix via the second releasable linker and the one or more genomic DNA loci of interest may be amplified using the one or more primer pairs to generate barcoded DNA amplicons. RNA expression may be quantified in each individual cell by sequencing of barcoded cDNA amplicons and genotyping each individual cell by sequencing of barcoded DNA amplicons.

In specific embodiments, the methods described herein may be used for whole transcriptome RNA sequencing.

In some embodiments, they hydrogel may further comprise one or more DNA proximity dependent probes that comprise a target binding region configured to bind a target DNA and a primer binding site region that binds to the primers of the one or more primer pair. In specific embodiments, the method may further comprise generating single stranded DNA molecules, binding the proximity dependent probes to corresponding ssDNA target DNA, linking bound proximity dependent probes, releasing the one or more primer pairs via the releasable linker and amplifying the linked proximity dependent probes to generate proximity dependent probe amplicons. The one or more target DNAs may be detected by sequencing of the generated proximity dependent probe amplicons.

In some embodiments, hydrogel droplets may be treated with ssDNA exonuclease as described in the examples.

In specific embodiments, generation of single stranded DNA molecules comprises digesting double stranded DNA with an exonuclease. Any exonucleases known in the art may be used, such as Exonuclease I, Exonuclease II, Exonuclease III, Exonuclease IV, Exonuclease V, Exonuclease VI, Exonuclease VII, or Exonuclease VIII of E. coli. In preferred embodiments, a Lambda ssDNA exonuclease is envisioned.

As previously described, methods may further comprise non-specific amplification of dsDNA, preferably using WGA. As previously described, proximity dependent probes may be linked by ligation, splinted ligation, hybridization, or proximity extension. As previously described, the ligation dependent probes may be molecular inversion probes (MIPs), padlock probes, or split-ligation probes, each probe further comprising a UMI.

In specific embodiments, the methods described herein may be used for multiplexed DNA detection using MIPs.

In some embodiments, the hydrogel may comprise a first primer set comprising primer pairs that bind one or more target genomic loci, and a second primer set comprising primer pairs that bind a primer binding site on proximity dependent probes. In specific embodiments, one or more proximity dependent probes may be bound to one or more RNA targets after the combinatorial indexing step. The one or more bound proximity dependent probes may be linked and hydrogels may be suspended in a PCR amplification mix. The first and second primer sets may be released via the releasable linker as described herein. The one or more target genomic loci and the one or more target RNAs may be amplified to generate barcoded genomic DNA amplicons and barcoded proximity dependent probe amplicons. The type and amount of the one or more target RNAs in each individual cell may be identified and/or quantified. Each individual cell may be genotyped by sequencing the barcoded proximity dependent probe amplicons and the barcoded genomic DNA amplicons, respectively.

In specific embodiments, the proximity dependent probes may be delivered to individual fixed cells prior to encapsulating the individual fixed cells in the hydrogel droplet. In specific embodiments, the one or more proximity dependent probes may target one or more polymorphic sites in target RNAs to provide an allele-specific RNA readout.

In specific embodiments, the proximity dependent probes may comprise probes with a different 5' nucleotide directly overlapping the polymorphic site such that only a matching probe may be successfully linked. In specific embodiments, the proximity dependent probes may be MIPs with hybridization regions flanking the polymorphic region. In specific embodiments, the MIP may be extended by reverse transcription and then ligated. In specific embodiments, methods further comprise rolling circle amplification of ligated MIPs to amplify the signal resulting from a successful ligation event.

In specific embodiments, the methods provided herein may be used for targeted RNA quantification using MIPs and genotyping. In specific embodiments, the one or more targeted RNAs comprise one or more lncRNAs.

In some embodiments, the hydrogel may further comprise a nucleic acid binding molecule, a protein binding molecule, or both, for crosslinking nucleic acids and/or proteins to the hydrogel matrix. In some embodiments, the nucleic acid binding molecule may include, but is not necessarily limited to, LabelX. In some embodiments, the protein binding molecule may include, but is not necessarily limited to, AcX.

In some embodiments, the individual cells may be fixed prior to encapsulating in the hydrogel droplet. In some embodiments, the crosslinks may be reversed in the fixed cells before performing combinatorial indexing.

In some embodiments, each hydrogel droplet is uniquely identified by barcoding each primer pair via combinatorial indexing, as described elsewhere herein.

In some embodiments, each hydrogel droplet is uniquely identified by direct barcoding of target molecules comprising ligation of adapters to the target molecules followed by combinatorial indexing of the adapter molecules, as described elsewhere herein.

In some embodiments, each hydrogel droplet is uniquely identified by re-encapsulating each cell-containing droplet in an individual discrete volume together with a separate particle containing unique adapter molecules.

Targeted Genotyping by PCR

In some embodiments, each hydrogel droplet further comprises genotyping primer pairs for amplifying one or more genomic loci, at least one primer pair comprising a barcode sequence uniquely identifying each individual discrete volume. In some embodiments, the method may further comprise amplifying the one or more genomic loci and genotyping each individual cell by sequencing the resulting amplicons.

In specific embodiments, the one or more primer pairs amplify one or more genomic loci of interest to generate DNA amplicons. The amplifying step may comprise determining a genotype of each individual cell by sequencing the resulting DNA amplicons. In specific embodiments, non-specific DNA amplification may be performed prior to amplification with the one or more primer pairs. Preferred embodiments comprise WGA amplification.

In specific embodiments, nucleic acids may be cross-linked to the hydrogel matrix. In specific embodiments, the method may further comprise reversing the cross-links prior to combinatorial indexing. In some embodiments, crosslinks in the fixed cells may be reversed after performing combinatorial indexing. Crosslinks may be reversed using any method known in the art, such as for example, but not limited to, using proteinase K treatment, heat treatment, and/or other methods specific to the fixation protocol, as described herein.

In specific embodiments, a second PCR amplification is performed to add sequencing adapters to the DNA amplicons.

In some embodiments, sequencing methods comprise Whole Genome Sequencing (WGS). This process comprises determining the sequence of the entire genome of an organism, for example, humans, dogs, mice, viruses or bacteria. It is not necessary that the entire genome actually be sequenced. The WGS methods of the invention are those sequencing methods that when applied to a sample of genomic DNA are capable of obtaining the sequence of the entire genome. Whole genome sequencing can be performed using any Next Generation Sequencing technology as described herein.

In certain embodiments, the invention involves single nucleus RNA sequencing. For example, single nuclei can be segregated into discrete volumes. In certain embodiments, single nuclei can be labeled with one or more ligation dependent probes. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

In certain embodiments, the invention involves plate based single cell RNA sequencing (see, e.g., Picelli, S. et al., 2014, "Full-length RNA-seq from single cells using Smart-seq2" Nature protocols 9, 171-181, doi: 10.1038/nprot.2014.006).

In certain embodiments, the invention involves high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In some embodiments, DNA is first amplified using nonspecific amplification prior to detection of the one or more genomic loci. In some embodiments, DNA is amplified using whole genome amplification.

In some embodiments, the one or more primer pairs amplify one or more genomic DNA loci of interest to generate DNA amplicons, and the identifying step comprises determining a genotype of each individual cell by sequencing the resulting DNA amplicons.

In some embodiments, the method may further comprise non-specific DNA amplification prior to amplification with the one or more primer pairs, preferably whole-genome amplification (WGA).

In some embodiments, the method further may comprise crosslinking the cells prior to non-specific DNA amplification and before encapsulating them in hydrogels, and reversing the cross-links prior to performing PCR to amplify the genomic DNA loci. Reverse crosslinking may involve, but is not necessarily limited to, heating and treating with a protease.

In some embodiments, a second PCR amplification may be done to add sequencing adapters to the DNA amplicons.

In some embodiments, the method may further comprise the following: a) one of the primers may contain a T7 promoter sequence and add this T7 promoter sequence to the genomic DNA amplicons during PCR; b) T7 in vitro transcription may be used to further amplify the DNA amplicons to generate RNA; c) this RNA may be reverse transcribed with an appropriate adapter primer to generate cDNA; and d) the cDNA may finally be amplified to add sequencing adapters prior to high-throughput sequencing.

Other methods for genotyping single cells may involve preparing hydrogel droplets and performing WGA on the hydrogel droplets as previously described. The hydrogels may then be resuspended in a PCR mix comprising primers targeting DNA sites of interest, optionally primer pairs, wherein one primer comprises a universal primer binding sequence (UBS) as described in the examples. The hydrogels may be segregated into individual discrete volumes and the barcoded primers may be released from the hydrogel via the cleavable linker.

The linker may be chemically-cleavable, enzymatically cleavable, or photocleavable. The aptamers may further comprise a photoreactive group configured to covalently link the aptamers to captured proteins upon experimentally defined illumination. As used herein, the term "experimentally defined illumination" refers to illumination that can be performed at a point of choice in a method of using said solid support, i.e. after aptamer target recognition has taken place and non-specific proteins are washed away. The linker may be cleaved chemically or by UV treatment.

Whole Transcriptome Sequencing

In some embodiments, the hydrogel may further comprise oligo-dT primers linked to the hydrogel. As such, the method may further comprise a) suspending the hydrogels in a reverse transcription mixture; b) reverse transcribing RNA to form cDNA; and c) amplifying the resulting cDNA fragments using PCR.

Multiplexed DNA Detection Using MIPs

In some embodiments, the hydrogel may further comprise one or more DNA proximity dependent probes that comprise a target binding region configured to bind a target DNA and a primer binding site region that bind to the primers of the one or more primer pairs. As such, the method may further comprise a) generating single stranded DNA molecules; b) binding the proximity dependent probes to corresponding ssDNA target DNA; c) linking bound proximity dependent probes; d) releasing the one or more primer pairs via releasable linkers and amplifying the linked proximity dependent probes to generate proximity dependent probe amplicons; and e) detecting and/or quantifying the one or more target DNAs by sequencing of the generated proximity dependent probe amplicons.

In some embodiments, generating single stranded DNA molecules may comprise digesting double stranded DNA with an exonuclease, preferably a Lambda ssDNA exonuclease.

In some embodiments, the method may further comprise non-specific amplification of dsDNA, preferably using whole genome amplification (WGA).

In some embodiments, the proximity dependent probes may be linked by ligation, splinted ligation, hybridization, or proximity extension, but are not necessarily limited to these methods.

In some embodiments, the proximity dependent probes may be molecular inversion probes (MIPs), HyPR probes, padlock probes, or split-ligation probes, each probe further comprising a unique molecular identifier (UMI), as described elsewhere herein.

Targeted RNA Quantification Via Proximity Probes

In some embodiments, the DNA amplicons may be derived from proximity dependent probes that are hybridized to RNA and then linked through ligation.

In some embodiments, the proximity dependent probes may be molecular inversion probes (MIPs), HyPR probes, padlock probes, or split-ligation probes, as described elsewhere herein.

In some embodiments, each probe optionally further comprises a unique molecular identifier (UMI), as described elsewhere herein.

In some embodiments, the proximity dependent probes are amplified by distributing single cells into discrete volumes along with barcoded particles that are loaded at a ratio of 1-20 particles per discrete volume; and after sequencing a computational algorithm is used to infer which particle barcodes came from the same discrete volume and correspond to the same cell by analyzing the UMIs contained in the proximity-dependent probes.

In some embodiments, one or more proximity dependent probes target at least 1, at least 5, at least 10, at least 20, at least 30, at least 40, at least 50, at least 60, at least 70, at least 80, at least 90, at least 100, at least 200, at least 300, at least 500, at least 1000, or at least 10,000 target RNAs, as described elsewhere herein.

In some embodiments, multiple proximity dependent probes bind to the same target RNA. In some embodiments, 2 to 100 proximity dependent probes are used per target RNA.

In some embodiments, different numbers of proximity dependent probes are used per target RNA, in order to balance the signal coming from RNAs with different detection efficiencies or abundances.

In some embodiments, the one or more proximity dependent probes target one or more polymorphic sites in target RNAs to provide an allele-specific RNA readout. In some embodiments, the proximity dependent probes may comprise probes with a different 5' nucleotide directly overlapping the polymorphic site such that only a matching probe will be successfully linked.

In some embodiments, the proximity dependent probes are MIPs with hybridization regions flanking the polymorphic region, wherein each MIP is extended by reverse transcription and then ligated.

In some embodiments, the method may further comprise rolling circle amplification of ligated MIPs to amplify the signal resulting from a successful ligation event.

In some embodiments, the one or more target RNAs may comprise one or more lncRNAs, as described in the examples.

In some embodiments, the proximity dependent probes may be delivered to a population of fixed cells and linked to form a proximity dependent probe complex prior to encapsulating individual fixed cells in the hydrogel droplet. In some embodiments, the proximity dependent probe complex may contain an acrylate or other moiety to enable crosslinking the probe into the hydrogel upon formation of the hydrogel.

In some embodiments, the proximity probes may further contain a releasable linker to enable releasing the proximity-dependent probes from the hydrogel prior to PCR amplification.

In some embodiments, proximity dependent probes may be applied and linked after encapsulation of cells in the hydrogel.

In some embodiments, the proximity dependent probes may be applied and linked after encapsulation of cells in the hydrogel and after digestion of other cellular molecules, wherein the cellular molecules comprise protein or DNA.

GENERATION OF MULTIMODAL READOUTS

In some embodiments, the invention provides a method for conducting single-cell molecular analysis, comprising a) encapsulating individual cells in a hydrogel droplet, the hydrogel droplet further optionally comprising one or more primer pairs, wherein each primer in the one or more primer pairs is linked to the hydrogel matrix by a releasable linker, and wherein each primer pair comprises a target binding region for binding one or more target molecules; b) uniquely identifying each hydrogel droplet; c) releasing the one or more primer pairs from the hydrogel matrix via the releasable linker and amplifying the one or more target molecules using the one or more primer pairs thereby generating DNA and/or cDNA amplicons comprising the barcode sequences; and d) identifying and/or quantifying the one or more target molecules based, at least in part, on sequencing of the DNA and/or cDNA amplicons.

In some embodiments, the method may further comprise combining measurements of multiple different modalities, including combinatorial split-and-pool strategies, droplet-based methods, DNA amplification, whole transcriptome sequencing, multiplexed DNA detection using MIPs, or any combination thereof, as described elsewhere herein.

In some embodiments, the primer pairs for DNA amplification may include one or more pairs that binds one or more target genomic loci, and a second primer set comprising primer pairs that bind a primer binding site on proximity dependent probe. Such a method may comprise a) binding one or more proximity dependent probes to one or more RNA targets; b) linking the one or more bound proximity dependent probes; c) suspending hydrogels in a PCR amplification mix; d) amplifying the one or more target genomic loci and the one or more proximity dependent probes targeting RNAs to generate barcoded genomic DNA amplicons and barcoded proximity dependent probe amplicons; and e) identifying and/or quantifying the type and/or amount of the one or more target RNAs in each individual cell and genotyping each individual cell by sequencing the barcoded proximity dependent probe amplicons and the barcoded genomic DNA amplicons respectively.

In some embodiments, the proximity dependent probes may be delivered to a population of fixed cells and linked prior to encapsulating individual fixed cells in the hydrogel droplet.

Using Cell-in-Gel Platform for RNA Quantification and DNA Genotyping

In some embodiments, the primer pairs for DNA amplification include one or more pairs that binds one or more target genomic loci, and a second primer set comprising primer pairs that bind a primer binding site on proximity dependent probes. The method may comprise a) crosslinking and permeabilizing cells; b) binding one or more proximity dependent probes to one or more RNA targets; c) linking the one or more bound proximity dependent probes; d) suspending hydrogels in a PCR amplification mix; e) reversing crosslinks, such as by heating and applying a protease; f) amplifying the one or more target genomic loci and the one or more proximity dependent probes targeting RNAs to generate barcoded genomic DNA amplicons and barcoded proximity dependent probe amplicons; g) optionally performing further amplification steps, such as a second PCR or T7 in vitro transcription; and h) identifying and/or quantifying the type and/or amount of the one or more target RNAs in each individual cell and genotyping each individual cell by sequencing the barcoded proximity dependent probe amplicons and the barcoded genomic DNA amplicons respectively.

In some embodiments, a chained primer strategy may be used, wherein, for each genomic DNA target, a single primer pair is used containing appropriate adapters that can then be amplified by a second primer or primer pair containing cell barcodes, and where that same second primer or primer pair can simultaneously amplify the proximity-dependent probes.

Combining DNA Genotyping with Whole Transcriptome Readout in Cell-in-Gel Platform In some embodiments, the hydrogel may further comprise oligo-dT primers linked to the hydrogel via a first releasable linker and one or more primer pairs linked to the hydrogel via second releasable linker. The method may further comprise a) suspending the hydrogels in a reverse transcription mixture; b) releasing the barcoded oligo-dT primers via the first releasable linker and reverse transcribing RNA to form cDNA; c) eluting the cDNA from the hydrogels for amplification to generate cDNA amplicons; d) re-suspending the hydrogels in a PCR amplification mixture; e) releasing the one or more primer pairs from the hydrogel matrix via the second releasable linker and amplifying the one or more genomic DNA loci of interest using the one or more primer pairs to generate barcoded DNA amplicons; and f) quantifying RNA expression in each individual by sequencing of barcoded cDNA amplicons and genotyping each individual cell by sequencing of barcoded DNA amplicons.

Using the Cell-in-Gel Platform for RNA or DNA, in Combination with Additional Assays In some embodiments, the method may further comprise applying oligonucleotide-tagged protein binding molecules before or after encapsulating cells in hydrogels, amplifying the oligonucleotide tag using one or more primer pairs to generate barcoded oligonucleotide tag amplicons, identifying and/or quantitating target protein abundance based at least in part on sequencing the barcoded oligonucleotide tag amplicons, as described elsewhere herein.

In some embodiments, the method may further comprise suspending the hydrogels in an additional molecular assay mixture and conducting one or more additional molecular assays.

In some embodiments, the one or more additional assays may be a chromatin accessibility assay. The chromatin accessibility assay may be, but is not necessarily limited to, ATAC-seq.

In some embodiments, the one or more additional assays is an epigenetic modification assay. In some embodiments, the one or more additional assays is a chromatin folding assay. The chromatin folding assay may be Hi-C or Hi-C++.

General Cell-in-Gel Features

In some embodiments, the hydrogel may further comprise a nucleic acid binding molecule, a protein binding molecule, or both for cross-linking nucleic acids and/or proteins to the hydrogel matrix.

In some embodiments, the nucleic acid binding molecule is LabelX and the protein binding molecule is an amine reactive acrylate or acrylamide moiety, such as AcX.

In some embodiments, single cells may first be cross-linked and/or lysed and then isolated in the individual discrete volumes. In certain example embodiments, the sample comprises fixed cells. As described previously, any standard fixation methods known in the art may be used. Fixation of cells or tissue may involve but is not necessarily limited to, the use of cross-linking agents, such as formaldehyde, and may involve embedding cells or tissue in a paraffin wax or polyacrylamide support matrix (Chung K, et al. Nature. 2013 May 16; 497(7449): 322-7). Standard methods for delivery of nucleic acid based probes to fixed cells may be used. Example methods for delivering to fixed cells may be found in U.S. Patent Application Publication No. 2017/0067096 A1, International Patent Application No. PCT/US2015/016788, and U.S. Patent Application no. 2016/0305856 A1, each of which is incorporated herein by reference.

The crosslinks may be reversed in the fixed cells after encapsulating them in hydrogels.

In some embodiments, the hydrogel may comprise acrylamide/bisacrylamide, acrylamide/di-hydroxyethylenebisacrylamide, or acrylamide/N,N'-bis(acryloyl)cystamine.

In some embodiments, the ratio of acrylamide to bisacrylamide ranges from 10:1 to 40:1. In some embodiments, the percentage of acrylamide/bisacrylamide ranges from 3% to 20%.

PERTURBATION SCREENING, DRUG SCREENING

In certain embodiments, the population of cells may have been previously exposed to a perturbation. Such perturbation may be a chemical, physical or genetic perturbation, or a combination thereof.

In certain embodiments, the gene signatures described herein are screened by perturbation of target genes within said signatures. Methods and tools for genome-scale screening of perturbations in single cells using CRISPR-Cas9 have been described, herein referred to as perturb-seq (see e.g., Dixit et al., "Perturb-Seq: Dissecting Molecular Circuits with Scalable Single-Cell RNA Profiling of Pooled Genetic Screens" 2016, Cell 167, 1853-1866; Adamson et al., "A Multiplexed Single-Cell CRISPR Screening Platform Enables Systematic Dissection of the Unfolded Protein Response" 2016, Cell 167, 1867-1882; and International publication serial number WO/2017/075294). The present invention is compatible with perturb-seq, such that signature genes may be perturbed and the perturbation may be identified and assigned to the proteomic and gene expression readouts of single cells. In certain embodiments, signature genes may be perturbed in single cells and gene expression analyzed. Not being bound by a theory, networks of genes that are disrupted due to perturbation of a signature gene may be determined. Understanding the network of genes effected by a perturbation may allow for a gene to be linked to a specific pathway that may be targeted to modulate the signature and treat a cancer. Thus, in certain embodiments, perturb-seq is used to discover novel drug targets to allow treatment of specific cancer patients having the gene signature of the present invention.

The perturbation methods and tools allow reconstructing of a cellular network or circuit. In one embodiment, the method comprises (1) introducing single-order or combinatorial perturbations to a population of cells, (2) measuring genomic, genetic, proteomic, epigenetic and/or phenotypic differences in single cells and (3) assigning a perturbation(s) to the single cells. Not being bound by a theory, a perturbation may be linked to a phenotypic change, preferably changes in gene or protein expression. In preferred embodiments, measured differences that are relevant to the perturbations are determined by applying a model accounting for co-variates to the measured differences. The model may include the capture rate of measured signals, whether the perturbation actually perturbed the cell (phenotypic impact), the presence of subpopulations of either different cells or cell states, and/or analysis of matched cells without any perturbation. In certain embodiments, the measuring of phenotypic differences and assigning a perturbation to a single cell is determined by performing single cell RNA sequencing (RNA-seq). In preferred embodiments, the single cell RNA-seq is performed by any method as described herein (e.g., Drop-seq, InDrop, 10× genomics). In certain embodiments, unique barcodes are used to perform Perturb-seq. In certain embodiments, a guide RNA is detected by RNA-seq or sequencing of ligation dependent probes using a transcript expressed from a vector encoding the guide RNA. The transcript may include a unique barcode specific to the guide RNA. Not being bound by a theory, a guide RNA and guide RNA barcode is expressed from the same vector and the barcode may be detected by RNA-seq or sequencing of ligation dependent probes. Not being bound by a theory, detection of a guide RNA barcode is more reliable than detecting a guide RNA sequence, reduces the chance of false guide RNA assignment and reduces the sequencing cost associated with executing these screens. Thus, a perturbation may be assigned to a single cell by detection of a guide RNA barcode in the cell. In certain embodiments, a cell barcode is added to the RNA in single cells, such that the RNA may be assigned to a single cell. Generating cell barcodes is described herein for single cell sequencing methods. In certain embodiments, a Unique Molecular Identifier (UMI) is added to each individual transcript and protein capture oligonucleotide. Not being bound by a theory, the UMI allows for determining the capture rate of measured signals, or preferably the binding events or the number of transcripts captured. Not being bound by a theory, the data is more significant if the signal observed is derived from more than one protein binding event or transcript. In preferred embodiments, Perturb-seq is performed using a guide RNA barcode expressed as a polyadenylated transcript, a cell barcode, and a UMI.

Perturb-seq combines emerging technologies in the field of genome engineering, single-cell analysis and immunology, in particular the CRISPR-Cas9 system and droplet single-cell sequencing analysis. In certain embodiments, a CRISPR system is used to create an INDEL at a target gene. In other embodiments, epigenetic screening is performed by applying CRISPRa/i/x technology (see, e.g., Konermann et al. "Genome-scale transcriptional activation by an engineered CRISPR-Cas9 complex" Nature. 2014 Dec. 10. doi: 10.1038/nature14136; Qi, L. S., et al. (2013). "Repurposing CRISPR as an RNA-guided platform for sequence-specific control of gene expression". Cell. 152 (5): 1173-83; Gilbert, L. A., et al., (2013). "CRISPR-mediated modular RNA-guided regulation of transcription in eukaryotes". Cell. 154 (2): 442-51; Komor et al., 2016, Programmable editing of a target base in genomic DNA without double-stranded DNA cleavage, Nature 533, 420-424; Nishida et al., 2016, Targeted nucleotide editing using hybrid prokaryotic and vertebrate adaptive immune systems, Science 353(6305); Yang et al., 2016, Engineering and optimizing deaminase fusions for genome editing, Nat Commun. 7:13330; Hess et al., 2016, Directed evolution using dCas9-targeted somatic hypermutation in mammalian cells, Nature Methods 13, 1036-1042; and Ma et al., 2016, Targeted AID-mediated mutagenesis (TAM) enables efficient genomic diversification in mammalian cells, Nature Methods 13, 1029-1035). Numerous genetic variants associated with disease phenotypes are found to be in non-coding region of the genome, and frequently coincide with transcription factor (TF) binding sites and non-coding RNA genes. Not being bound by a theory, CRISPRa/i/x approaches may be used to achieve a more thorough and precise understanding of the implication of epigenetic regulation. In one embodiment, a CRISPR system may be used to activate gene transcription. A nuclease-dead RNA-guided DNA binding domain, dCas9, tethered to transcriptional repressor domains that promote epigenetic silencing (e.g., KRAB) may be used for "CRISPRi" that represses transcription. To use dCas9 as an activator (CRISPRa), a guide RNA is engineered to carry RNA binding motifs (e.g., MS2) that recruit effector domains fused to RNA-motif binding proteins, increasing transcription. A key dendritic cell molecule, p65, may be used as a signal amplifier, but is not required.

In certain embodiments, other CRISPR-based perturbations are readily compatible with Perturb-seq, including alternative editors such as CRISPR/Cpf1. In certain embodiments, CRISPR-based perturbations target RNA molecules using Cas13. In certain embodiments, Perturb-seq uses Cpf1 as the CRISPR enzyme for introducing perturbations. Not being bound by a theory, Cpf1 does not require Tracr RNA and is a smaller enzyme, thus allowing higher combinatorial perturbations to be tested.

In one embodiment, CRISPR/Cas9 may be used to perturb protein-coding genes or non-protein-coding DNA. CRISPR/Cas9 may be used to knockout protein-coding genes by frameshifts, point mutations, inserts, or deletions. An extensive toolbox may be used for efficient and specific CRISPR/Cas9 mediated knockout as described herein, including a double-nicking CRISPR to efficiently modify both alleles of a target gene or multiple target loci and a smaller Cas9 protein for delivery on smaller vectors (Ran, F. A., et al., In vivo genome editing using *Staphylococcus aureus* Cas9. Nature. 520, 186-191 (2015)). A genome-wide sgRNA mouse library (~10 sgRNAs/gene) may also be used in a mouse that expresses a Cas9 protein (see, e.g., WO2014204727A1).

In one embodiment, perturbation is by deletion of regulatory elements. Non-coding elements may be targeted by using pairs of guide RNAs to delete regions of a defined size, and by tiling deletions covering sets of regions in pools.

In one embodiment, perturbation of genes is by RNAi. The RNAi may be shRNA's targeting genes. The shRNA's may be delivered by any methods known in the art. In one embodiment, the shRNA's may be delivered by a viral vector. The viral vector may be a lentivirus, adenovirus, or adeno associated virus (AAV).

In some embodiments, perturbation of genes may be by CRISPR, RNAi, zinc finger nuclease, transcription activator-like effector nuclease, or meganuclease genetic perturbation screen.

In some embodiments, the genetic perturbation may comprise gene knock-outs, gene knock-ins, transpositions, inversions, and/or one or more nucleotide insertions, deletions, or substitutions. In some embodiments, genetic perturbation may be confirmed by genotyping the target DNA loci according to any of the methods described herein.

In some embodiments, the physical perturbation may comprise exposure to different temperatures, pressures, flow rates, pHs, or gas concentrations.

In some embodiments, the chemical perturbation may comprise exposure to one or more therapeutic agents or a range of concentrations of therapeutic agents.

In some embodiments, two or more perturbations may be done sequentially and an additional round of combinatorial indexing may be done between each round of perturbation.

In specific embodiments, the proximity dependent probes and/or oligonucleotide-tagged protein binding molecules may be configured to detect one or more gene expression products in one or more cell pathways. Cell pathways may include, but are not necessarily limited to, cell development pathways, cancer signaling pathways, and immune response signaling pathways.

In some embodiments, the one or more perturbation comprises exposure to one or more physical perturbations, genetic perturbations, chemical perturbations, or a combination thereof. The one or more physical perturbations may comprise exposure to different temperatures, pressures, flow rates, pHs, growth media compositions, or gas concentrations. The one or more genetic perturbations may comprise gene knock-outs, gene knock-ins, transpositions, inversions, and/or one or more nucleotide insertions, deletions, or substitutions. The one or more chemical perturbations may comprise exposure to one or more therapeutic agents or a concentration range of therapeutic agents.

In some embodiments, two or more perturbations are done sequentially and an additional round of combinatorial indexing is done between each perturbation round.

In some embodiments, one or more proximity dependent probes and/or oligonucleotide-tagged protein binding molecules are configured to detect one or more gene expression products in one or more cell pathways.

In some embodiments, the one or more cell pathways comprise a cell development pathway, a cancer signaling pathway, or an immune response signaling pathway.

MOLECULAR ASSAY SYSTEMS AND KITS

In some aspects the invention provides a molecular assay system comprising a) a set of proximity dependent probes; and b) a set of primer pairs, wherein each primer pair comprises at least one barcoded primer.

In some embodiments, the proximity dependent probes are molecular inversion probes (MIPs), HyPR probes, padlock probes, or split-ligation probes, each probe further comprising a unique molecular identifier (UMI), as described elsewhere herein.

In some embodiments, the set of proximity dependent probes comprise proximity dependent probes for detecting and/or quantitating at least 5, at least 10, at least 20, at least 30, at least 40, at least 50, at least 60, at least 70, at least 80, at least 90, at least 100, at least 200, at least 300, at least 500, at least 1000, or at least 10,000 target RNAs.

In some embodiments, 2 to 100 proximity dependent probes are used per target RNA.

In some embodiments, the set of proximity dependent probes detect gene expression markers on one or more cell signaling pathways.

In some embodiments, the one or more cell signaling pathways comprises a cell development pathway, a cancer signaling pathway, or an immune response signaling pathway.

In some embodiments, the primer pairs amplify one or more genomic DNA loci and allow for genotyping in combination with targeted RNA detection and quantitation.

In some embodiments, the targeted genomic DNA loci include sites of somatic mutations that affect known processes such as proliferation or cancer development.

In some embodiments, the individual discrete volumes are droplets, wherein the kit further comprises reagents for droplet formation.

In some embodiments, the system may further comprise a means for sorting and/or encapsulating individual cells into droplets. The means for sorting and/or encapsulating individual cells may comprise a microfluidic device.

Microfluidic devices (for example, fabricated in polydimethylsiloxane), generate sub-nanoliter reverse emulsion droplets. These droplets are used to co-encapsulate proteins and/or nucleic acids with a barcoded bead as described herein. Each bead, for example, is uniquely barcoded so that each drop and its contents are distinguishable. The proteins and/or nucleic acids may come from any source known in the art, such as for example, those which come from a single cell, a pair of cells, a cellular lysate, or a solution. The cell is lysed as it is encapsulated in the droplet. To load single cells and barcoded beads into these droplets with Poisson statistics, 100,000 to 10 million such beads are needed to barcode ~10,000-100,000 cells.

In some embodiments, the particles may be encapsulated in droplets, such as microfluidic droplets. Those of ordinary skill in the art will be aware of techniques for encapsulating particles within microfluidic droplets; see, for example, U.S. Pat. Nos. 7,708,949, 8,337,778, 8,765,485, or Int. Pat. Appl. Pub. Nos. WO 2004/091763 and WO 2006/096571, each incorporated herein by reference. In some cases, the particles may be encapsulated at a density of less than 1 particle/droplet (and in some cases, much less than 1 particle/droplet) to ensure that most or all of the droplets have only zero or one particle present in them. In other cases, the particles may be encapsulated at a density of 1, 2, 3, 4, 5, or more particles per droplet, and the location of multiple particles per droplet computationally determined after sequencing based on the presence of identical unique molecular identifiers associated with multiple particle barcodes.

In some embodiments, the system may further comprise reagents for PCR amplification. In some embodiments, one or both barcoded primers comprise a set of discrete beads, wherein each bead contains a unique barcode.

Typically, a nucleic acid barcode is used to identify a target molecule and/or target nucleic acid as being from a particular discrete volume, having a particular physical property (for example, affinity, length, sequence, etc.), or having been subject to certain treatment conditions. Target molecule and/or target nucleic acid can be associated with multiple nucleic acid barcodes to provide information about all of these features (and more). Each member of a given population of UMIs, on the other hand, is typically associated with (for example, covalently bound to or a component of the same molecule as) individual members of a particular set of identical, specific (for example, discreet volume-, physical property-, or treatment condition-specific) nucleic acid barcodes. Thus, for example, each member of a set of origin-specific nucleic acid barcodes, or other nucleic acid identifier or connector oligonucleotide, having identical or matched barcode sequences, may be associated with (for example, covalently bound to or a component of the same molecule as) a distinct or different UMI. A nucleic acid barcode or UMI can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form.

In specific embodiments, at least one primer of a primer pair is delivered to an individual discrete volume on a bead. In specific embodiments, the individual discrete volumes are droplets.

In certain example embodiments, the invention provides oligonucleotide-labeled beads. In certain example embodiments, barcoded primers may be delivered to individual discrete volumes on hydrogel beads. Exemplary methods can be found in Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352): 661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In some embodiments, the discrete bead comprises hydrogel beads, magnetic beads, or other beads. In some embodiments, the discrete beads may be distributed randomly amongst the droplets together with cells so that each droplet has ~1 cell and ~1 bead with barcodes.

In other embodiments, the invention provides a molecular assay system comprising droplet forming reagents for formation of hydrogel based droplets that contain cells and/or primers with linkers that link the primer pairs to the hydrogel matrix upon droplet formation.

The droplet forming reagents may further comprise a linker molecule for linking nucleic acids to the hydrogel and/or a linker molecule for linking proteins to the hydrogel and/or primers with releasable linkers that link amplification primers to the hydrogel matrix upon droplet formation.

In some embodiments, the nucleic acid linking molecule may be LabelX and the protein linking molecule may be AcX, as described in the examples.

In some embodiments, the system may further comprise oligo-dT RT primers comprising a releasable linker that links the oligo-dT RT primers to the hydrogel.

In some embodiments, the system may further comprise a set of proximity dependent probes, as described elsewhere herein. The proximity dependent probes may be molecular inversion probes (MIPs), HyPR probes, padlock probes, or split-ligation probes, each probe further comprising a unique molecular identifier (UMI), as described herein.

In some embodiments, the set of proximity dependent probes may comprise proximity dependent probes for detecting and/or quantitating at least 1, at least 5, at least 10, at least 20, at least 30, at least 40, at least 50, at least 60, at least 70, at least 80, at least 90, at least 100, at least 200, at least 300, at least 500, at least 1000, or at least 10,000 target RNAs or DNAs. As described elsewhere herein, 10 to 100 proximity dependent probes may be used per target RNA and/or DNA.

In some embodiments, the system may further comprise one or more oligonucleotide tagged protein binding molecules, wherein the oligonucleotide on the oligonucleotide tagged protein binding molecules comprise a primer binding set for the primer pairs or a portion of the primer pairs.

In some embodiments, the set of proximity dependent probes and/or oligonucleotide tagged protein binding molecules may detect gene expression markers of one or more cell signaling pathways. The one or more cell signaling pathways may comprise a cell development pathway, a cancer signaling pathway, or an immune response signaling pathway.

In some embodiments, the system may further comprise fixing reagents to fix cells prior to encapsulation in hydrogel droplets.

In some embodiments, the system may further comprise cross-linking reversing agents to reverse cross-links formed in fixed cells.

In some embodiments, the system may further comprise combinatorial indexing reagents for adding barcode sequences to the one or more primer pairs linked to the hydrogel matrix.

In some embodiments, the system may further comprise barcoding adapters and reagents for ligating the barcoding adapters to target molecules to allow for direct barcoding of target molecules.

In some embodiments, the system may further comprise an exonuclease for converting dsDNA into ssDNA.

In some embodiments, the system may further comprise whole genome amplification regents, PCR amplification reagent, reverse transcription reagents, rolling circle amplification reagents, or a combination thereof.

In some embodiments, the system may further comprise a means for sorting and/or encapsulating individual cells in hydrogel droplets. As described elsewhere herein, the means for sorting and/or encapsulating individual cells in hydrogel droplets may comprise a microfluidic device.

As described elsewhere herein, the droplet reagents may comprise acrylamide/bisacrylamide, acrylamide/di-hydroxyethylenebisacrylamide, or acrylamide/N,N'-bis(acryloyl)cystamine. The ratio of acrylamide to bisacrylamide may range from 10:1 to 40:1. The percentage of acrylamide/bisacrylamide may range from 3% to 20%.

In some embodiments, the system may further comprise barcoded beads, wherein the barcoded beads comprise sets of primers that can be co-emulsified with the cell-containing hydrogels.

In one aspect, the invention provides molecular assay systems comprised in a kit. Such kits may include a set of proximity dependent probes and a set of primer pairs. Each primer pair may comprise at least one barcoded primer. The proximity dependent ligation probes may be MIPs, padlock probes, or split-ligation probes as described herein. Each probe may further comprise a UMI.

In some embodiments, the kit may include proximity dependent probes for detecting and/or quantitating at least 5, at least 10, at least 20, at least 30, at least 40, at least 50, at least 60, at least 70, at least 80, at least 90, at least 100, at least 200, at least 300, at least 500, at least 1000, or at least 10,000 target RNAs. Some embodiments may comprise 10 to 100 proximity dependent probes per target RNA as described herein. The set of proximity dependent probes may detect gene expression markers on one or more cell signaling pathways. Such cell signaling pathways may include, but are not necessarily limited to, cell development pathways, cancer signaling pathways, or immune response signaling pathways.

The primer pairs may amplify one or more genomic DNA loci and allow for genotyping in combination with targeted RNA detection and quantitation. In some embodiments, the individual discrete volumes may be droplets. In some embodiments, the kit may further comprise reagents for droplet formation. The system may further comprise a means for sorting and/or encapsulating individual cells into droplets. Such means for sorting and/or encapsulating individual cells may comprise a microfluidic device.

In some embodiments, the kit may include beads as described herein, and any of the reagents described herein.

Also envisioned within the scope of the invention are molecular assay systems comprising droplet forming reagents for formation of hydrogel based droplets and a set of primer pairs for detecting one or more molecules. The primer pairs may comprise a releasable linker that links the primer pairs to the hydrogel matrix upon droplet formation.

The droplet forming reagents may further comprise linker molecules for linking nucleic acids to the hydrogel and/or a linker molecule for linking proteins to the hydrogel. Nucleic acid linking molecules may include LabelX and protein linking molecules may include AcX. The system may further comprise oligo-dT RT primers comprising a releasable linker that links the oligo-dT RT primers to the hydrogel. The system may further comprise a set of proximity dependent ligation probes. The proximity dependent ligation probes may include, but are not necessarily limited to, molecular inversion probes (MIPs), padlock probes, or split-ligation probes, each probe further comprising a unique molecular identifier (UMI). The set of proximity dependent probes may comprise proximity dependent probes for detecting and/or quantitating at least 5, at least 10, at least 20, at least 30, at least 40, at least 50, at least 60, at least 70, at least 80, at least 90, at least 100, at least 200, at least 300, at least 500, at least 1000, or at least 10,000 target RNAs or DNAs as described herein. The system may use anywhere from 5 to 1000 proximity dependent probes per target RNA and/or DNA as described herein.

In some embodiments, the system may further comprise one or more oligonucleotide tagged protein binding molecules. The oligonucleotide may comprise a primer binding site for the primer pairs or a portion of the primer pairs. The set of proximity dependent probes and/or oligonucleotide tagged protein binding molecules may detect gene expression markers of one or more cell signaling pathways. The cell signaling pathway may comprise a cell development pathway, a cancer signaling pathway, or an immune response signaling pathway. The system may further comprise fixing reagents to fix cells prior to encapsulation in hydrogel droplets. The system may further comprise cross-linking reversing agents to reverse cross-links formed in fixed cells.

In some embodiments, the system may further comprise combinatorial indexing reagents for adding barcode sequences to the one or more primer pairs linked to the hydrogel matrix. The system may further comprise barcoding adapters and reagents for ligating the barcoding adapters to target molecules to allow for direct barcoding of target molecules. The system may further comprise an exonuclease for converting dsDNA into ssDNA. The system may further comprise whole genome amplification regents, PCR amplification reagent, reverse transcription reagents, rolling circle amplification reagents, or a combination thereof. A means for sorting or encapsulating individual cells in hydrogel droplets may also be provided. The means for sorting and/or encapsulating individual cells in hydrogel droplets may comprise a microfluidic device.

As described herein, the droplet reagents may comprise acrylamide/bisacrylamide, acrylamide/di-hydroxyethylenebisacrylamide, or acrylamide/N,N'-bis(acryloyl)cystamine. The ratio of acrylamide to bisacrylamide may range from 10:1 to 40:1. The percentage of acrylamide/bisacrylamide may range from 3% to 20%.

OTHER METHODS

Also envisioned within the scope of the invention are methods for determining the presence of molecules in single cells using combinations of methods and assays as described herein.

In specific embodiments, single cells may be fixed before encapsulation and crosslinks may be reversed after encapsulation.

Any standard fixation methods known in the art may be used. Fixation of cells or tissue may involve but is not necessarily limited to, the use of cross-linking agents, such as formaldehyde, and may involve embedding cells or tissue in a paraffin wax or polyacrylamide support matrix (Chung K, et al. Nature. 2013 May 16; 497(7449): 322-7). Standard methods for delivery of nucleic acid based probes to fixed cells may be used. Example methods for delivering to fixed cells may be found in U.S. Patent Application Publication No. 2017/0067096 A1, International Patent Application No. PCT/US2015/016788, and U.S. Patent Application no. 2016/0305856 A1, each of which is incorporated herein by reference.

The ligation dependent probes are maintained under conditions sufficient to allow hybridization. The ligation dependent probes are then ligated together. This may be done using any ligation technique commonly known in the art. Example standard ligation techniques may include, but are not necessarily limited to, ligation using SplintR, T4 DNA Ligase, T4 RNA ligase, or methods used in concatemer ligation assays, proximity ligation assays, and proximity extension assays such as those found in US 2016/0024572 A1 and PCT/US2014/028921.

In specific embodiments, 10 or more, preferably 50 or more ligation dependent probes are used. Specific embodiments comprise primer pairs for genotyping 10 or more, preferably 50 or more genomic loci.

In specific embodiments, the ligation dependent probes may be molecular inversion probes (MIPs), padlock probes, or split-ligation probes as described herein.

In specific embodiments, the individual discrete volumes may be emulsion droplets or separate wells.

In specific embodiments, single cells may be lysed in the oil emulsion droplets prior to polymerizing hydrogels. Other components of a biological or chemical reaction may include a cell lysis component in order to break open or lyse a cell for analysis of the materials therein. A cell lysis component may include, but is not limited to, a detergent, a salt as described above, such as NaCl, KCl, ammonium sulfate [(NH4)2SO4], or others. Detergents that may be appropriate for the invention may include Triton X-100, sodium dodecyl sulfate (SDS), CHAPS (3-[(3-cholamidopropyl)dimethylammonio]-1-propanesulfonate), ethyl trimethyl ammonium bromide, nonyl phenoxypolyethoxylethanol (NP-40). Concentrations of detergents may depend on the particular application, and may be specific to the reaction in some cases. Amplification reactions may include dNTPs and nucleic acid primers used at any concentration appropriate for the invention, such as including, but not limited to, a concentration of 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 mM, 2 mM, 3 mM, 4 mM, 5 mM, 6 mM, 7 mM, 8 mM, 9 mM, 10 mM, 20 mM, 30 mM, 40 mM, 50 mM, 60 mM, 70 mM, 80 mM, 90 mM, 100 mM, 150 mM, 200 mM, 250 mM, 300 mM, 350 mM, 400 mM, 450 mM, 500 mM, or the like. Likewise, a polymerase useful in accordance with the invention may be any specific or general polymerase known in the art and useful or the invention, including Taq polymerase, Q5 polymerase, or the like.

Specific embodiments may include delivering ATAC-seq reagents comprising a transposase loaded with adaptor sequences comprising a UPS and a reverse priming site. In certain embodiments, tagmentation is used to introduce adaptor sequences to genomic DNA. The term "tagmentation" refers to a step in the Assay for Transposase Accessible Chromatin using sequencing (ATAC-seq) as described. (See, Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature methods 2013; 10 (12): 1213-1218). Specifically, a hyperactive Tn5 transposase loaded in vitro with adapters for high-throughput DNA sequencing, can simultaneously fragment and tag a genome with sequencing adapters. In one embodiment, the adapters are compatible with the methods described herein.

In some embodiments, chromatin accessibility may be determined using a single cell ATAC-seq assay (see Cusanovich et al. Science 348(6237):910-914; 2015). ATAC-seq offers genome-wide chromatin accessibility of regulatory elements, transcription factor binding and nucleosome positioning. The term "tagmentation" refers to a step in the Assay for Transposase Accessible Chromatin using sequencing (ATAC-seq) as described. (See, Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature methods 2013; 10 (12): 1213-1218). Specifically, a hyperactive Tn5 transposase loaded in vitro with adapters for high-throughput DNA sequencing, can simultaneously fragment and tag a genome with sequencing adapters. In one embodiment the adapters are compatible with the methods described herein.

In certain embodiments, tagmentation is used to introduce adaptor sequences to genomic DNA in regions of accessible chromatin (e.g., between individual nucleosomes) (see, e.g., US20160208323A1; US20160060691A1; WO2017156336A1; and Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237):910-4. doi: 10.1126/science.aab1601. Epub 2015 May 7). In certain embodiments, tagmentation is applied to bulk samples or to single cells in discrete volumes.

In some embodiments, the method further comprises exchanging reagents within the hydrogel to provide a new set of reagents for conducting one or more additional assays, such as for example, ATAC-seq, or Whole Genome Sequencing (WGS), as described herein. In some embodiments, chromatin accessibility may be determined using a single cell ATAC-seq assay as described above (see Cusanovich et al. Science 348(6237):910-914; 2015).

In certain embodiments, the present invention can be used in conjunction with cellular recording assays (see, e.g., International publication WO2016205728A1; and Tang, W. and Liu, D. R., Rewriteable Multi-Event Analog Recording in Bacterial and Mammalian Cells, Science 15 Feb. 2018: eaap8992, DOI: 10.1126/science.aap8992). In certain embodiments, cellular events are recorded by editing a reporter sequence and the present invention may be used to detect the edited reporter sequence to determine if the cellular event occurred in a single cell. In certain embodiments, the cellular event can be linked to changes in gene expression by further detecting expression of genes using the methods described herein.

In certain embodiments, the hydrogel may further comprise oligonucleotide-tagged protein binding molecules. The oligonucleotide tag may be amplified using one or more primer pairs in the hydrogel matrix configured to bind to a primer recognition site on the oligonucleotide tag to generate barcoded oligonucleotide tag amplicons. Target protein abundance may be identified and/or quantified based at least in part on sequencing the barcoded oligonucleotide tag amplicons. Additional embodiments may comprise suspending the hydrogels in an additional molecular assay mixture and conducting one or more additional molecular assays. Suitable molecular assays include, but are not necessarily limited to, chromatin accessibility assays. Suitable chromatin accessibility assays may include ATAC-seq. In alternative embodiments, the chromatin accessibility assay may include, but is not necessarily limited to, BS-Seq Bisulfite-seq WGBS, EpiGnome HELP-Seq, PBAT, BSPP, RRBS scRRBS, BSAS, Methyl-Seq MRE-Seq, EpiRADseq, T-WGBS, JBP1-seq, Aba-seq, TAmC-Seq, fC-Seal, fC-CET, CAB-Seq, oxBS-Seq, RedBS-Seq caMAB-seq, fCAB-Seq, MAB-seq, RRMAB-seq, TAB-Seq, MIRA, MeDIP-Seq DIP-Seq, hMeDIP-Seq, MBDCap-Seq Methyl-Cap-seq MBD-Seq MiGS, and BisChIP-Seq ChIP-BS-seq. Additional suitable molecular assays may include epigenetic modification assays, as described in for example, but not necessarily limited to, Butcher et al. (Methods 52(3):223-231 (2010)) and Karimi et al. (Exp Cell Res 312(11):1989-1995 (2006)). Another suitable molecular assay includes a chromatin folding assay, such as including, but not necessarily limited to, Hi-C or Hi-C++.

In some embodiments, the protein binding molecules may also be barcoded using combinatorial methods as described herein.

Other methods for genotyping single cells may also involve quantitating RNA in single cells. Such assays may involve preparing hydrogel droplets as previously described and resuspending the hydrogels in a reverse transcription (RT) mix. The hydrogels may then be segregated into individual discrete volumes and the second barcoded primers comprising oligo-dT sequences may be released from the hydrogel via the second cleavable linker. The cDNA may be eluted from the hydrogels and amplicons may be generated for sequencing. Genotyping may then be performed on the hydrogel droplets as previously described and the resulting amplicons may be sequenced.

Methods for targeted RNA quantification in single cells may involve preparing hydrogel droplets as described herein and delivering one or more ligation dependent probes to the hydrogel droplets and allowing hybridization, wherein each ligation dependent probe comprises a UPS, a reverse priming site, a UMI, and a target binding region configured to hybridize to adjacent sites on a target RNA of interest. The hydrogels may be resuspended in a ligase mix comprising an RNA-templated DNA ligase, wherein a circular DNA is generated when the target RNA of interest is bound by a probe. The hydrogels may be resuspended in a PCR mix comprising primers specific to the reverse priming site, and the hydrogels may be segregated into individual discrete volumes as described herein. The barcoded primers may be released from the hydrogel via the cleavable linker, and PCR may be performed in the individual discrete volumes, generating cell-barcoded amplicons. The resulting amplicons may then be sequenced.

Other methods for targeted RNA quantification and genotyping in single cells may involve preparing hydrogel droplets as described herein, delivering one or more ligation dependent probes to the hydrogel droplets, wherein each ligation dependent probe comprises a UPS, a reverse priming site, a UMI, and a target binding region configured to hybridize to adjacent sites on a target RNA of interest. One or more ligation dependent probes may be delivered to the hydrogel droplets, wherein each ligation dependent probe comprises a UPS, a reverse priming site, and a target binding region configured to hybridize to adjacent sites on a target DNA of interest, optionally a UMI. The probes are then allowed to hybridize, and the hydrogels may be resuspended in a ligase mix comprising an RNA-templated DNA ligase, wherein a circular DNA is generated when the target RNA of interest is bound by a probe. The hydrogels may be resuspended in a polymerase mix and the 3' probe end may be extended using a polymerase lacking strand-displacement activity as described in the examples. The 3' end may be ligated to the 5' end, wherein a circular DNA comprising the target DNA of interest is generated. The hydrogels may be resuspended in a PCR mix comprising primers specific to the reverse priming site. The hydrogels may be segregated into individual discrete volumes, the barcoded primers may be released from the hydrogel via the cleavable linker, and PCR may be performed in the individual discrete volumes, generating cell-barcoded amplicons. The resulting amplicons may then be sequenced as described herein.

In some embodiments, each individual discrete volume may further comprise DNA-tagged protein-binding molecules for quantifying target protein abundance.

Methods for protein quantification in single cells may comprise preparing hydrogel droplets as described herein, and delivering one or more oligonucleotide linked antibodies to the hydrogel droplets. The antibodies may be allowed to bind to proteins. Each oligonucleotide linked antibody may comprise a UPS, a reverse priming site, a UMI, and an antibody identifying barcode.

In some embodiments, hydrogels may be washed to remove unbound antibodies and may then be resuspended in a PCR mix comprising primers specific to the reverse priming site. The hydrogels may be segregated into individual discrete volumes, the barcoded primers may be released from the hydrogel via the cleavable linker, and PCR may be performed in the individual discrete volumes, generating cell-barcoded amplicons as described herein. The resulting amplicons may then be sequenced.

In some embodiments, segregating the hydrogels into individual discrete volumes involves transferring the hydrogels to separate wells or transferring the hydrogels to oil emulsions as described herein. In some embodiments, RNA, copy number variation (CNV), and/or protein may be quantified by counting UMIs.

In specific embodiments, genotyping, RNA quantification, and/or protein quantification may be done in single cells using a combination of any of the steps and methods described herein.

EXAMPLES

Example 1—Development of Hydrogel Emulsion Technologies to Encapsulate Millions of Individual Single Cells in a Manner that Enables Sequential Enzymatic Reactions We have developed a new hydrogel droplet-based platform for single-cell analyses ("Cell-in-Gel platform") that is suitable for simultaneous measurements of RNA expression, DNA genotype, and other molecular characterizations. This approach builds on our recent work to develop Expansion Microscopy (ExM), in which an entire tissue is encapsulated in a large hydrogel and physically expanded for subsequent imaging. In our new single-cell approach, we encapsulate single cells in acrylamide hydrogel droplets using a microfluidic device, such that the cellular contents of a single cell—including RNA, DNA, and/or protein—are contained within one droplet (FIG. 1). We covalently couple nucleic acids and proteins to the polyacrylamide hydrogel using various small molecule anchoring approaches we have previously developed. This facilitates easy reagent and buffer changes and allows molecular biology steps to be performed in a standard Eppendorf test tube on millions of cells in parallel, while retaining each cell's contents in a compartmentalized hydrogel droplet.

We built a simple microfluidic droplet maker that can encapsulate ~1,000,000 fixed cells in hydrogel droplets in <1 hour, with greater speeds possible by reducing the size of the droplets. We have generated acrylamide hydrogels incorporating modified photocleavable primers for split-and-pool barcoding using existing protocols. Furthermore, we have encapsulated cells by co-flowing fixed cells in the acrylamide monomer solution (FIG. 1). We have shown that hydrogels can be emulsified through a simple vortexing step and these emulsions are stable for various molecular biology protocols including PCR. Finally, we have developed compatible protocols for sensitive multiplexed detection of RNA and DNA in hydrogel droplets, enabling simultaneous readouts of RNA and DNA from single cells.

Example 2—Targeted DNA Genotyping by PCR in Cell-in-Gel Platform

Figure 2:
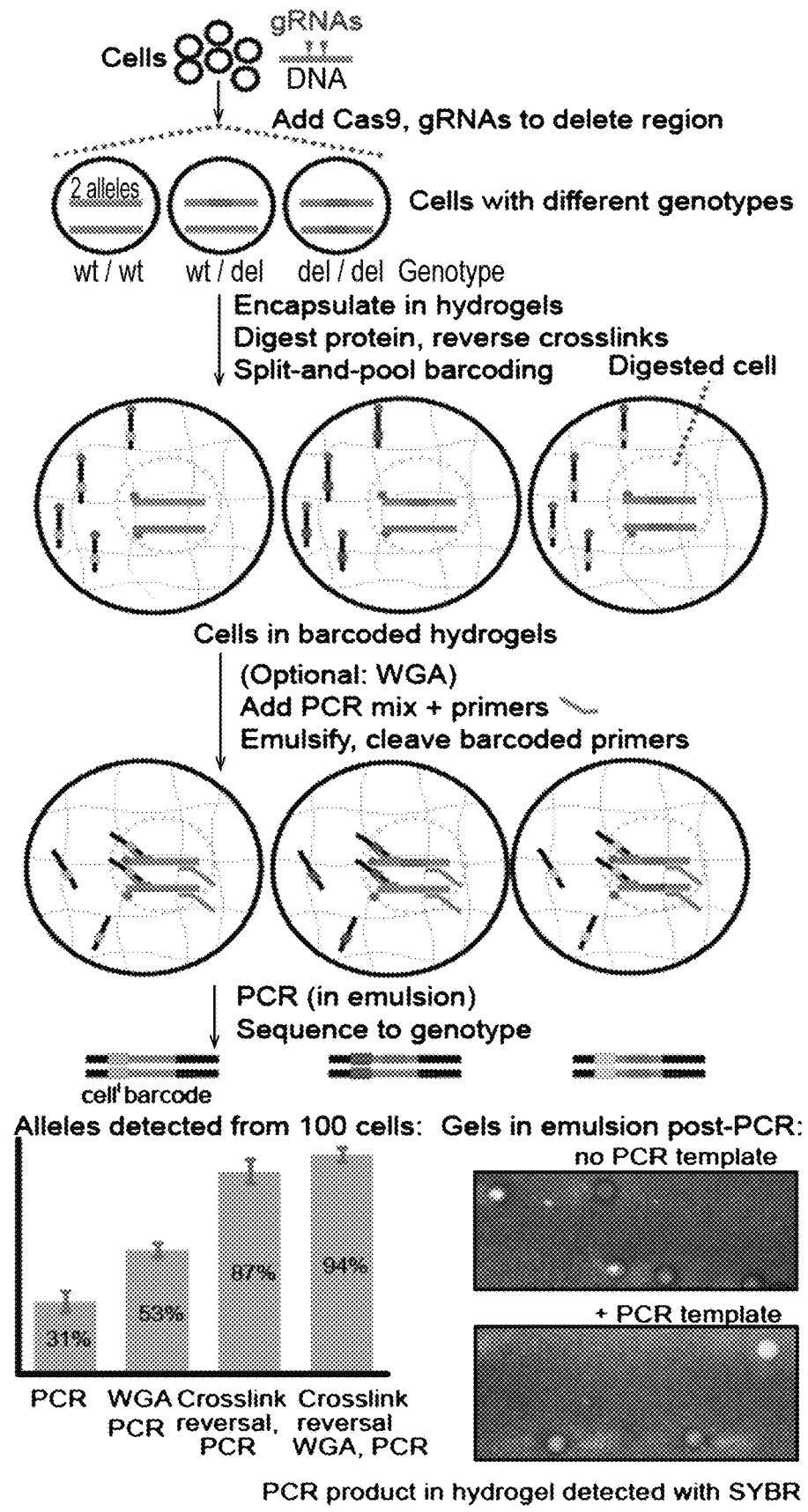
FIG. 2—illustrates single cell genotyping in the Cell-in-Gel platform. The top schematic shows crosslink reversal in hydrogel encapsulated cells followed by barcoded PCR. The graph shows high allelic detection efficiency following crosslink reversal in hydrogel droplets. Bottom right shows that barcoded PCR can be performed on hydrogels in emulsion.

We have demonstrated that our Cell-In-Gel platform allows a series of molecular biology steps that dramatically improve detection of single-copy loci (FIG. 2). Specifically, we encapsulate cells in hydrogels as described in Example 1. Next, we reverse formaldehyde crosslinks using detergent, proteinase K and heat treatment, eliminating steric blocks that hinder PCR, and perform split-and-pool ligation to generate barcoded PCR primers. We perform whole-genome amplification (WGA) to further improve detection efficiency. Next, we resuspend barcoded hydrogels in PCR mix containing primers targeted the DNA site(s) of interest, transfer the hydrogels into an oil emulsion, release the barcoded primers from the hydrogel via a photocleavable linker, and perform PCR in droplets to generate cell-barcoded DNA amplicons. Finally, we break the oil emulsion, perform a second round of PCR to add sequencing adapters, and sequence the DNA amplicons to identify the precise genotype of each allele in single cells. In preliminary results, we have optimized this protocol to achieve up to 94% allelic detection of a single-copy, randomly barcoded locus that we have engineered for optimization of detection efficiency in bulk acrylamide gels (FIG. 2), indicating that this approach will detect both alleles in ~88% of single cells. As WGA may interfere with the RNA readout steps described below, we will further optimize this protocol in the context of combining DNA and RNA readouts, using the single-copy locus and known SNPs in our cell line to evaluate allelic detection efficiency. Even without WGA, our preliminary experiments indicate that the Cell-In-Gel platform should enable ~87% detection efficiency of single alleles and thus reading out both alleles in >75% of single cells (FIG. 2). We will also optimize split-and-pool primer concentration and ligation conditions to generate barcoded primers for readouts of millions of cells, using 4 rounds of 96 barcodes each.

Example 3—Multiplexed DNA Detection Using Molecular Inversion Probes (MIPs)

To enable pooled screens involving genome editing at multiple loci in the same experiment, we will extend our DNA genotyping strategy to enable multiplexed DNA detection of multiple sites in the same single cells. We will test two strategies. (i) We will use multiplexed PCR to simultaneously amplify 2-20 regions in parallel. (ii) Because multiplexed PCR is limited in scale due to the potential for primer crosstalk, we will also optimize a protocol to apply DNA-targeted molecular inversion probes (MIPs) to read out multiple (up to 100) DNA regions in parallel. In this MIP approach, single-stranded DNA probes are designed such that the ends of the probe hybridize to adjacent sites on a DNA target. Following annealing of the probe ends, the 3' probe end of the probe is extended using a polymerase lacking strand-displacement activity and is ligated to the 5' probe end to form circular DNA. Circularized products are detected and amplified by PCR across the ligation junction followed by high throughput sequencing. Because hybridization of MIPs requires ssDNA templates (as opposed to genomic dsDNA), we will first perform WGA and treat with the Lambda ssDNA exonuclease, which will digest a single strand from dsDNA, leaving behind ssDNA that is amenable to hybridization. Following WGA and exonuclease digestion, DNA-targeted MIPs will be applied, extended, and ligated, followed by barcoded PCR in droplet emulsion as described above.

Example 4—Whole-Transcriptome RNA Sequencing

Figure 3:
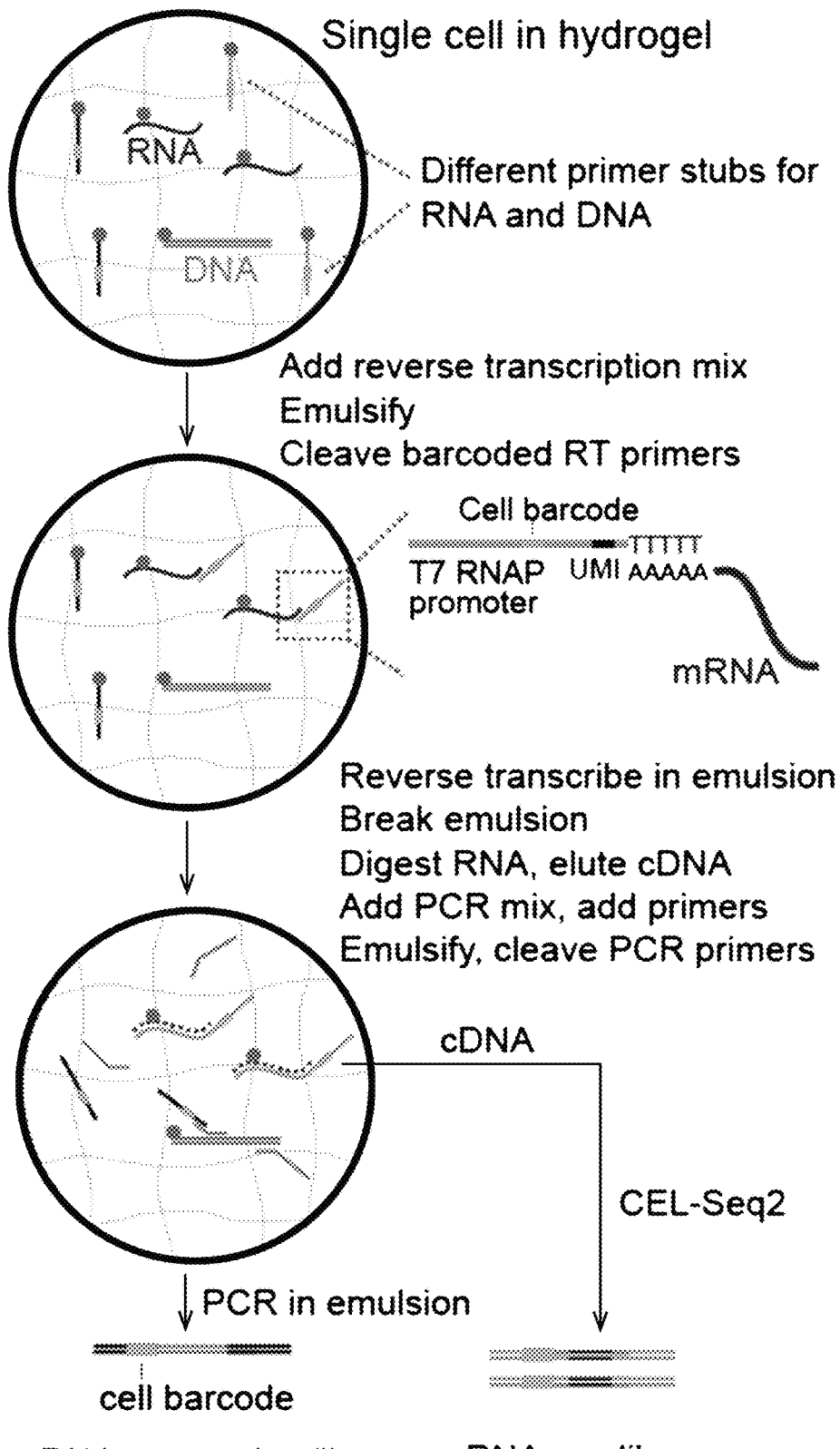
FIG. 3—Schematic outlining single cell genotyping combined with scRNAseq in the Cell-in-Gel platform.

We will combine single cell RNA-seq (scRNA-Seq) with single-cell DNA genotyping (scGenotyping) by making small changes to the In-Drop single-cell RNA-seq protocol to adapt it to our Cell-In-Gel format. In the In-Drop protocol, single-cell resolution is achieved by performing reverse transcription (RT) in droplets with barcoded oligo-dT primers, followed by signal amplification using T7 in vitro transcription. To combine this strategy with simultaneous DNA genotyping, we will generate hydrogels containing barcoded primers for genomic DNA amplification as well as barcoded oligo-dT primers; this will be accomplished by incorporating two different primer hybridization sites during hydrogel formation (one to assemble a RT primer with a photo-cleavable linker and one to assemble a primer for genomic DNA PCR with a uracil-DNA glycosylase (UDG)-cleavable linker), and using different "sticky-end" ligation overhangs to add barcodes and primer ends during the split-and-pool primer construction (FIG. 3). Following barcoded primer formation, we will resuspend barcoded hydrogels in RT mix, emulsify, and release the RT primers. Following RT, we will break the emulsion, digest RNA, and elute the cDNA from the hydrogels for further processing using the CEL-Seq2 protocol, starting with T7 transcription and amplification. Following cDNA elution, we will transfer hydrogels to emulsion, release the barcoded PCR primers, and perform the genomic DNA PCR as above. Because the cDNA is reverse transcribed and/or DNA is amplified using primers with identical cell barcodes, we will be able to match the RNA and DNA readouts from the same single cells. RNA will be quantified through UMIs in the RT primer, as previously described. We will optimize strategies for orthogonal cleavable primer linkers (e.g., RNase-, UDG-, or restriction-enzyme-cleavable); RT conditions for hydrogel emulsions (buffers and primer concentration); and cDNA elution (e.g., by electrophoresis, or by performing the first T7 amplification step of CEL-Seq2 in the hydrogels). We will quantify overall efficiency by comparing to standard In-Drop scRNA-seq and smFISH experiments for a panel of transcripts in the same cell line.

Example 5—Targeted RNA Quantification Using MIPs

Figure 4:
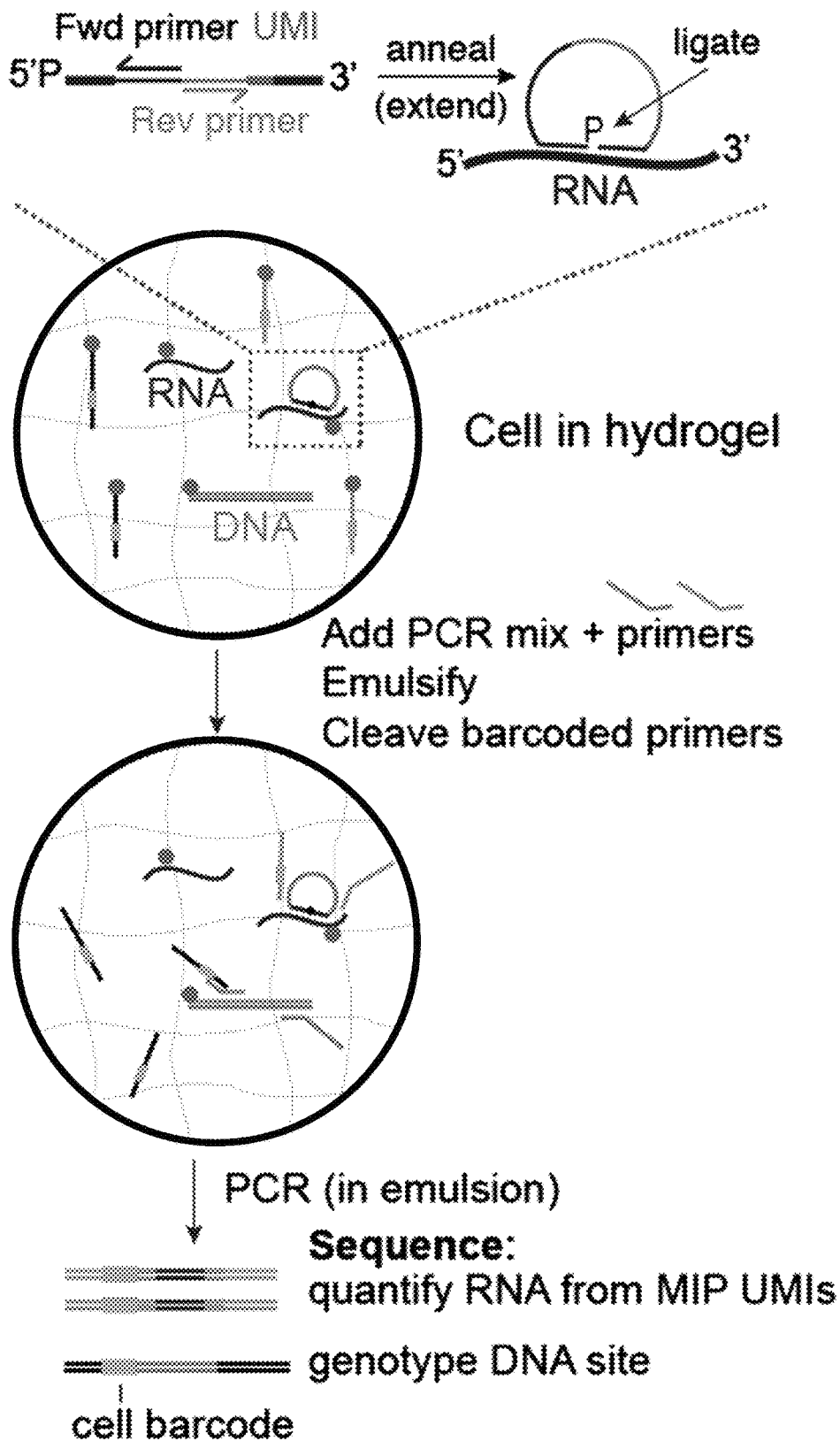
FIG. 4—Single cell genotyping combined with multiplexed MIP quantification of RNA in the Cell-in-Gel platform.

To complement the whole-transcriptome sequencing approach, we will develop a targeted RNA quantification approach that will enable (i) higher capture efficiency of individual transcripts compared to whole-transcriptome scRNA-seq, which is estimated to be only ~10%; (ii) customizable capture to reduce sequencing costs and increase cell throughput; (iii) allele-specific readouts of RNA expression; (iv) and capability to quantify non-polyadenylated RNAs. To read out RNA expression in a multiplexed, targeted fashion, we will use a novel technique we recently developed in which RNA transcripts are directly detected with molecular inversion probes (MIPs) (FIG. 4). While MIPs are frequently used to detect and/or sequence DNA or cDNA, their utility for direct RNA detection has been limited by the lack of an efficient RNA-templated DNA ligase. We have shown that we can dramatically improve direct RNA detection by using a recently discovered RNA-templated DNA ligase and applying 10-30 MIPs per mRNA, yielding comparable efficiency for detecting single RNA molecules as compared to single-molecule FISH (FIG. 4). This method is compatible with highly multiplexed measurements (up to thousands of mRNA targets), and complex probe sets can be generated at low cost from massively parallel oligonucleotide array synthesis. We have shown that this RNA MIP approach enables multiplexed in situ sequencing in combination with Expansion Microscopy (FIG. 5); these preliminary data demonstrate the robustness of the MIP detection approach and motivate its use in our droplet-based single-cell platform.

We will optimize and adapt this RNA MIP approach in combination with DNA genotyping in our Cell-In-Gel platform. Specifically, we will (i) encapsulate cells in barcoded hydrogels as described above; (ii) anneal and ligate MIPs; (iii) transfer hydrogels to oil emulsions, release primers via the photocleavable linker, and perform PCR with barcoded primers to simultaneously amplify the MIPs and genomic region(s) of interest (FIG. 4). We will then sequence the resulting cell-barcoded amplicons to read out the genotype of each single cell and simultaneously quantify gene expression by counting unique molecular identifiers (UMIs) contained in the MIPs. We expect that quantification through this approach will provide linear relative quantification of transcript levels across many orders of magnitude of expression levels, as reported by previous cDNA-targeted MIP studies. To verify this, we will compare MIP measurements after spiking in known quantities of the ERCC standard RNA, as well as comparing MIP measurements to relative quantification in bulk RNA-seq from the same populations of cells.

Example 6—Allele-Specific RNA MIPs

We will also extend this method to conduct allele-specific analysis of RNA expression, which can be a critical tool for establishing a cis-acting role of lncRNAs or other regulatory elements. While existing scRNA-seq protocols sequence only the 3' ends of transcripts (which may or may not contain SNPs), the MIPs approach will allow allele-specific analysis of polymorphic sites at any location in the transcript. We will explore two approaches for allele-specific detection with MIPs: (i) We will design probes with the 5' nucleotide directly overlapping the SNP. After MIP hybridization, only the correctly matching MIP will successfully ligate (see FIG. 5). (ii) We will design probes such that the two hybridization regions of the MIP flank the SNP. Following annealing, we will extend the MIP through reverse transcription and then continue with ligation, as has been previously done with DNA-targeted MIPs. This approach will allow for more flexible probe design because the hybridization regions do not have to directly overlap the SNP. We will validate this approach at scale by quantifying allele-specific expression in hybrid 129/Castaneus mESCs, a cell line in which we have previously performed extensive allele-specific RNA-sequencing studies.

Example 7—Approaches for Studying Very Low-Abundance Transcripts

Figure 5:
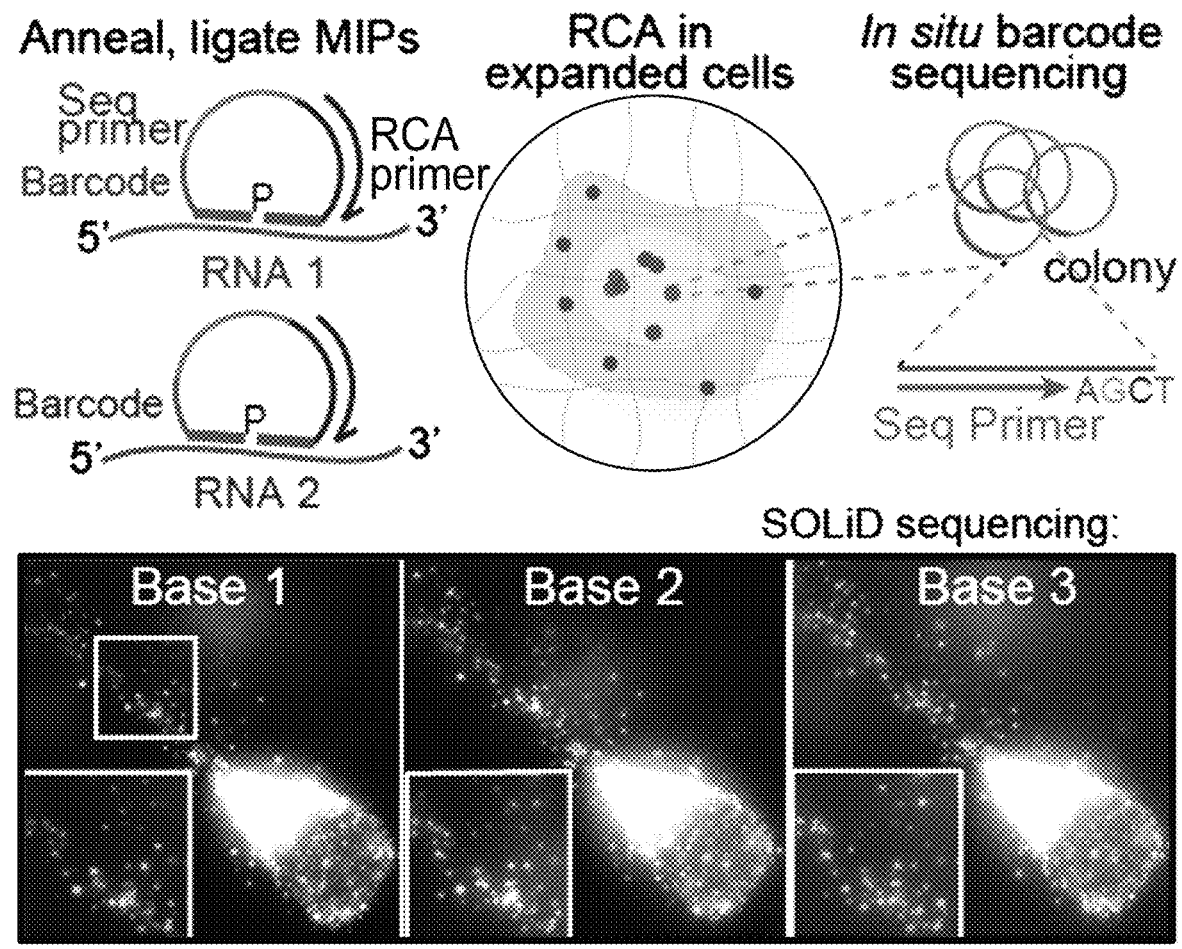
FIG. 5—In situ MIP readout via rolling circle amplification and subsequent fluorescent sequencing. Each set of MIPs for a given RNA transcript is given a unique sequence barcode which can be read out via sequencing by ligation (SOLiD), this enables 4^N multiplexing of transcripts where N is the number of sequencing bases (3 bases shown here). Bottom, allele specific in situ detection of SNP variants via MIPs.
Figure 5:
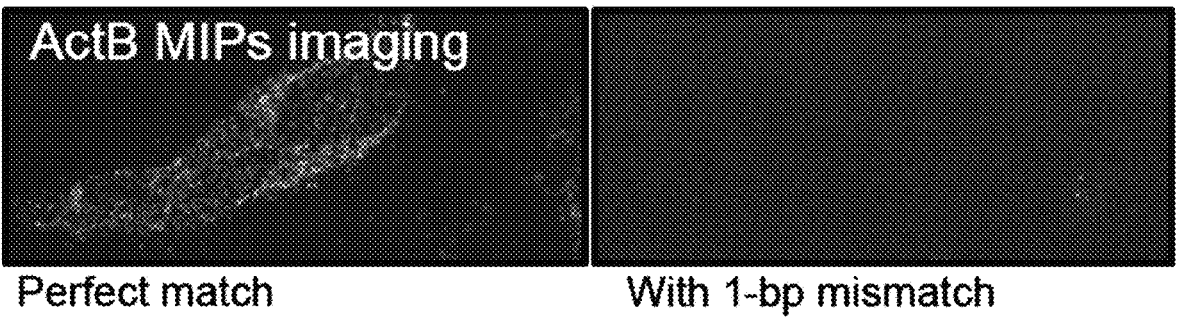
Figure 6:
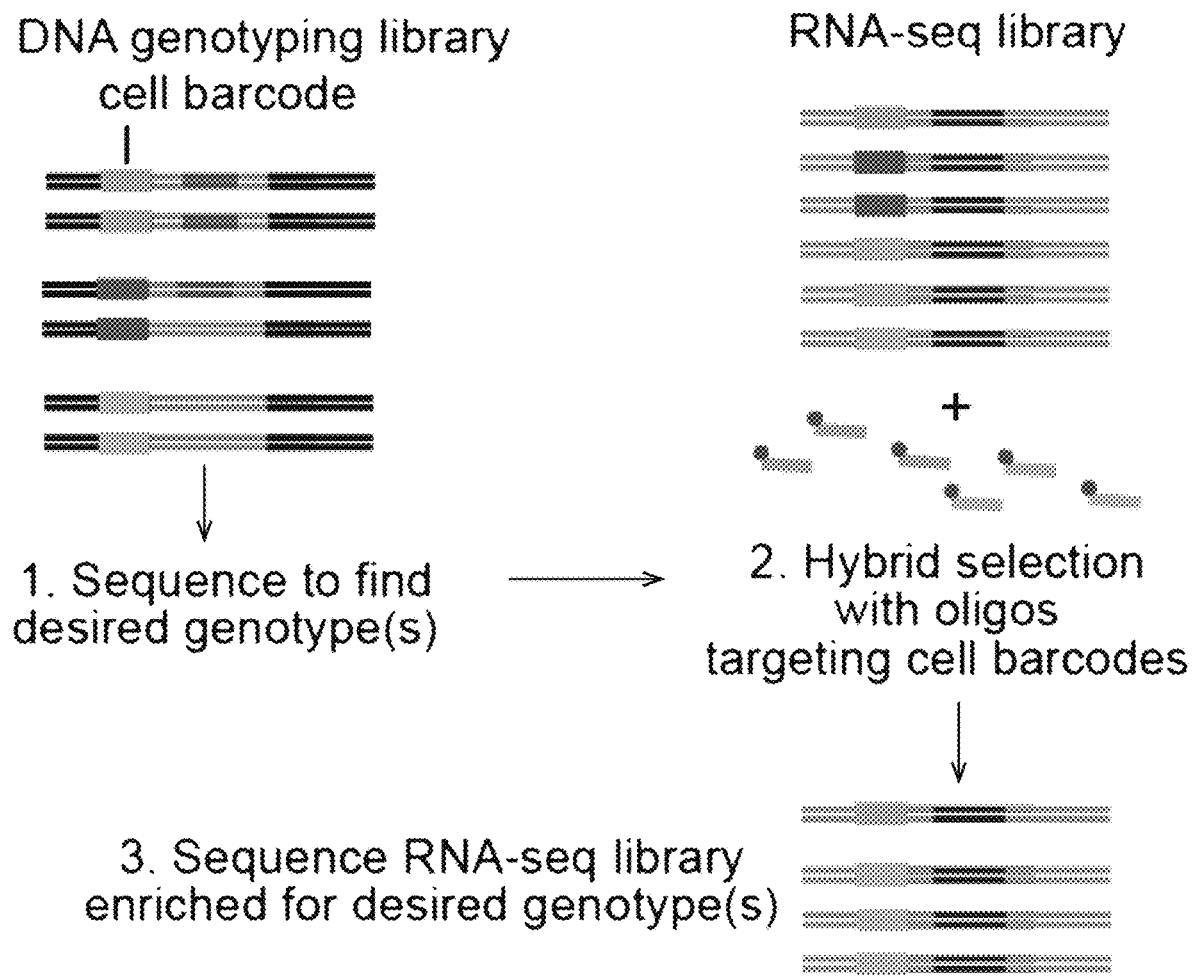
FIG. 6—A schematic of the strategy for selecting RNA for scRNA-Seq from cells that contain genotypes of interest.

One important criterion is that our genetic perturbation approach must work even for low-abundance RNAs, because many lncRNAs are estimated to be present at only 1-2 copies per cell. One key advantage of our genetic approach is that, because we measure the genotype (for example of deleting the promoter) in each cell, we can verify in aggregate across many single cells that lncRNA expression is lost in cells with homozygous deletions, and therefore do not need to reliably detect the lncRNA itself in every cell in order to infer the effects of the genetic perturbation. Nonetheless, high sensitivity for target lncRNAs will provide additional confidence in the findings. Accordingly, to study certain lncRNAs of very low expression, we will optimize the RNA MIPs approach to achieve even higher sensitivity by (i) increasing the number of unique MIPs per gene (up to 100) and by (ii) performing rolling circle amplification (RCA) following MIP ligation to amplify the signal resulting from each successful ligation event (FIG. 5). To validate and calibrate these methods, we measure the absolute copy-numbers of low-abundance lncRNAs of interest using sequential single-molecule RNA FISH (seqFISH), which we have shown can achieve close to 100% per molecule efficiency. seqFISH builds upon smFISH by performing sequential probe hybridizations on the mRNAs in fixed cells to impart a unique pre-defined temporal sequence of colors, generating an in situ mRNA barcode. The multiplex capacity scales as $F^N$, where F is the number of fluorophores and N is the number of rounds of hybridization. The data obtained with this method is highly quantitative and can measure low copy number transcripts with absolute quantitation (FIG. 6). seqFISH can be used to study up to 100,000 single cells and several hundred genes simultaneously. We will apply this method to quantify the copy-number and cell-to-cell variance of many low-abundance lncRNAs of interest in a multiplexed format, which will help us to quantify and optimize the efficiency of our RNA MIPs approach for low-abundance transcripts.

Example 8—Promoter Deletions to Identify lncRNA Loci that Regulate Gene Expression The first step of the 1-2-3 Punch method is to delete the promoter of the lncRNA. To do so, we will transfect or transduce a population of cells with vectors expressing Cas9 and two sgRNAs flanking the promoter of a lncRNA of interest (~1 kb total deletion) and profile this population of cells 5 days later using the Cell-In-Gel DNA Genotyping+ whole transcriptome scRNA-seq or a reduced representation of the transcriptome using targeted RNA MIPs. To identify the subset of cells that have heterozygous or homozygous insertions at a target locus, we will perform the DNA genotyping step using two primer pairs encompassing the cut sites on either end, which will form a PCR amplicon spanning the cut sites if the deletion is successful. High-throughput sequencing of these three amplicons can distinguish wild-type, homozygous knockout, and heterozygous knockout clones. Cells with homozygous deletions will be distinguished from heterozygous deletions where we sequenced one allele and missed the other allele by reading out the sequence of the deletion junction, which varies due to random indels that occur during deletion repair. In our previous study, we typically obtained homozygous deletions in ~10-25% of cells (depending on the specific gRNA pair and genomic locus). Because we expect to read out both alleles in >75% of cells (see above), sufficient coverage (~300 cells with homozygous deletions) can be obtained by profiling ~1,200-4,000 single cells for each lncRNA, with the number of cells decreasing as the efficiency of genome editing strategies improve.

We will examine RNA expression in single cells containing a desired genotype (e.g., homozygous knockout of the promoter) compared to wild-type cells in the same mixed population, providing an internal control for biological variability and allowing readouts of multiple independent edited clones in the same experiment. Power analyses indicate that we will need to examine ~300 single cells carrying homozygous knockouts per locus to detect global pathway-level changes in gene expression. For application to individual loci, using whole-transcriptome sequencing is feasible; for high-throughput applications for 100 loci, we will use the RNA MIPs strategy to measure a reduced representation of the transcriptome and thereby reduce sequencing cost. We will analyze these data using linear models to account for cell state (e.g., stage in the cell cycle or cryptic population structure), and determine which lncRNA knockouts result in significant changes in gene expression relative to wild-type, unedited cells in the same experiment.

Example 9—Identify and Enrich for Cells with Desired Genotypes

Figure 7:
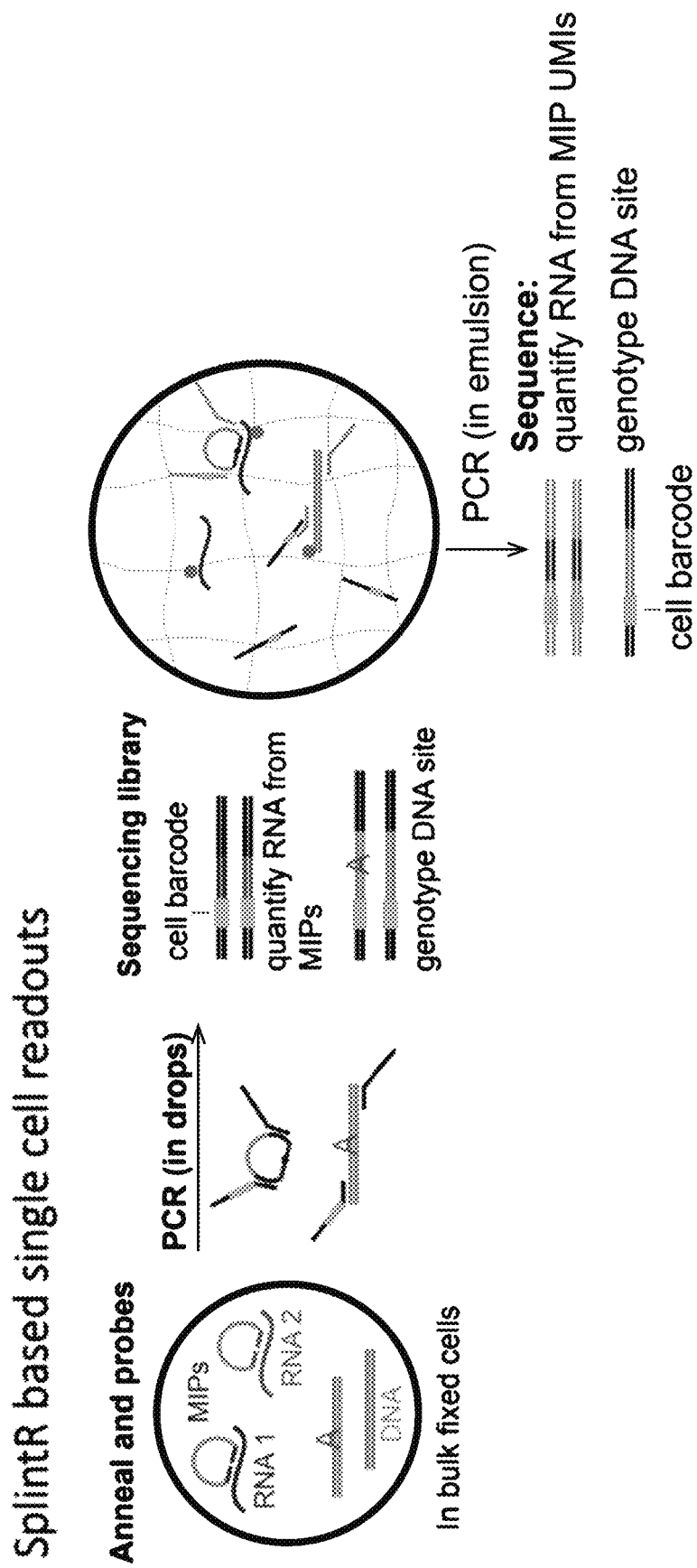
FIG. 7—Schematic demonstrating simultaneous quantification of RNA using MIPs and DNA genotyping by PCR.
Figure 8:
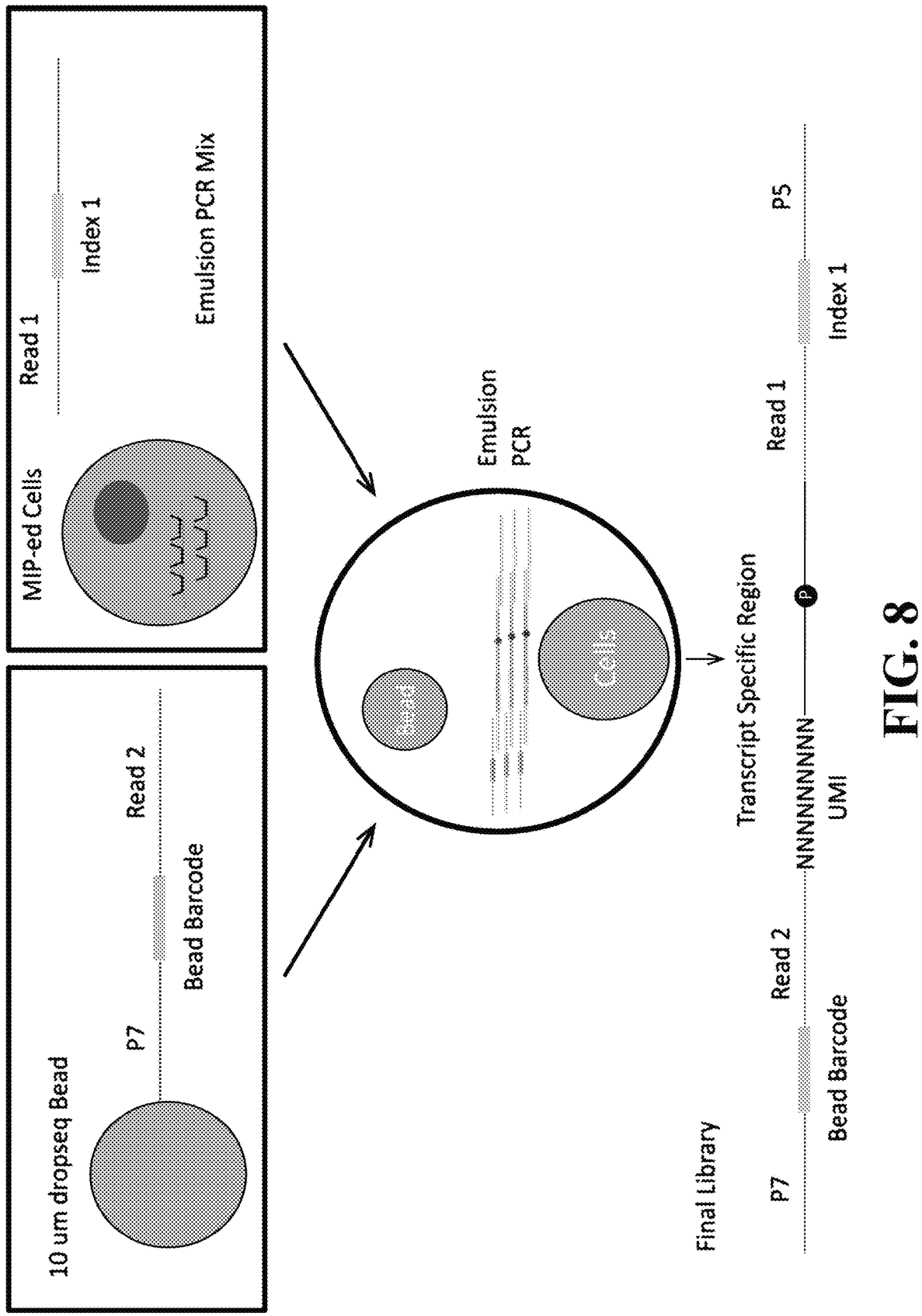
FIG. 8—Schematic of strategy to deliver barcoded primers into discrete volumes using a solid bead ("10 um dropseq"), and the resulting PCR amplicons obtained after amplifying MIPs.
Figure 9:
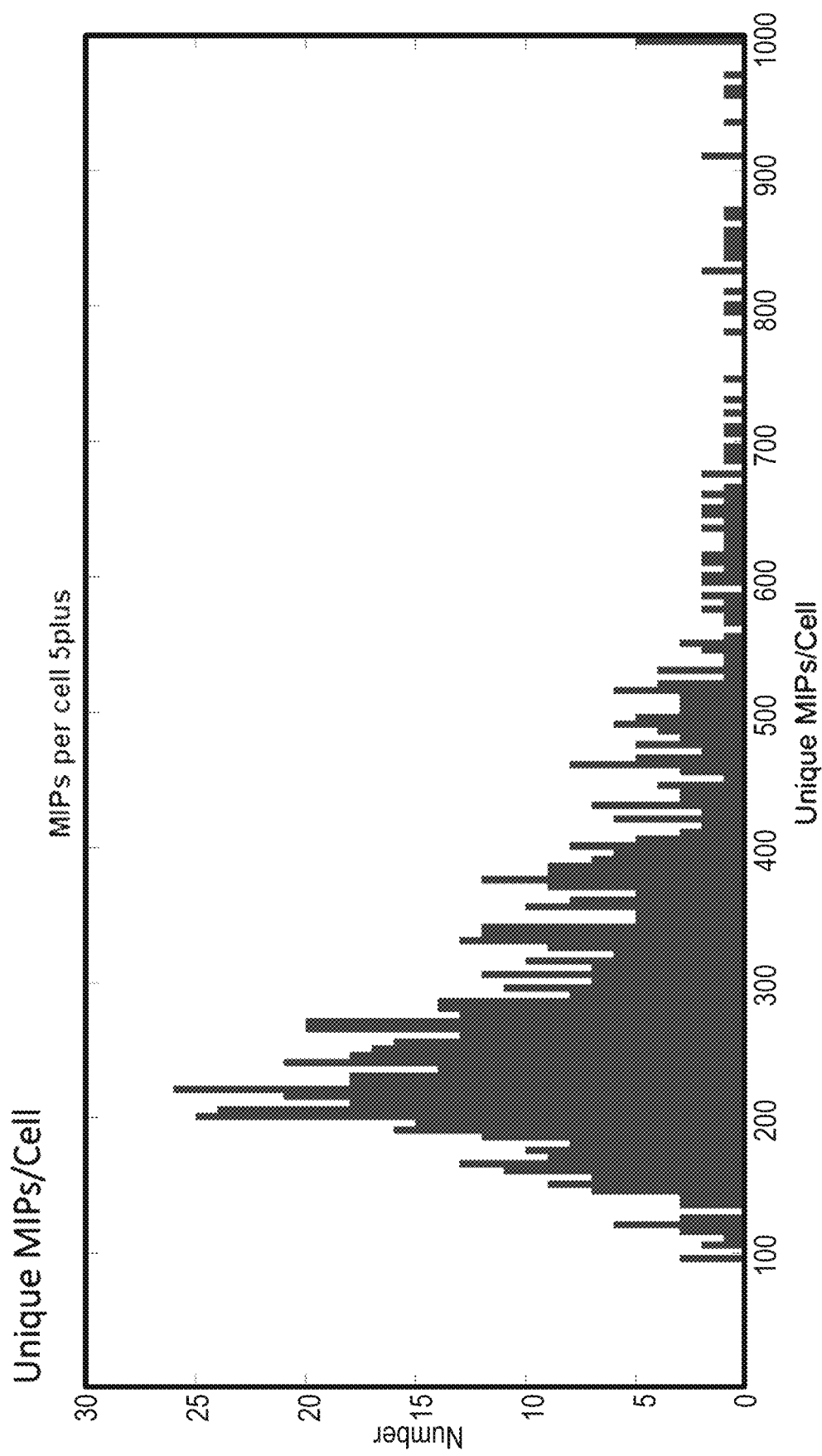
FIG. 9—Histogram of unique molecular identifiers (UMIs) observed per cell barcode, based on sequencing data generated after applying a mixed pool of ligation dependent probes targeting 12 genes (8 probe pairs per gene) to formalin-fixed K562 cells, and amplifying the cells using primers delivered by solid beads in a droplet-based PCR.
Figure 10:
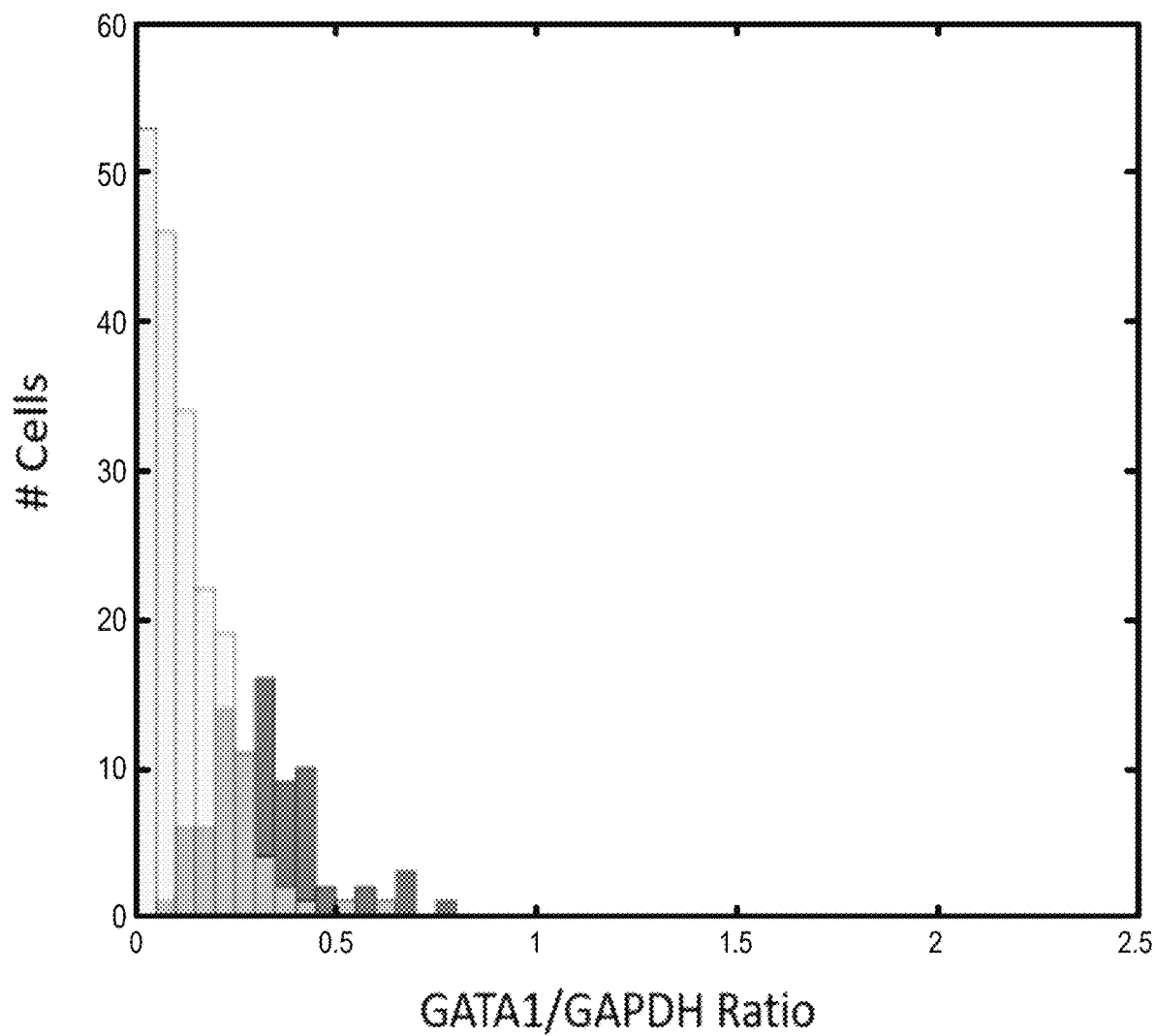
FIG. 10: Readout of CRISPRi perturbations with MIPs in two populations of cells—one expressed a sgRNA to target KRAB-dCas9 to the GATA1 promoter (Yellow), and the other expressed a non-targeting sgRNA (blue). Histogram shows the distribution of the ratio of GATA1 to GAPDH expression (MIP UMI counts) in each cell population, demonstrating quantification of GATA1 knockdown.
Figure 11:
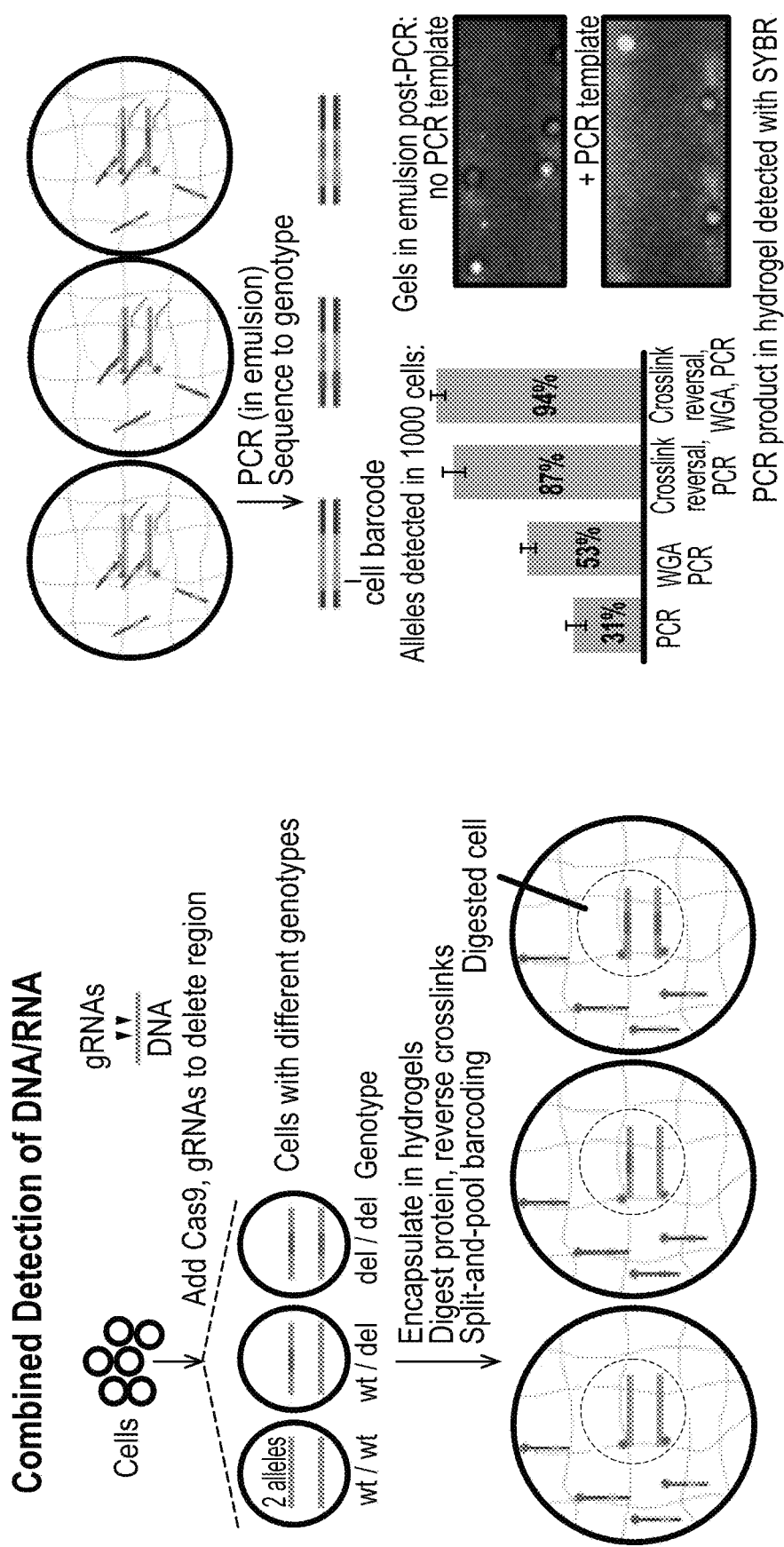
FIG. 11—Schematic for one embodiment of detecting the results of genetic perturbations to a DNA region in single cells, along with results showing DNA detection efficiency after treating Cell-In-Gels with different combinations of crosslink reversal, heat, and/or whole genome amplification (WGA).

To identify and enrich for the libraries from the fraction of cells containing the desired genotypes, we will use the Cell-In-Gel RNA-DNA barcoding technology to add cell barcodes to DNA and RNA contained within individual hydrogels, and create separate libraries for DNA amplicon sequencing and RNA sequencing. We will then sequence the DNA amplicon library to determine which cells (and corresponding cell barcodes) carry the desired genotype(s). We will then synthesize an oligonucleotide pool corresponding to the cell barcodes associated with the desired genotypes, and perform hybrid selection to enrich the RNA sequencing libraries (after conversion to DNA) matching only these cell barcodes, prior to sequencing. This will effectively reduce the cost of sequencing the desired RNA libraries by a factor of >10-fold, depending on the efficiency of editing and the number of barcodes selected, thus increasing capacity for multiplexed experiments (FIG. 7).

For large pools of lncRNAs (~100 lncRNAs/pool), whole-transcriptome sequencing will still require many sequencing reads. Even with the hybrid selection strategy described above, we expect that we would need ~6 billion sequencing reads (100 lncRNAs×600 cells per lncRNA× 100,000 reads per cell). This is feasible with current technologies, albeit expensive for each pool. We expect that this will become significantly more cost effective with anticipated advances in sequencing technologies. For example, based on the anticipated decrease in cost per read on the Illumina NovaSeq (10× cheaper relative to HiSeq), we expect that this approach will be cost-effective even for large pools of lncRNAs.

Example 10—Low-Cost Readout of Gene Expression Signatures

To increase the number of cells that can be analyzed and also reduce the cost associated with perturbation of large pools of lncRNAs, we will measure gene expression in a reduced-dimension space. For example, the L1000 assay measures the expression of 1000 "Landmark" genes, which are used to infer the expression levels of all other genes in the genome. This approach works well because gene expression patterns are highly correlated and as such 1000 genes strategically defined can be used accurately estimate global gene expression patterns. This assay has previously been broadly applied to characterize the pathway-level effects on gene expression for millions of samples. Building on this approach, we will create a reduced-dimension MIPs assay to measure each of these 1000 landmark genes, and calibrate it by comparing its performance versus the L1000 in bulk samples. We expect differences in performance in moving this assay to a single-cell format due to the sparse signal distributions, and so we will extend our existing scRNA-seq analytical approaches to infer changes in gene expression signatures from these data. In addition to the L1000 approach, we will explore an alternative measurement strategy that uses compressed sensing to reduce the measurement requirements by another factor of ~5, further reducing assay complexity and sequencing cost. Together, this approach will increase the throughput of sequencing experiments by reducing sequencing requirements by an additional factor of >10. Because this approach will use our RNA MIPs measurement strategy, the precise genes measured are flexible and can be combined with probes to provide sensitive readouts of specific genes (e.g., the lncRNA and its nearby genes) in addition to the probes dedicated to the reduced-dimension measurements.

Compressed Sensing

Mammalian genomes contain approximately 20,000 genes, and mammalian expression profiles are frequently studied as vectors with 20,000 entries corresponding to the abundance of each gene. It is often assumed that studying gene expression profiles requires measuring and analyzing these 20,000 dimensional vectors, but some mathematical results show that it is often possible to study high-dimensional data in low dimensional space without losing much of the pertinent information. In one embodiment of the present invention, less than 20,000 proteins are detected in single cells. Not being bound by a theory, working in low dimensional space offers several advantages with respect to computation, data acquisition and fundamental insights about biological systems.

In one embodiment, protein targets are chosen that are generally part of gene modules or programs, whereby detection of a protein allows for the ability to infer expression of other proteins present in a module or gene program. Samples are directly compared based only on the measurements of these signature genes.

In alternative embodiments, sparse coding or compressed sensing methods can be used to infer large amounts of data with a limited set of target proteins. Not being bound by a theory, the abundance of each of the 20,000 genes can be recovered from random composite measurements. In this regard, reference is made to Cleary et al., "Composite measurements and molecular compressed sensing for highly efficient transcriptomics" posted on Jan. 2, 2017 at biorxiv.org/content/early/2017/01/02/091926, doi.org/10.1101/091926, incorporated herein by reference in its entirety.

Example 11—Use of Kit for Drug Screening or Determining the Presence of Cancer Cells In certain embodiments, the present invention provides for a kit for determining the presence of cancer mutations in a subject in need thereof. In certain embodiments, a tumor sample is obtained from a subject suffering from cancer and the kit is applied to the sample to determine somatic mutations present in the subject's cancer. The presence of certain mutations can inform the treatment. For example, the presence of resistant mutations in clonal tumor cells may indicate that a treatment targeting the resistant cells may be administered. In another example the expansion of resistant cells can be monitored in the subject.

In certain embodiments, the present invention may be used to detect genes and mutations associated with cancer. Mutations associated across the spectrum of human cancer types have been identified (e.g., Hodis E. et al., Cell. (2012) July 20; 150(2):251-63; and Vogelstein, et al., Science (2013) March 29: Vol. 339, Issue 6127, pp. 1546-1558). A directory of cancer mutations, including gene specific mutations may be found at cancer.sanger.ac.uk/cosmic, the Catalogue of Somatic Mutations in Cancer (COSMIC) (Forbes, et al.; COSMIC: somatic cancer genetics at high-resolution. Nucleic Acids Res 2017; 45 (D1): D777-D783. doi:

10.1093/nar/gkw1121) and www.mycancergenome.org. In certain embodiments, any of these known mutations may be detected.

In certain embodiments, mutations associated with resistance are detected. The amplification of resistant tumor cells or appearance of resistant mutations in clonal populations of tumor cells may arise during treatment (see, e.g., Burger J A, et al., Clonal evolution in patients with chronic lymphocytic leukaemia developing resistance to BTK inhibition. Nat Commun. 2016 May 20; 7:11589; Landau D A, et al., Mutations driving CLL and their evolution in progression and relapse. Nature. 2015 Oct. 22; 526(7574):525-30; Landau D A, et al., Clonal evolution in hematological malignancies and therapeutic implications. Leukemia. 2014 January; 28(1):34-43; and Landau D A, et al., Evolution and impact of subclonal mutations in chronic lymphocytic leukemia. Cell. 2013 Feb. 14; 152(4):714-26). Accordingly, detecting such mutations requires highly sensitive assays and monitoring requires repeated biopsy. Repeated biopsies are inconvenient, invasive and costly. Resistant mutations can be difficult to detect in a blood sample or other noninvasively collected biological sample (e.g., blood, saliva, urine) using the prior methods known in the art. Resistant mutations may refer to mutations associated with resistance to a chemotherapy, targeted therapy, or immunotherapy.

In certain embodiments, mutations occur in individual cancers that may be used to detect cancer progression. In one embodiment, mutations related to T cell cytolytic activity against tumors have been characterized and may be detected by the present invention (see e.g., Rooney et al., Molecular and genetic properties of tumors associated with local immune cytolytic activity, Cell. 2015 Jan. 15; 160(1-2):48-61). Personalized therapies may be developed for a patient based on detection of these mutations (see e.g., WO2016100975A1). In certain embodiments, cancer specific mutations associated with cytolytic activity may be a mutation in a gene selected from the group consisting of CASP8, B2M, PIK3CA, SMC1A, ARID5B, TET2, ALPK2, COL5A1, TP53, DNER, NCOR1, MORC4, CIC, IRF6, MYOCD, ANKLE1, CNKSR1, NF1, SOS1, ARID2, CUL4B, DDX3X, FUBP1, TCP11L2, HLA-A, B or C, CSNK2A1, MET, ASXL1, PD-L1, PD-L2, IDO1, IDO2, ALOX12B and ALOX15B, or copy number gain, excluding whole-chromosome events, impacting any of the following chromosomal bands: 6q16.1-q21, 6q22.31-q24.1, 6q25.1-q26, 7p11.2-q11.1, 8p23.1, 8p11.23-p11.21 (containing IDO1, IDO2), 9p24.2-p23 (containing PDL1, PDL2), 10p15.3, 10p15.1-p13, 11p14.1, 12p13.32-p13.2, 17p13.1 (containing ALOX12B, ALOX15B), and 22q11.1-q11.21.

In certain embodiments, the present invention is used to detect a cancer mutation (e.g., resistance mutation) during the course of a treatment and after treatment is completed. The sensitivity of the present invention may allow for noninvasive detection of clonal mutations arising during treatment and can be used to detect a recurrence in the disease.

In certain example embodiments, detection of microRNAs (miRNA) and/or miRNA signatures of differentially expressed miRNA, may be used to detect or monitor progression of a cancer and/or detect drug resistance to a cancer therapy. As an example, Nadal et al. (Nature Scientific Reports, (2015) doi: 10.1038/srep12464) describe mRNA signatures that may be used to detect non-small cell lung cancer (NSCLC).

In certain example embodiments, the presence of resistance mutations in clonal subpopulations of cells may be used in determining a treatment regimen. In other embodiments, personalized therapies for treating a patient may be administered based on common tumor mutations. In certain embodiments, common mutations arise in response to treatment and lead to drug resistance. In certain embodiments, the present invention may be used in monitoring patients for cells acquiring a mutation or amplification of cells harboring such drug resistant mutations.

Treatment with various chemotherapeutic agents, particularly with targeted therapies such as tyrosine kinase inhibitors, frequently leads to new mutations in the target molecules that resist the activity of the therapeutic. Multiple strategies to overcome this resistance are being evaluated, including development of second generation therapies that are not affected by these mutations and treatment with multiple agents including those that act downstream of the resistance mutation. In an exemplary embodiment, a common mutation to ibrutinib, a molecule targeting Bruton's Tyrosine Kinase (BTK) and used for CLL and certain lymphomas, is a Cysteine to Serine change at position 481 (BTK/C481S). Erlotinib, which targets the tyrosine kinase domain of the Epidermal Growth Factor Receptor (EGFR), is commonly used in the treatment of lung cancer and resistant tumors invariably develop following therapy. A common mutation found in resistant clones is a threonine to methionine mutation at position 790.

Non-silent mutations shared between populations of cancer patients and common resistant mutations that may be detected with the present invention are known in the art (see e.g., WO/2016/187508). In certain embodiments, drug resistance mutations may be induced by treatment with ibrutinib, erlotinib, imatinib, gefitinib, crizotinib, trastuzumab, vemurafenib, RAF/MEK, check point blockade therapy, or anti-estrogen therapy. In certain embodiments, the cancer specific mutations are present in one or more genes encoding a protein selected from the group consisting of Programmed Death-Ligand 1 (PD-L1), androgen receptor (AR), Bruton's Tyrosine Kinase (BTK), Epidermal Growth Factor Receptor (EGFR), BCR-Abl, c-kit, PIK3CA, HER2, EML4-ALK, KRAS, ALK, ROS1, AKT1, BRAF, MEK1, MEK2, NRAS, RAC1, and ESR1.

Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Recently, gene expression in tumors and their microenvironments have been characterized at the single cell level (see e.g., Tirosh, et al. Dissecting the multicellular ecosystem of metastatic melanoma by single cell RNA-seq. Science 352, 189-196, doi: 10.1126/science.aad0501 (2016)); Tirosh et al., Single-cell RNA-seq supports a developmental hierarchy in human oligodendroglioma. Nature. 2016 Nov. 10; 539(7628):309-313. doi: 10.1038/nature20123. Epub 2016 Nov. 2; and International patent publication serial number WO 2017004153 A1). In certain embodiments, gene signatures may be detected using the present invention. In one embodiment complement genes are monitored or detected in a tumor microenvironment. In one embodiment MITF and AXL programs are monitored or detected. In one embodiment, a tumor specific stem cell or progenitor cell signature is detected. Such signatures indicate the state of an immune response and state of a tumor. In certain embodiments, the state of a tumor in terms of proliferation, resistance to treatment and abundance of immune cells may be detected.

Thus, in certain embodiments, the invention provides low-cost, multiplexed cancer diagnostic panels, particularly for monitoring disease recurrence or the development of common resistance mutations, gene expression signatures, immune response signatures, and identifying the sequences of B-cell and T-cell receptors.

In other embodiments, the invention is used to detect immune gene expression signatures and/or sequences of B-cell and T-cell receptors, for example to monitor progression of autoimmune diseases, vaccine efficacy, or infection responses.

In other embodiments, the invention is used to detect and monitor somatic mutations and/or gene expression signatures in clonal hematopoiesis (CHIP) to monitor risk for heart disease or cancer.

Example 12—HYbridization Probes RNA Sequencing (HYPR-Seq)

This example shows exemplary methods of generating and using a HYPR-Seq, an adapted HCR system.
Methods
Cell Preparation Cells (3-5 million per condition) were transferred to a 15 mL conical tube and centrifuge for 5 min at 350 g at 4° C. The supernatant was aspirated. Cell pellet was washed in cold 3-5 ml PBS, and spun 5 min at 350 g at 4° C. Supernatant was aspirated, and the cells were resuspended in 5 ml 4% formaldehyde in PBST (3-5 million cells).

The cells were fixed for at least 1 hour at room temperature. The sample was centrifuged for 5 min at 850 g and supernatant was aspirated. The cells were washed with 3-5 ml PBST twice, and centrifuged for 5 min at 850 g. The cells were resuspended cells in 3-5 ml cold 70% ethanol, and stored at 4° C. for 10 minutes.

The cells were centrifuged and washed with 3-5 mL PBST twice.
Detection Stage

The cells were transferred to 2 ml wide bottom tubes and centrifuge for 5 min at 850 g. the pellet was resuspended with 500 µL of 30% probe hybridization buffer and pre-hybridized for 5 min at 37° C.

In the meantime, probe solution was prepared by adding final 200 nM total concentration probe mix (20 nM per probe) to 200 µL of 30% probe hybridization buffer. The sample was centrifuged for 5 min to remove supernatant and add probe solution. The sample was incubated overnight at 37° C.

The incubated sample was centrifuged for 5 min to remove probe solution. The cell pellet was resuspended with 500 µL of 30% probe wash buffer. The sample was incubated for 10 min at 37° C. and the wash solution was removed by centrifugation for 5 minutes repeated for 3 additional times. After the 1st repeat, the hairpins were denatured (see below for detail). The samples were centrifuged for 5 minutes and the cell pellet was resuspended with 500 µL of 5×SSCT. The sample was then incubated for 5 minutes at room temperature. The sample was ready to proceed to hairpin amplification below.

Amplification Stage

The sample was centrifuged for 5 min to pellet the cells. The cell pellet was resuspended with 200 µL of 5×SSCT and incubated for 30 min at room temperature (this step may be optional). 15 pmol of each hairpin was prepared by snap cooling 5 µL of 3 µM stock in hairpin storage buffer (heat at 95° C. for 90 seconds and cool to room temperature in a dark drawer for 30 min). The 1st hairpin mixture was prepared by adding 5 µL of H1 to 200 µL of amplification buffer at room temperature.

The sample was centrifuged for 5 min to pellet the cells, supernatant was aspirated, and the hairpin mixture was added directly to the sample. The sample was incubated for 1 hour at room temperature.

The sample was centrifuged for 5 min and the hairpin solution was removed. The pellet was washed with 500 µL of 5×SSCT. The sample was centrifuged for 5 min and the supernatant was removed. The pellet washed with 500 µL of 5×SSCT.

The 2nd hairpin mixture was prepared by adding 5 µL of 0B H2 to 200 µL of amplification buffer at room temperature. The sample was centrifuge for 5 min to pellet the cells, the supernatant was aspirated and the hairpin mixture was added directly to the sample. The sample was incubated for 1 hour at room temperature.

Then, the sample was centrifuged for 5 min to pellet the cells, the supernatant was aspirate, and the cell pellet was resuspended with 500 µL of 5×SSCT. Without incubation, the wash solution was removed by centrifugation for 5 min. The sample was then: washed in 500 µL of 5×SSCT, washed in 500 µL 0.2% PBST, washed in 500 L 0.2% PBST, and washed in 200 µL 1×T4 Buffer.

The sample was centrifuged for 5 min to pellet the cells, the supernatant aspirated, and the cells were incubates in 200 µL T4 ligation mixture for 1 hours at room temperature.

T4 Ligation Mixture
10× T4 Buffer
1:100 T4 DNA Ligase
Rest of volume in water

The cells were then washed in 400 µL 0.2% PBST, washed in 400 µL 0.2% PBST, resuspended in 400 µL 0.2% PBST, and filtered. The cells were then counted and proceeded to Bulk or EM PCRs.
PCR The clumps were removed by filtering cells through pluristrainer, 20 uM. The cells were counted and subjected to PCR reaction using conditions below.
PCR Reactions used are below:
Emulsions:
50 µl 2× Evagreen
12.5 µl beads (concentrated 4×)
62.5 µl MM/tube
5 µl ad1 primer (ad1.3-1.10)
10,000 cells (max vol 16.25)
32.5—vol of cells Water
Bulk:
10 ul 2× Evagreen
3 ul Water
13 ul MM/tube
1 ul ad1 primer
1 ul ad2 primer
5 ul 100 cells (8 ul max)

The bulk was placed in PCR machine. For EM, droplets were loaded
70 ul Oil (bottom, med sized)
20 ul PCR (middle, small sized)->do replicates for each condition For EM, after the droplets were formed, the sample was put under UV light for 2 min (4 wells at a time). For EM, the plate was sealed and loaded in the PCR machine.

Clean-Up and Pool 2 ul of the bulk PCR reaction was run on a 2% gel. DNA-SPRI beads were equilibrated to room temperature for about 30 min. Fresh 70% EtOH was prepared. For EM, the samples were moved to PCR strip. 40 ul of PFO was added. For EM, each sample was mixed gently by pipetting up and down twice. For EM each sample was spun for 1 min. The top phase was moved to a new strip tube.

The DNA-SPRI beads were vortexed (Started here for B). 1.8× (if EM—13 ul sample, 23.4 ul beads, 3×—70.2 ul, 4×—94 ul; Bulk—20 ul sample, 36 ul) was added. The sample was incubated at room temperature for 10 min. With tube on mag, the supernatant was carefully aspirated and discarded. 100 ul 70% EtOH was added.

The samples were allowed to sit for 2 min. The supernatant was aspirated. This step was repeated once. The samples were removed from mag and dried at room temperature for about 5 min or until beads crack. 13 ul of TE buffer was added, pipetted to mix well, and incubated at room temperature for 1 min. The tube was placed on mag and incubated for 1 min.

12.5 ul of each sample was pipetted into new PCR tubes. Qubit was performed (each tube 200 ul; for DNA standards 10 ul+190 reagent working solution; 1 ul samples+199 ul reagent working solution). Equal concentrations of EM and B were pooled separately and the concentration was checked with Qubit. Average of triplicates was calculated. Average fragment length (201 bp) was determined by BioA or gel on pooled library. The library was stored at −20° C. until ready for sequencing.

Figure 12:
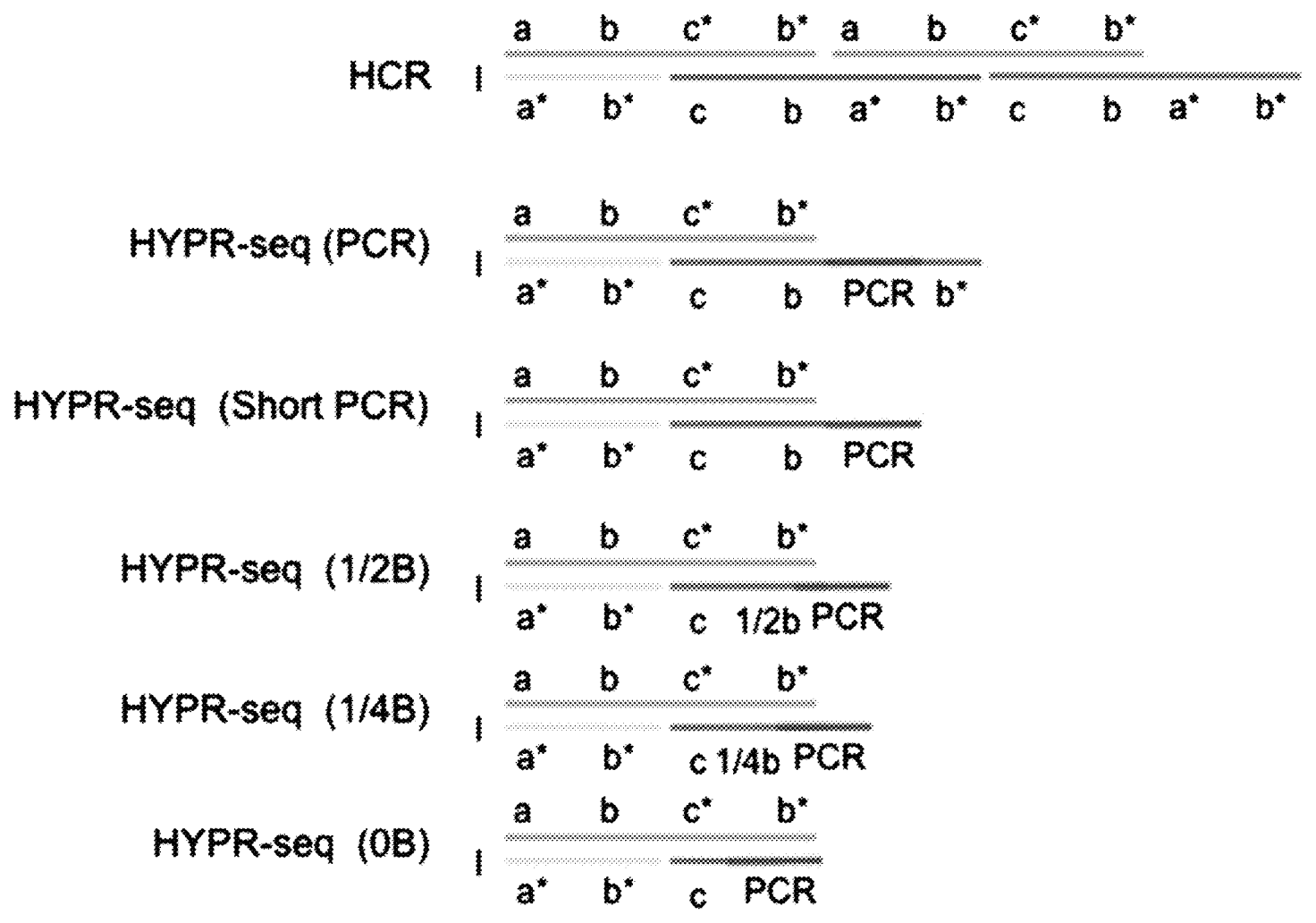

Buffers Used
4% formaldehyde in PBST (50 ml)
4% PFA (stored in 4 degrees)
50 ul Tween-20
0.2% PBST (50 ml)
100 ul Tween-20
50 ml PBS
Probe Hyb/Wash Buffer (50 ml)
12.5 ml 20×SSC (5×)
15 ml formamide (30%, stored at 4 degrees)
50 ul Tween-20 (0.1%)
22.5 ml Water
70% EtOH (50 ml)
35 ml EtOH
15 ml Water
5×SSCT (50 ml)
12.5 ml 20×SSC (5×)
50 ul Tween-20 (0.1%)
37.5 ml Water Results An exemplary run of HYPR-seq based on the methods above is shown in FIG. 12. 1210 and 1220 were the first and the second targeting probes. The two targeting probes 1210 and 1220 bound to the target mRNA 1230. Each of the targeting probe hybridized with 25 nt on target mRNA 1230, with a space of 2 nt in between. Targeting probe 1210 included a sequencing adaptor 1212 and a UMI 1211.

After targeting probes 1210 and 1220 bound to target mRNA 1230, a first sensing oligo 1230 bound to both target probes 1210 and 1220. Then, a second sensing oligo 1240, which comprised another sequencing adaptor 1241 and a hybridization region 1242, bound with the first sensing oligo 1230 via hybridization region 1242. The hybridization region 1242 was 2 nt in length.

Then the hybridization region 1242 in the second sensing oligo 1240 was ligated to the first targeting probe 1210, forming a sequencing construct, which included the second sensing oligo 1240 (including sequencing adaptor 1241 and hybridization region 1242) and the first targeting probe 1210 (including sequencing adaptor 1212 and UMI 1211).

Various designs of the sensing probe were tested. The sequences of the tested sensing probes are shown in the table below and FIG. 12. As shown in FIG. 12, the first sensing oligo is on the top (e.g., the original HCR system (top)). ½ of the initiator from the 5' targeting probe is shown in yellow, the first sensing oligo in green. The second oligo includes a section in purple with regions of homology indicated by a, a*, b, b*, c, and c*. The diagrams below depict 5 iterations of HYPR-seq design which involved altering the sensing oligo to add a sequencing adaptor (PCR) and shortening the homology region to the first sensing oligo. HYPR-seq (0B-2) resulted in moving 2 bp from the 5' targeting probe initiator to 0B-2 H2. 0B-2 was selected and used for further experiment.

TABLE 1

| Hairpin | Sequence |
|---|---|
| The first sensing oligo | |
| B1H1 (from Molecular Technologies) | CgTAAAggAAgACTCTTCCCgTTTgCTgCCCTC CTCgCATTCTTTCTTgAggAgg gCAgCAAACgggAAgAg/C9-dye-3'/ (SEQ ID NO: 1) |
| The second sensing oligo | |
| B1H2 (unlabeled) | gAggAgggCAgCAAACgggAAgAgTCTTCCTTT ACgCTCTTCCCgTTTgCTgCCC TCCTCAAgAAAgAATgC (SEQ ID NO: 2) |
| Short PCR | CTTACGGATGTTGCACCAGC CTCTTCCCgTTTgCTgCCCTCCTCAAgAAAgAA TgC (SEQ ID NO: 3) |
| 1/2B PCR | CTTACGGATGTTGCACCAGC gCTgCCCTCCTCAAgAAAgAATgC (SEQ ID NO: 4) |
| 1/4B PCR | CTTACGGATGTTGCACCAGC CTCCTCAAgAAAgAATgC (SEQ ID NO: 5) |
| 0B PCR | CTTACGGATGTTGCACCAGC AAgAAAgAATgC (SEQ ID NO: 6) |
| 0B-1 | CTTACGGATGTTGCACCAGC AAgAAAgAATgCG (SEQ ID NO: 7) |
| 0B-2 | CTTACGGATGTTGCACCAGC AAgAAAgAATgCGA (SEQ ID NO: 8) |
| 0B-3 | CTTACGGATGTTGCACCAGC AAgAAAgAATgCGAG (SEQ ID NO: 9) |
| 0B-2 (Rev P7/P5) | GAGCTTTGCTAACGGTCGAGAAgAAAgAATgCG A (SEQ ID NO: 10) |

Figure 13:
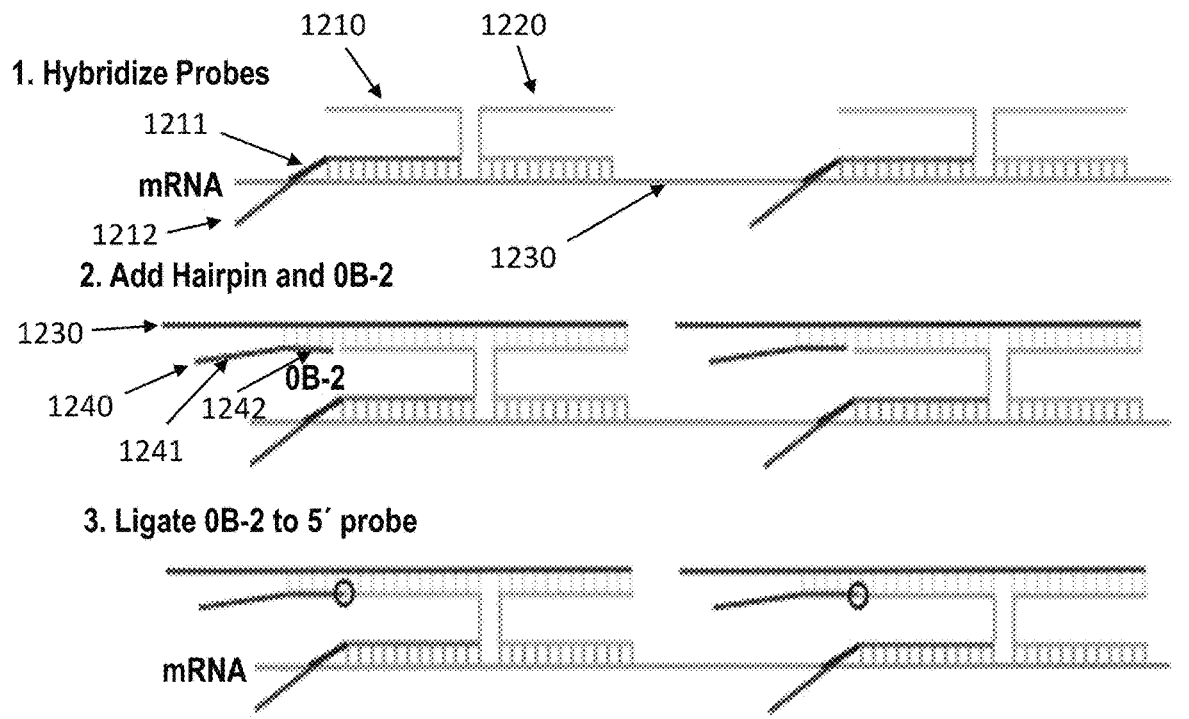
FIG. 13—shows an alternate example method for generating a sequencing library using an adapted HCR system.
Figure 13:
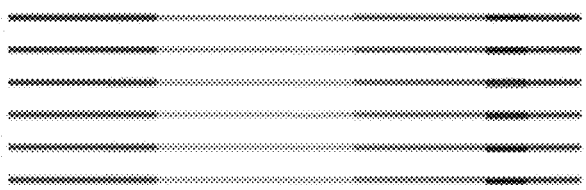
Figure 17:
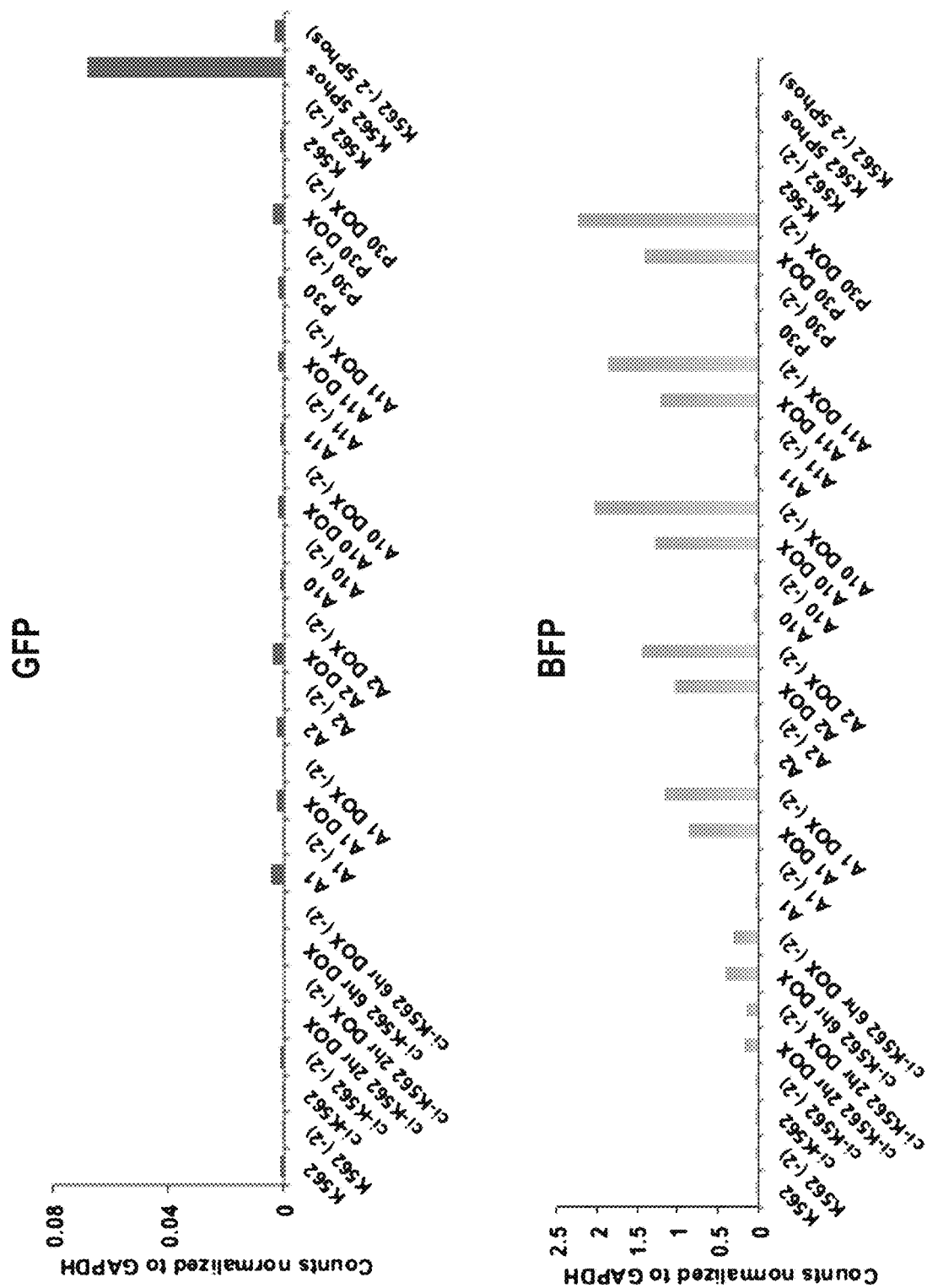
FIG. 17—shows the reduction of GFP background using the 0B-2 variation of the adapted HCR system while maintaining the ability to detect BFP expression.
Figure 18:
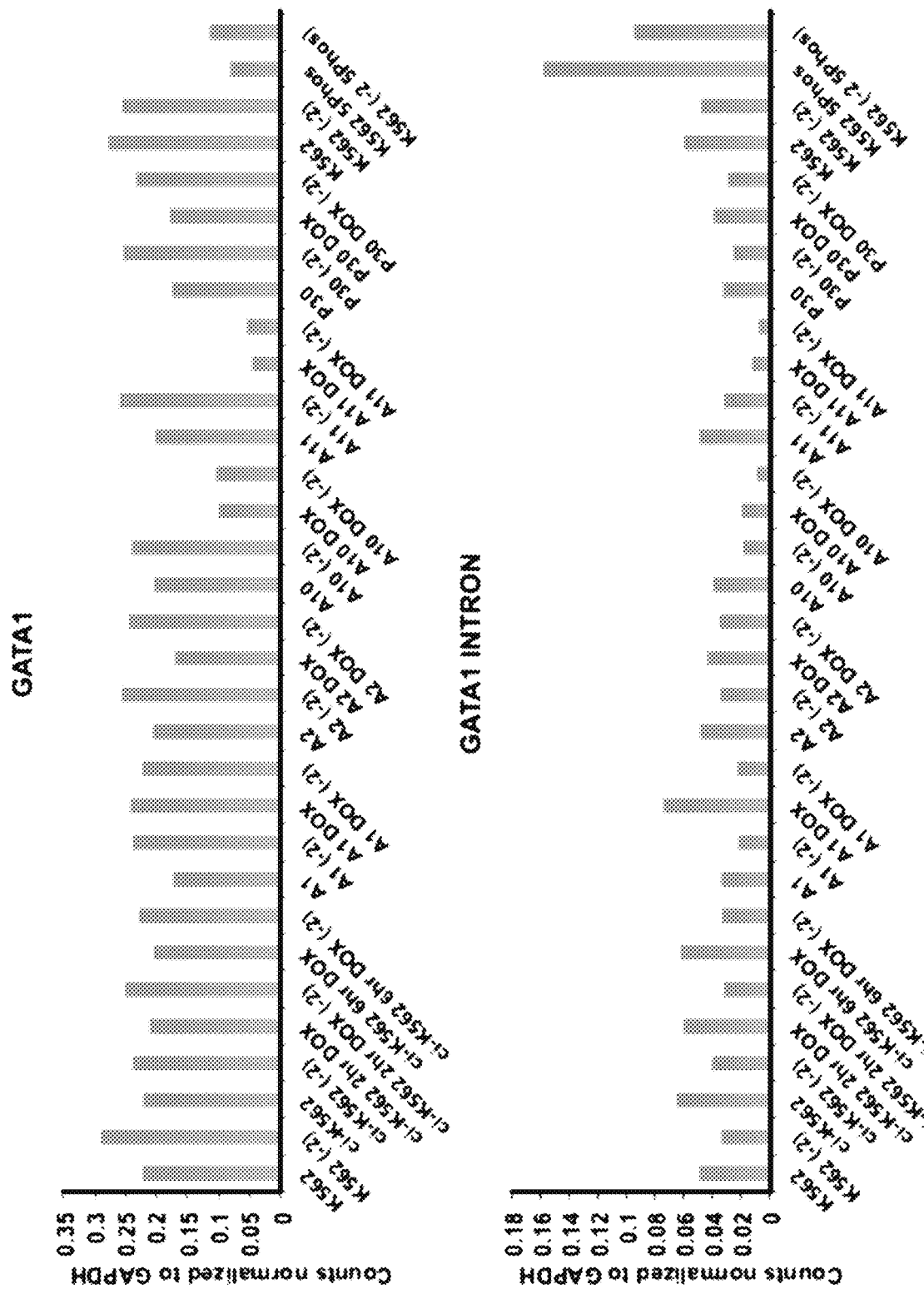
FIG. 18—is related to FIG. 17, and demonstrates the ability to maintain detection of MYC introns 1 and 2 using the 0B-2 variation of the adapted HCR system.
Figure 19:
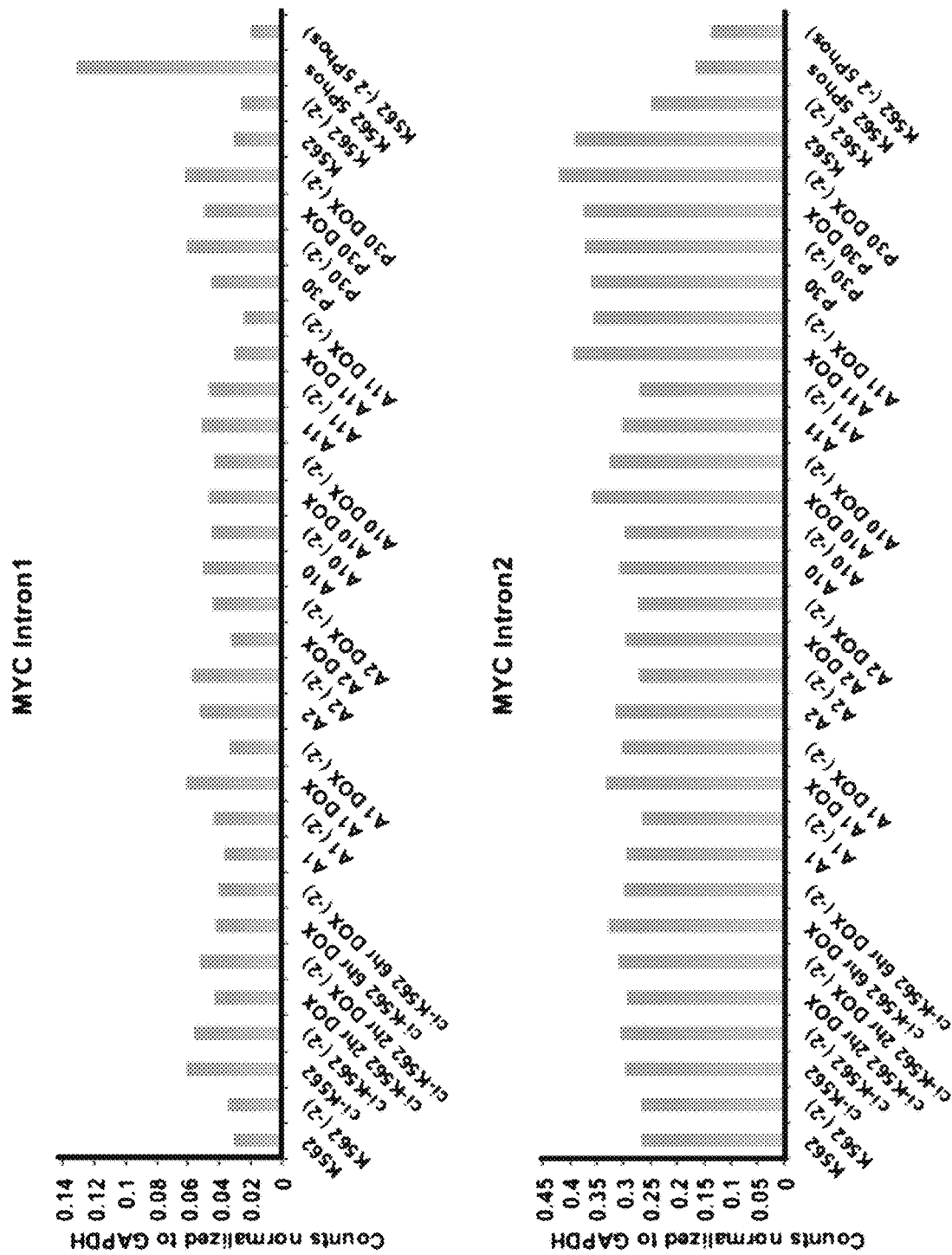
FIG. 19—is related to FIG. 17, and demonstrates the ability to maintain detection of GATA1 and GATA1 intron using the 0B-2 variation of the adapted HCR system.
Figure 20:
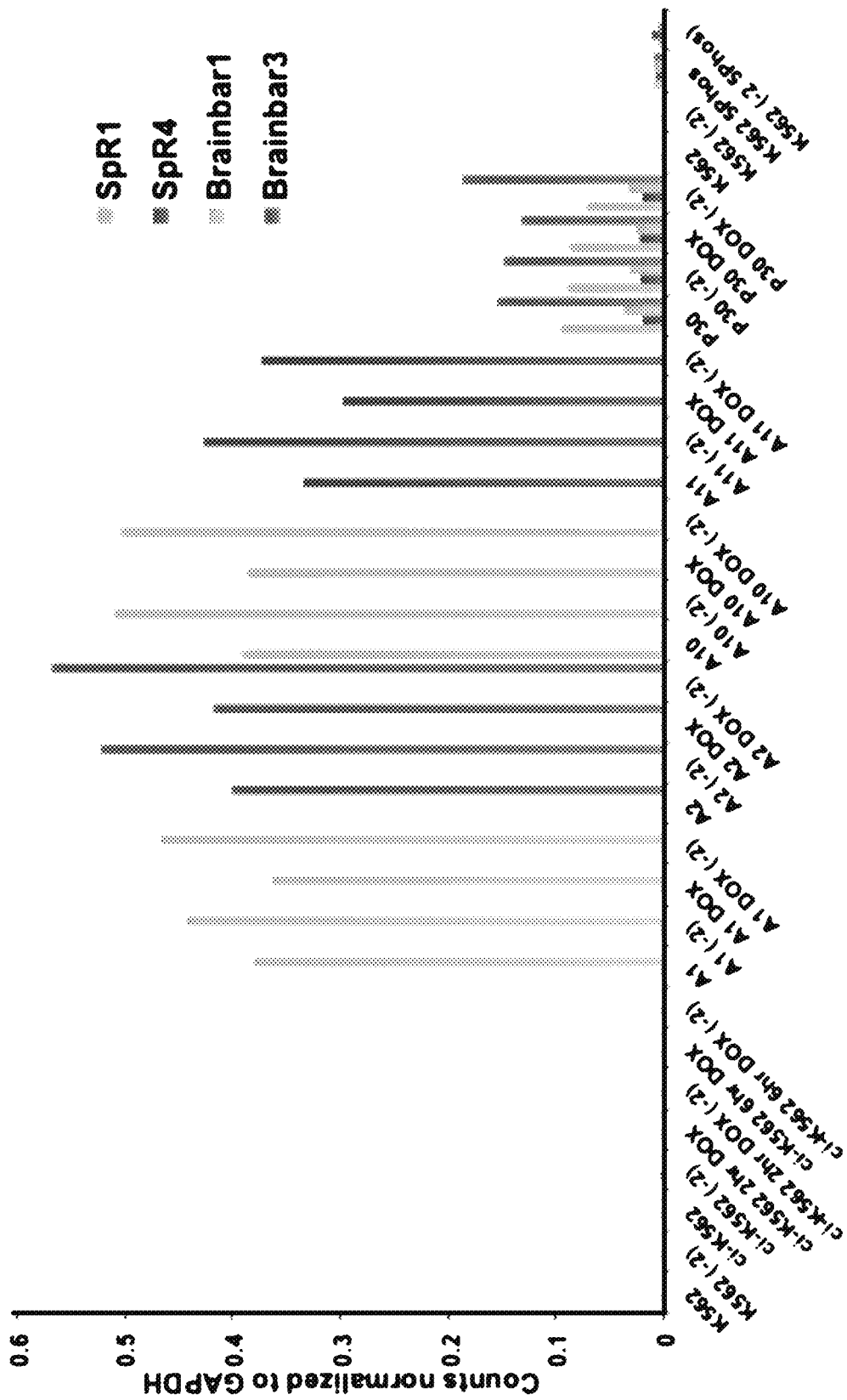
FIG. 20—shows the ability to accurately detect cell barcodes using an adapted HCR system.
Figure 21:
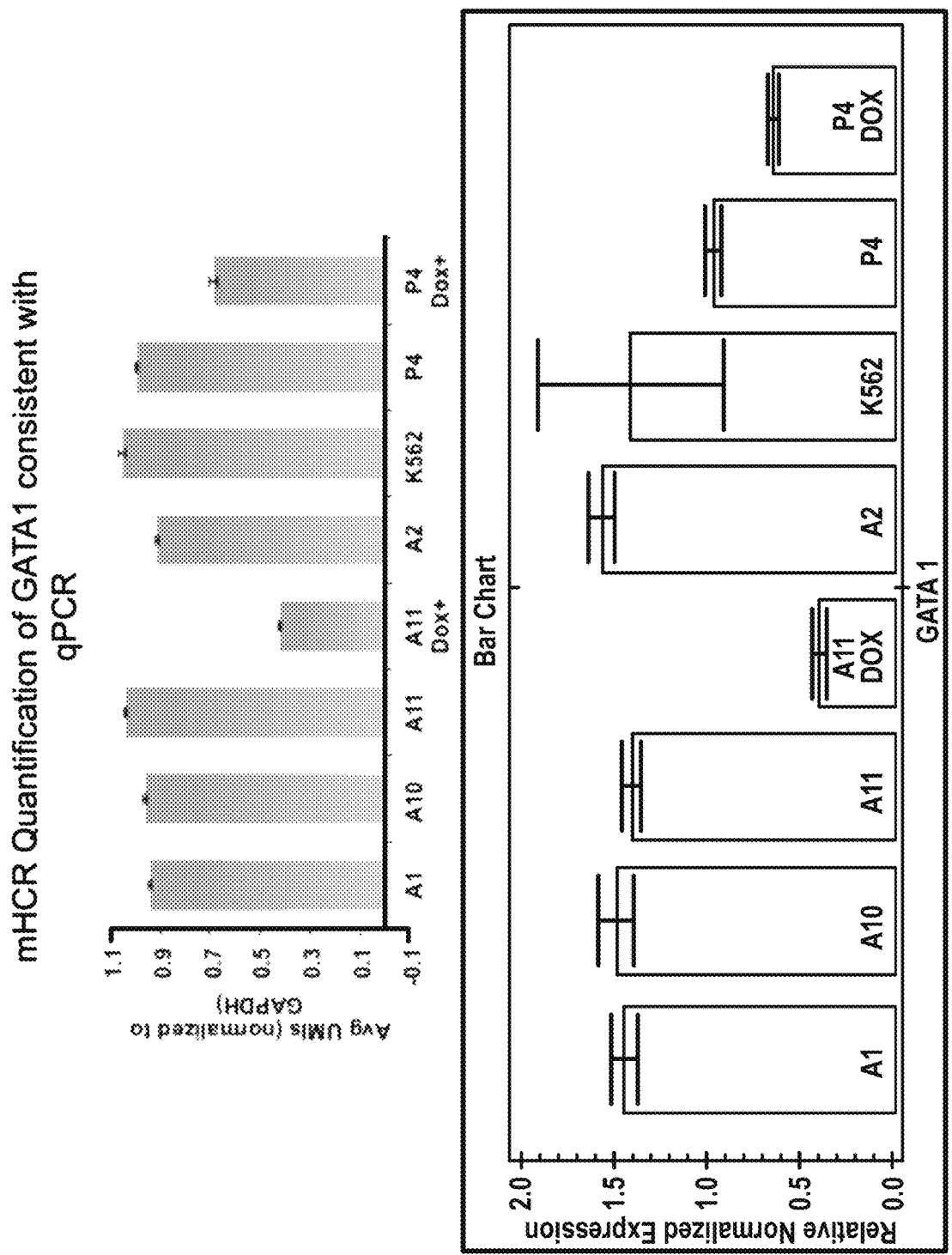
FIG. 21—shows quantitation of GATA1 consistent with qPCR using an adapted HCR system.
Figure 22:
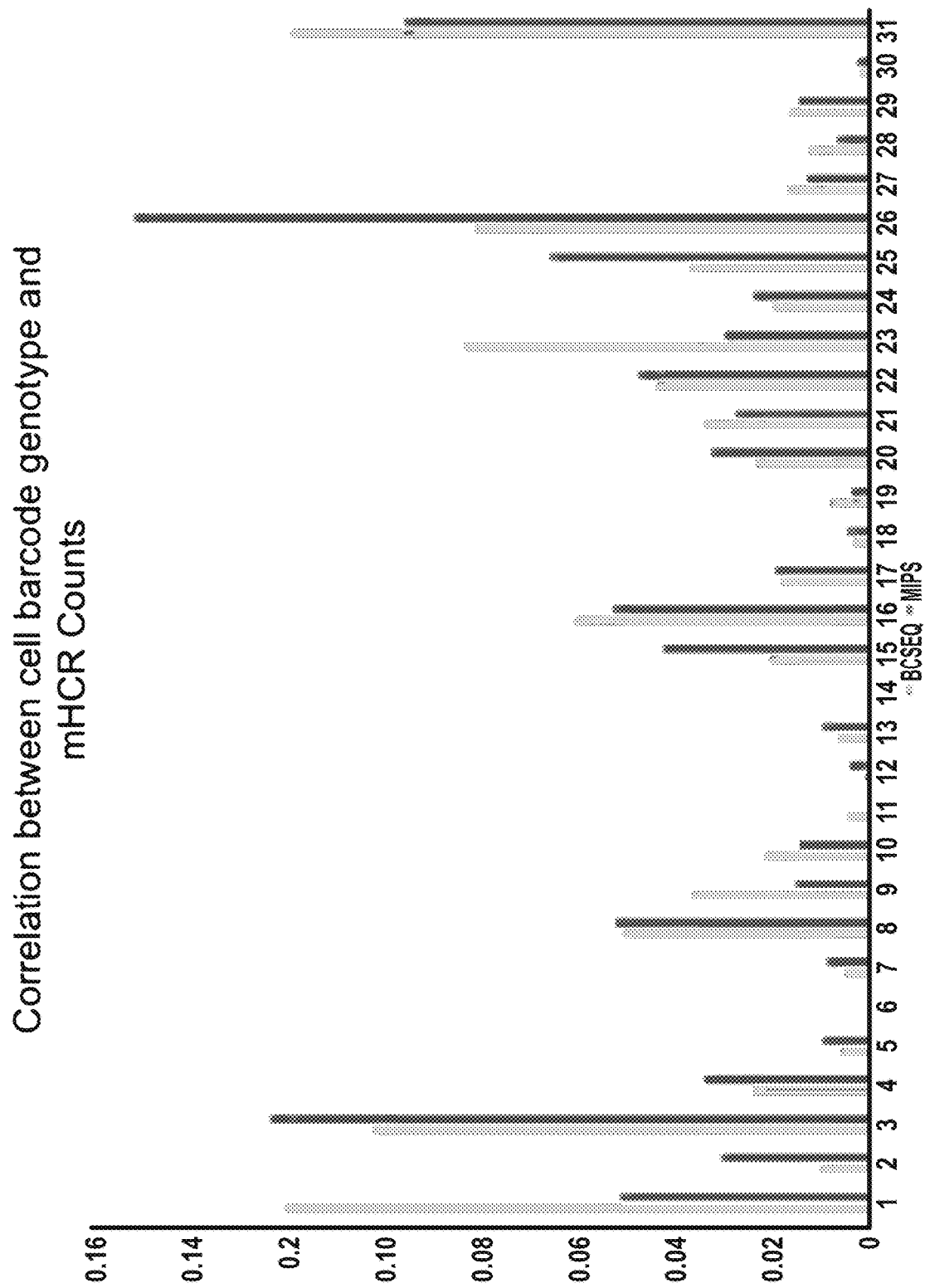
FIG. 22—shows correlation between cell barcode genotype and adapted HCR counts.
Figure 23:
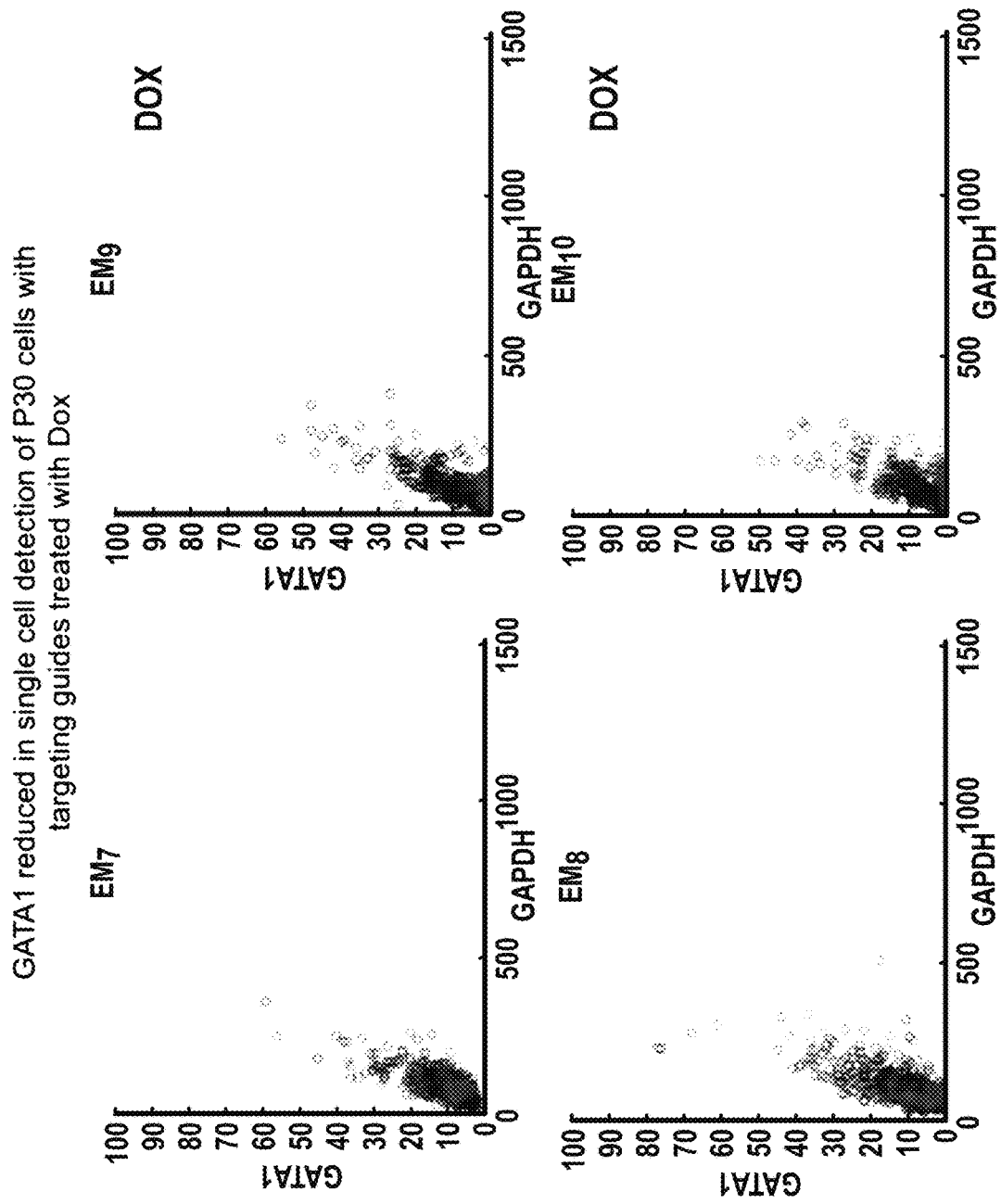
FIG. 23—shows the ability to detect the knockdown of GATA1 at the single cell level specifically in cells treated with doxycycline (turns on the cell machinery) and containing the CRISPRi guides targeting GATA1 (orange). Cell treated with doxycycline that do not contain targeting CRISPRi guides (blue) maintain normal expression of GATA1.
Figure 24:
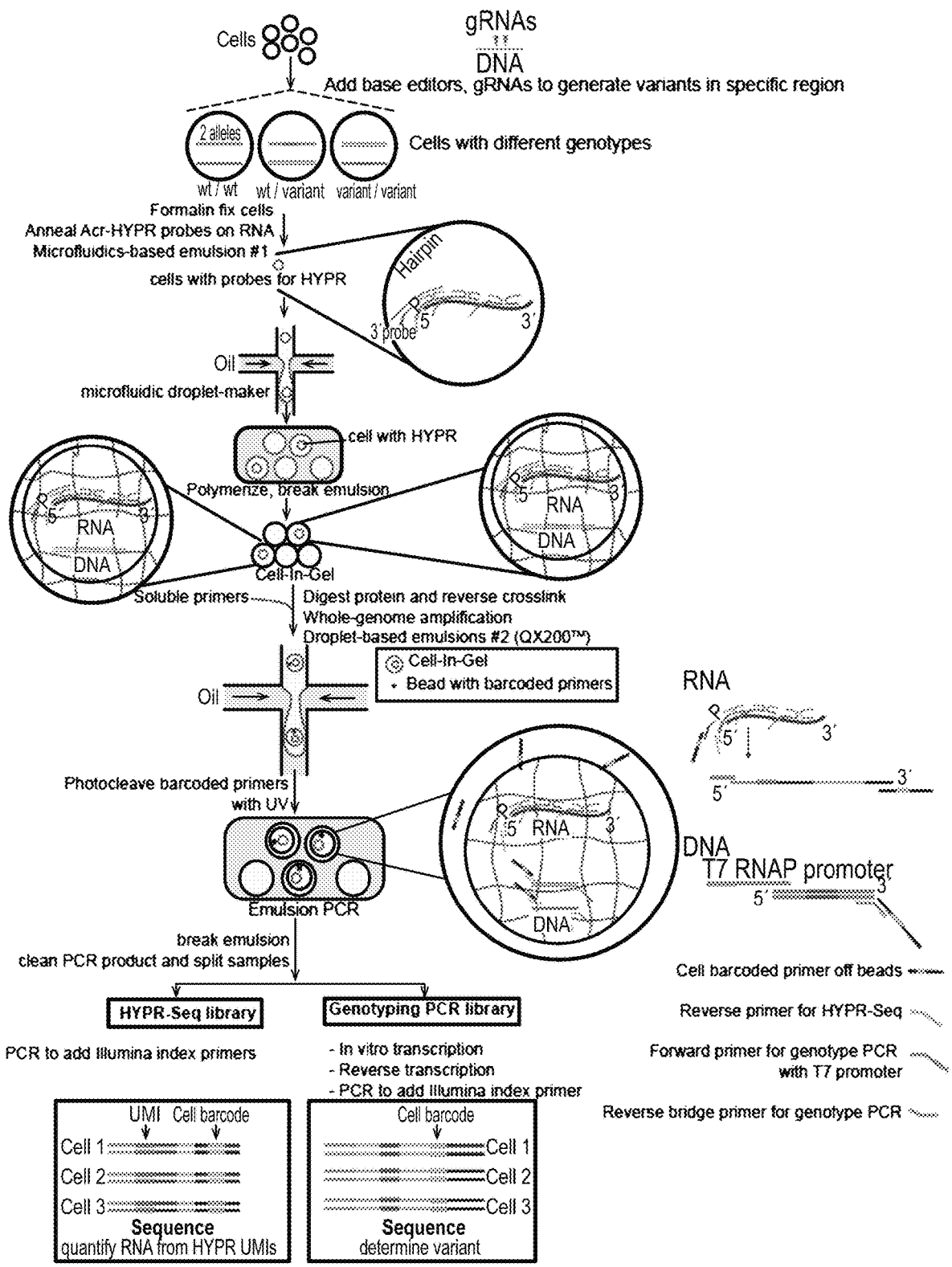
FIG. 24—Schematic diagram of approach combining targeted RNA readouts with DNA genotyping by encapsulating cells in hydrogels.

The sequencing construct was amplified using PCR to generate a sequencing library shown in FIG. 13 (bottom panel). Targeting probes for GAPDH were used. Sequences of the 5' targeting probes and 3' targeting probes are shown in the tables below. These designs would work with any initiator/hairpin system (B1-B5) using the initiator and spacer sequences from Choi et al., ACS Nano. 2014 May 27; 8(5):4284-94. Additionally this system would work with any PCR sequencing adapter system, including P7, P5, and the T7 in vitro transcription reaction.

the expression of cell barcodes and GATA1 normalized to GAPDH using the adapted HCR system. FIG. 17 shows the reduction of GFP background using the 0B-2 variation of the adapted HCR system while maintaining the ability to detect BFP expression. FIG. 18 is related to FIG. 17, and demonstrates the ability to maintain detection of MYC introns 1 and 2 using the 0B-2 variation of the adapted HCR system. FIG. 19 is related to FIG. 17, and demonstrates the ability to maintain detection of GATA1 and GATA1 intron using the 0B-2 variation of the adapted HCR system. FIG. 20 shows the ability to accurately detect cell barcodes using an adapted HCR system. FIG. 21 shows quantitation of GATA1 consistent with qPCR using an adapted HCR system. FIG. 22 shows correlation between cell barcode genotype and adapted HCR counts. FIG. 23 shows the ability to detect the knockdown of GATA1 at the single cell level specifically in cells treated with doxycycline (turns on the cell machinery) and containing the CRISPRi guides targeting GATA1 (orange). Cell treated with doxycycline that do not contain targeting CRISPRi guides (blue) maintain normal expression of GATA1.

TABLE 2

5' probes

| 5' probe Name | Initiator | Spacer | RNA Homology (changes based on RNA target) | UMI | Sequencing Adaptor | Full Probe |
|---|---|---|---|---|---|---|
| GAPDH HCR (82 bp) | /5Phos/ GAG GAGGGCA GCAAACG G (SEQ ID NO: 11) | AA | CCATGGGT GGAATCAT ATTGGAAC A (SEQ ID NO: 12) | NNNNN NNNNN (SEQ ID NO: 13) | CTCGACC GTTAGCA AAGCTC (SEQ ID NO: 14) | /5Phos/ GAGG AGGGCAGC AAACGGAA ACCAGGCG CCCAATAC GACCAAAT CNNNNNNN NNNCTCGA CCGTTAGC AAAGCTC (SEQ ID NO: 15) |
| GAPDH HCR-2 (80 bp) | /5Phos/ GGA GGGCAGC AAACGG (SEQ ID NO: 16) | AA | CCATGGGT GGAATCAT ATTGGAAC A (SEQ ID NO: 12) | NNNNN NNNNN (SEQ ID NO: 13) | CTCGACC GTTAGCA AAGCTC (SEQ ID NO: 14) | /5Phos/ GGAG GGCAGCAA ACGGAACC ATGGGTGG AATCATATT GGAACANN NNNNNNNN CTCGACCGT TAGCAAAG CTC (SEQ ID NO: 17) |
| GAPDH HCR-2 Rev P7/P5 (80 bp) | /5Phos/ GGA GGGCAGC AAACGG (SEQ ID NO: 16) | AA | CCATGGGT GGAATCAT ATTGGAAC A (SEQ ID NO: 12) | NNNNN NNNNN (SEQ ID NO: 13) | GCTGGTG CAACATC CGTAAG (SEQ ID NO: 18) | /5Phos/ GGAG GGCAGCAA ACGGAACC ATGGGTGG AATCATATT GGAACANN NNNNNNNN GCTGGTGC AACATCCG TAAG (SEQ ID NO: 19) |

TABLE 3

3' probe

| 3' probe Name | RNA Homology (changes based on RNA target) | Spacer | Initiator |
|---|---|---|---|
| GAPDH HCR (45 bp) | TTACCAGAGTTAAAAG CAGCCCTGG (SEQ ID NO: 20) | TA | GAAGAGTCTTCCTTTA CG (SEQ ID NO: 21) |

Figure 14:
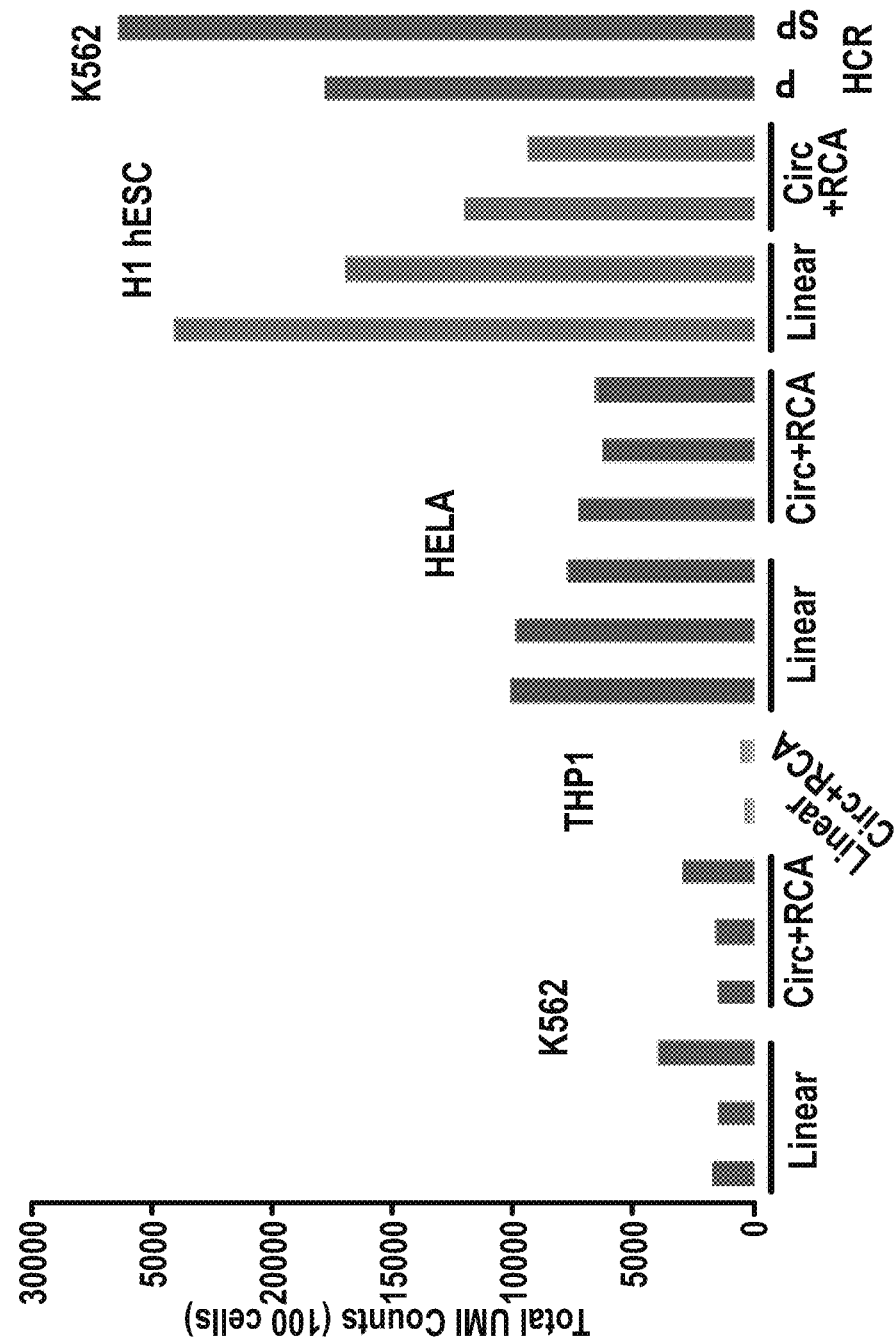
FIG. 14—shows ability to detect increased GAPDH UMIs using an adapted HCR system.
Figure 15:
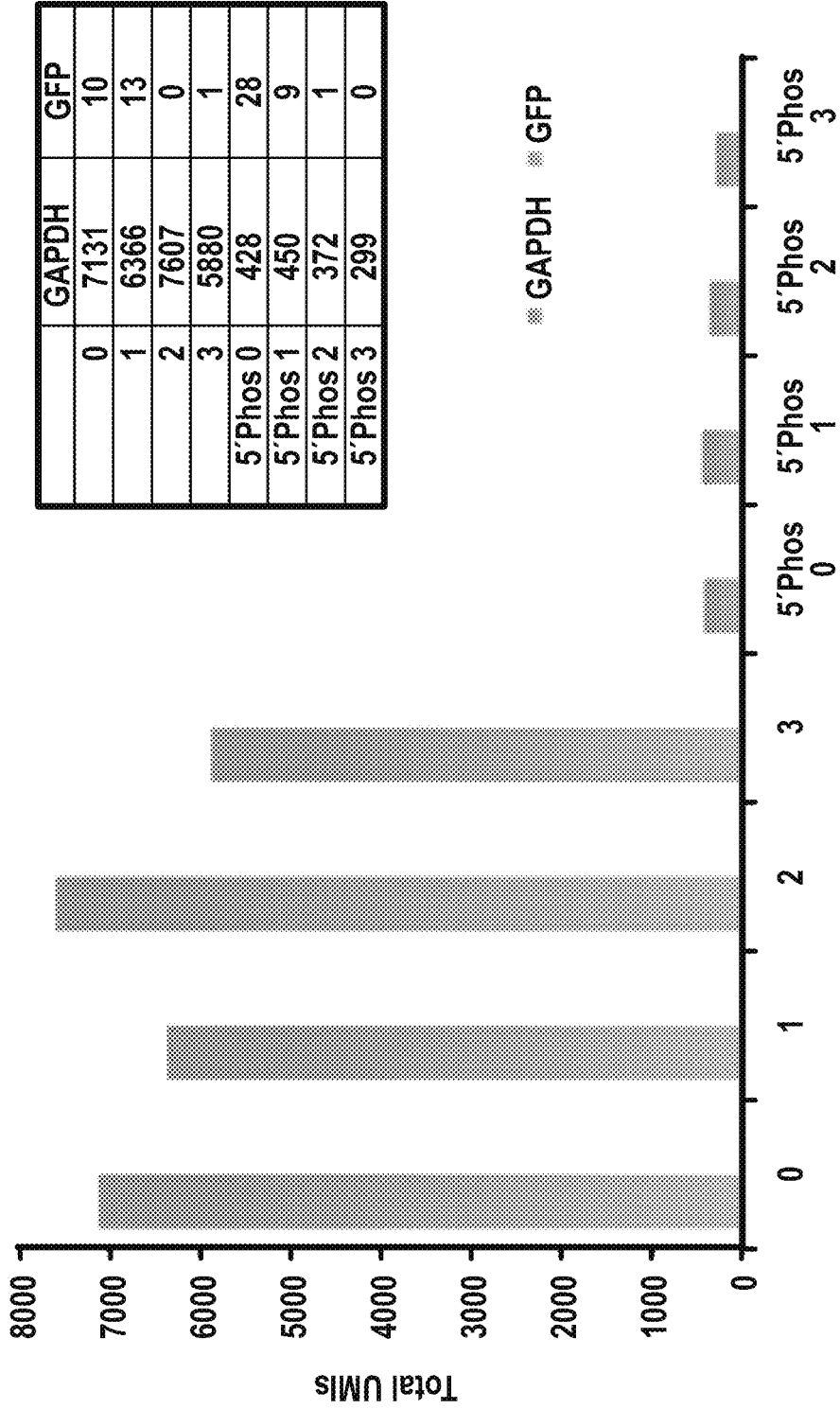
FIG. 15—shows an ability to reduce 5'Phos and GFP background using an adapted HCR system.
Figure 16:
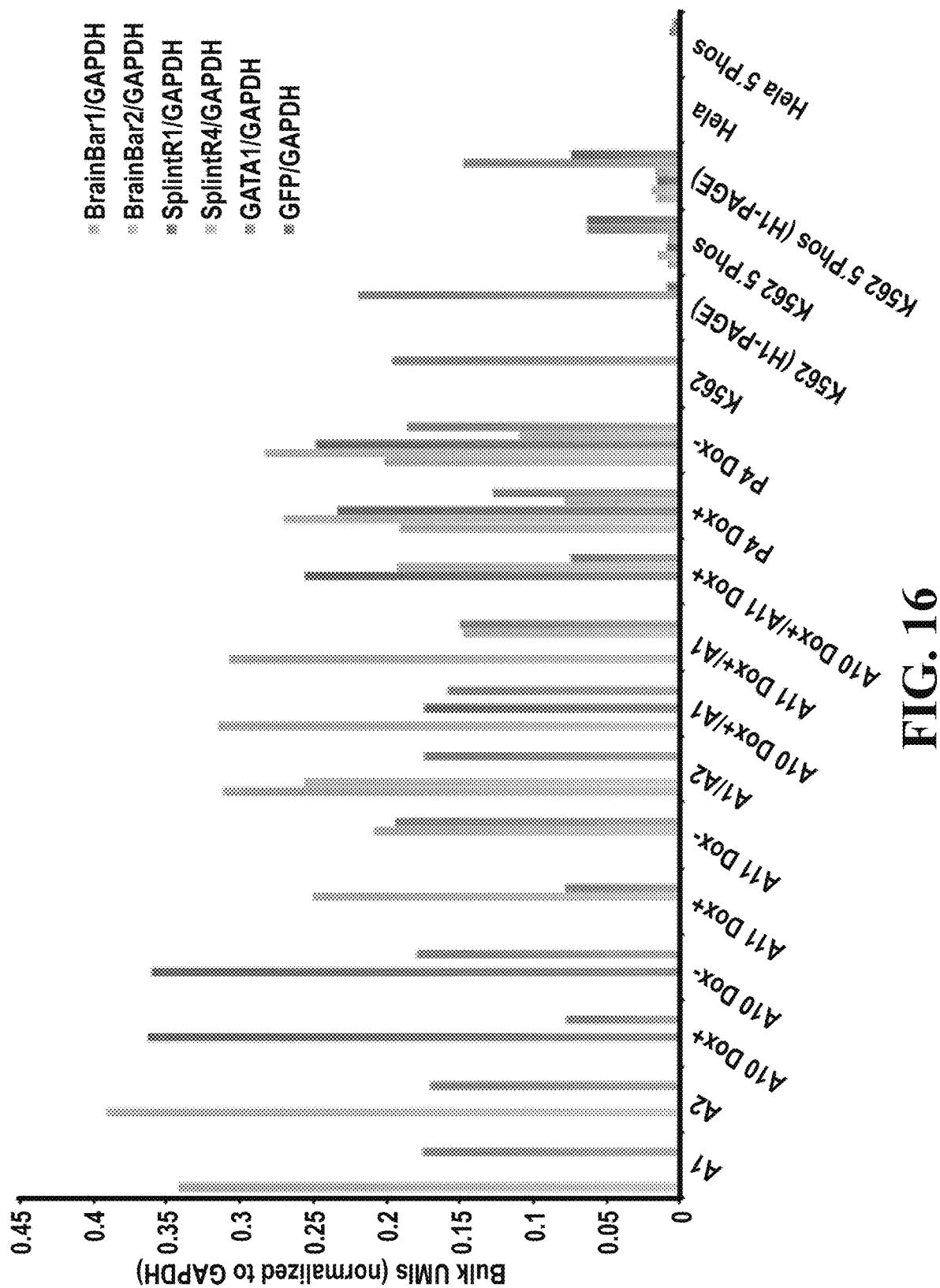
FIG. 16—shows the expression of cell barcodes and GATA1 normalized to GAPDH using an adapted HCR system.

Test results using the targeting probes and sensing oligos herein are shown in FIGS. 14-23. FIG. 14 shows ability to detect increased GAPDH UMIs using the adapted HCR system. FIG. 15 shows an ability to reduce 5'Phos and GFP background using the adapted HCR system. FIG. 16 shows

Example 13—Cell Gel Generation

Reagents

TABLE 4

4X AB

| 4X AB | mL |
|---|---|
| AA/bis | 3.6 |
| 40% AA | 2.58 |
| Water | 3.82 |

TABLE 5

1X TBSET

| 1X TBSET | mL | Final conc. |
|---|---|---|
| Tris HCl pH 8.0 (1M) | 10 | 10 mM |
| NaCl (5M) | 27.4 | 137 mM |
| KCl (2M) | 1.35 | 2.7 mM |
| EDTA (0.5M) | 20 | 10 mM |
| Triton X-100 (10%) | 10 | 0.1% |
| Water | 931.25 | |
| Total | 1000 | |

TABLE 6

| 10% APS | mL or g | Final conc. |
|---|---|---|
| Ammonium persulfate | 1 | 10% |
| Water | 9.5 | |
| Total | 10 | |

TABLE 7

| Wash buffer | mL | Final conc. |
|---|---|---|
| 20X SSC | 7.5 | 3X |
| 0.5M EDTA | 0.01 | 0.1 mM |
| Triton X-100 (10%) | 0.05 | 0.01% |
| Water | 42.44 | |
| Total | 50 | |

TABLE 8

Cell Gel Recipe

| Cell Gels | µL | Final Conc. |
|---|---|---|
| 1X TBSET | 100 | 0.1X |
| 4X AB | 250 | 1X |
| 10% APS | 30 | 0.3% |
| Cells/1X PBST | 620 | 6 M/mL |
| Total | 1000 | |

This yields approximately 20% singlet cells and 5% doublet cells. Cell gels are approximately 30 µm diameter on creation and 45 µm after polymerization and swelling in 1×PBS.

Cell Preparation

Cells should be fixed and permeabilized before starting. Most other modifications should be ok (i.e., mipping, LabelX). Note: If mipping, LabelX-ing, or doing other procedures with a lot of centrifugations, prepare as many cells as possible, as there will be loss due to clumping.

1. View and count fixed cells. Cells should be in singlets (with few doublets).
2. Filter cells if necessary with a 10 µm filter by wetting the filter with 100 µL 1×PBST, then passing through the cells.
   a. Note: If possible, do not centrifuge the cells post-filtration.
3. Ideally, cell concentration post-filtration will be 8-10M/mL.
   a. If cell concentration is very low (<2M/mL), then consider spinning cells down at either 850 g for 5 min (pre-filtration) or 300-500 g for 3-5 min (post-filtration).
   Note: I usually don't centrifuge post-filtration, because any centrifugation results in clumping.
   b. Lower cell concentration is ok; however, the resulting hydrogels may be very underpopulated, resulting ultimately in lowly populated droplets in emulsion experiments.

Cell Gel Generation Protocol

Figure 25:
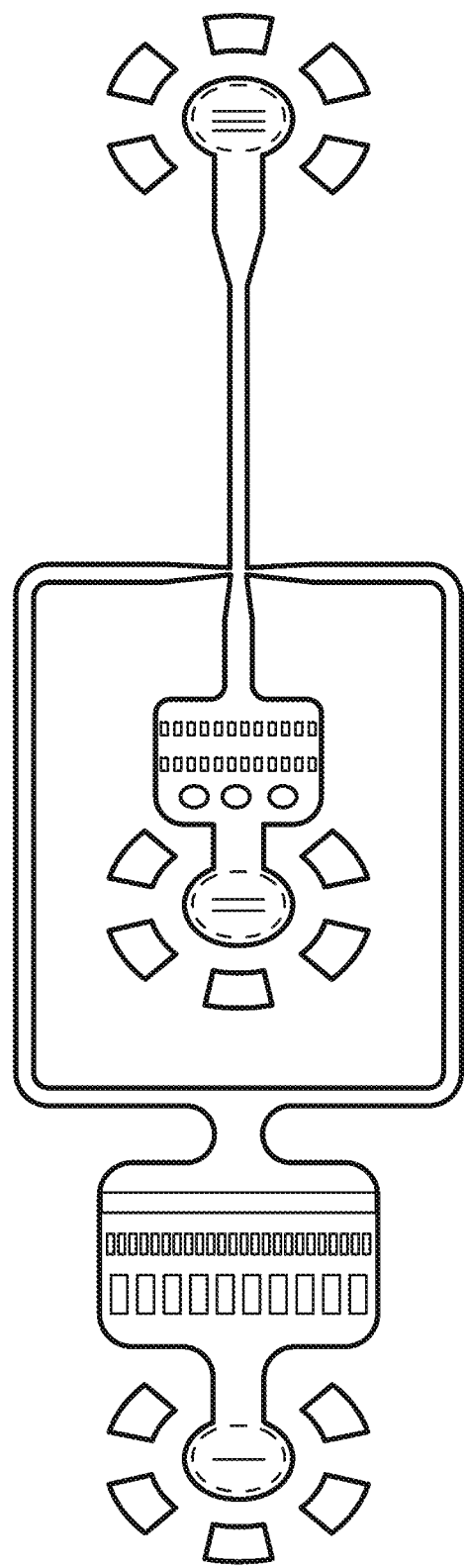
FIG. 25—Schematic of the droplet generator design (from Drop-Seq) that is used for making cell gels.

FIG. 25 shows the droplet generator design (from Drop-Seq) that is used for making cell gels. This droplet generator makes droplets that are 30-55 µm in diameter.

Keep reagents on ice until loading.

1. Prepare cell gel recipe with all ingredients except 4× AB and cells.
2. Prepare emulsion oil using a 1:100 ratio of TEMED to BioRad Droplet Generation Oil for Evagreen (e.g., for 5 mL of oil, add 50 µL of TEMED).
3. Prepare tubing and needles. Tubing length will vary depending on syringe distance from microfluidic chip.
4. Load 2.5 mL emulsion oil into a 3-mL syringe using a P-1000 pipette. Attach needle and tubing and prime.
5. At this point, mix 4× AB and cells (see recipe above) into the rest of the acrylamide mix. Load 1 mL of the acrylamide mix into a syringe. Syringe size may vary, depending on if you are padding the syringe with HFE (i.e., if you have 1 mL of acrylamide mix, but 250 µL of HFE on top of that, then you may have to use a 3-mL syringe instead of a 1-mL syringe). Attach needle and tubing and prime.
6. Insert tubings into the appropriate inlets on the microfluidic chip, as well as an outlet tubing with the other end in a 5-mL eppendorf. Begin flowing the chip at a roughly 1:2 or 1:3 rate (1 part aqueous, 2-3 parts oil). One can start with 1000 µL/hr for the acrylamide mix and 2000 µL/hr for the emulsion oil. After the flow stabilizes, check droplet size using a Fuchs-Rosenthal hemocytometer and adjust flow rate as necessary. Once the hydrogels are roughly 30-50 µm in diameter, begin collection. The duration of collection depends on the volume of acrylamide mix and emulsion oil, as well as flow rate.
   a. One can collect the first 1-2 minutes of output (roughly 50-100 µL) as waste, in a separate eppendorf from my actual hydrogels.
7. Post collection, discard needles and syringes in the appropriate sharps waste, and other reagents into the appropriate biohazardous waste.
8. Polymerize your hydrogels under a vacuum for 30 min at RT. Be sure to pop the top of the eppendorf.

Cell Gel Wash and Cleanup

1. After the hydrogels are polymerized, aspirate the extra emulsion oil from the bottom of the eppendorf. Fill the 5-mL eppendorf with wash buffer, then add 100 µL PFO.
2. Vortex and invert to mix well. Be sure there are any stragglers left on the bottom of the eppendorf.

3. Centrifuge for 3 min at 3000 g. The hydrogels should form three layers. From bottom to top: PFO, hydrogels, wash buffer.

4. Aspirate the bottom layer of PFO, then the top layer of wash buffer. Fill eppendorf with 5 mL of 1×TBSET. Centrifuge for 5 min at 1000 g.

5. Aspirate any remaining PFO, and aspirate the 1×TBSET. Fill again with 5 mL of 1×TBSET and centrifuge for 5 min at 1000 g. Repeat until there is no longer any remaining PFO.

6. Store hydrogels in the dark at 4° C. for up to 6 months.

Reverse Crosslinking Cell in Gels

Digestion Protocol

Cell gels were stored in 1×PBS at 4° C. Unless otherwise stated, all centrifugations were 5 min @ 1000 g RT.

Check hydrogels with SYBR Gold by diluting 10 μL of hydrogels in 10 μL of 1×PBS, spiked with 1 μL of 100× SYBR Gold (final concentration: 5×SYBR Gold).

1. Wash gels (up to 250 μL) in digestion buffer.

TABLE 9

| Digestion Buffer | μL | Final |
| --- | --- | --- |
| 1M Tris HCl (pH 8.0) | 50 | 50 mM |
| 0.5M EDTA | 20 | 10 mM |
| 10% SDS | 50 | 0.5% |
| Water | 880 | |
| Total | 1000 | | a. Centrifuge
b. Aspirate 1×PBS
c. Resuspend in twice the volume digestion buffer (e.g., if you have 200 μL of packed gels, resuspend in 400 μL of digestion buffer)
d. Centrifuge
e. Resuspend in 1× DB.
f. Centrifuge 2. Dilute Proteinase K (800 U/mL) 1:100 in digestion buffer, for a final concentration of 8 U/mL. Resuspend gels in twice the volume ProtK (e.g., if you have 200 μL of packed gels, resuspend in 400 μL of ProtK)

3. Incubate at 60° C. for 3 hrs without shaking.

4. Wash twice in 1×PBS.
a. Centrifuge
b. Aspirate ProtK
c. Resuspend in 1 mL of 1×PBS
d. Centrifuge
e. Repeat a-d 2× for a total of three washes 5. Resuspend gels in twice the volume 1×PBS or continue to alkaline denaturation step.

Check hydrogels with SYBR Gold by diluting 10 μL of hydrogels in 10 μL of 1×PBS, spiked with 1 μL of 100× SYBR Gold (final concentration: 5×SYBR Gold).

If checking hydrogels with SYBR Gold, be sure hydrogels are suspended in 1×PBS, not digestion or alkaline denaturation buffer.

Alkaline Denaturation

Unless otherwise stated, all centrifugations were 5 min @ 1000 g RT.

1. For every 100 μL of cell gels, use 250 μL of alkaline denaturation buffer.

TABLE 10

| Denaturation Buffer | μL | Final |
| --- | --- | --- |
| 0.1M DTT | 125 | 50 mM |
| 1M NaOH | 50 | 200 mM |
| Water | 75 | |
| Total | 250 | |

2. Incubate samples on ice for 10 min, then at 65° C. for 10 min.

3. Neutralize the reaction with 250 μL of neutralization buffer.

TABLE 11

| Neutralization Buffer | μL | Final |
| --- | --- | --- |
| 1M Tris HCl pH 8.5 | 181.25 | 720 mM |
| 2M KCl | 18.75 | 300 mM |
| 1M HCl | 50 | 200 mM |
| Total | 250 | |

4. Centrifuge
5. Resuspend in 1 mL 1×PBS
6. Centrifuge
7. Repeat steps 5-6 (washes) at least 2× for a total of at least 3 washes

Check hydrogels with SYBR Gold by diluting 10 μL of hydrogels in 10 μL of 1×PBS, spiked with 1 μL of 100× SYBR Gold (final concentration: 5×SYBR Gold).

If you see no signal with SYBR Gold, wash 3 more times with 1 mL 1×PBS, then check again.

MDA Protocol—LW

MDA Mix aka amplification buffer (prepare fresh). Modified from original Chen lab protocol, which left 5 μL for sample. It can just be filled to 50 μL with water.

TABLE 12

| Item | Quantity |
| --- | --- |
| 10X phi29 buffer | 5 μL |
| 1 mM random hexamers | 2.5 μL |
| dNTP (10 mM) | 5 μL |
| Water | 36.5 μL |
| phi29 polymerase | 1 μL |
| Total | 50 μL |

TABLE 13

| Item | Quantity |
| --- | --- |
| 10X phi29 buffer | 5 μL |
| 0.77 mM (3 μg/μL) random hexamers | 3.25 μL |
| dNTP (10 mM) | 5 μL |
| Water | 35.75 μL |
| phi29 polymerase | 1 μL |
| Total | 50 μL |

MDA Temperature Protocol

30° C. 3 hr
65° C. 10 min→changed from 3 min on Feb. 15, 2019
4° C. ∞

1. Resuspend gels in MDA mix (up to 100 μL) and incubate as specified.

2. After incubation, centrifuge and resuspend in 1 mL 1×PBS. Wash at least 3 times.

Check hydrogels with SYBR Gold by diluting 10 µL of hydrogels in 10 µL of 1×PBS, spiked with 1 µL of 100× SYBR Gold (final concentration: 5×SYBR Gold).

If you see no signal with SYBR Gold, wash 3 more times with 1 mL 1×PBS, then check again.

Genotyping in Emulsions

Reagents

TABLE 14

The polymerase mix with barcoded beads.

| Recipe (3PS) | µL | Negative Ctrl |
|---|---|---|
| 2X SM | 25 | 25 |
| P5-T7 (10 µM) | 2.5 | 2.5 |
| P7-splint (2.5 µM) | 2.5 | 2.5 |
| Barcoded Beads | 6.25 | 6.25 |
| Cell gels | 5 | 0 |
| Water | 8.75 | 13.75 |
| Total | 50 | 50 |

TABLE 15

The polymerase mix with free primer as control.

| Recipe (3PS) | µL | Negative Ctrl |
|---|---|---|
| 2X SM | 25 | 25 |
| P5-T7 (10 µM) | 2.5 | 2.5 |
| P7-splint (2.5 µM) | 2.5 | 2.5 |
| Free barcoded primer | 2.5 | 2.5 |
| Cell gels | 5 | 0 |
| Water | 12.5 | 17.5 |
| Total | 50 | 50 |

TABLE 16

The polymerase mix just internal primers as control for IVT.

| Recipe (2P-S) | µL | Negative Ctrl |
|---|---|---|
| 2X SM | 25 | 25 |
| P5-T7 (10 µM) | 2.5 | 2.5 |
| P7-splint (2.5 µM) | 2.5 | 2.5 |
| CIGs_KZ | 5 | 0 |
| Water | 15 | 20 |
| Total | 50 | 50 |

TABLE 17

The polymerase mix with barcoded beads.

| Recipe (3PS) | µL | Negative Ctrl |
|---|---|---|
| 2X SM | 25 | 25 |
| P5-T7 (10 µM) | 2.5 | 2.5 |
| P7-splint (2.5 µM) | 2.5 | 2.5 |
| Barcoded Beads | 6.25 | 6.25 |
| Cell gels | 5 | 0 |
| Water | 8.75 | 13.75 |
| Total | 50 | 50 |

TABLE 18

The polymerase mix with free primer as control.

| Recipe (3PS) | µL | Negative Ctrl |
|---|---|---|
| 2X SM | 25 | 25 |
| P5-T7 (10 µM) | 2.5 | 2.5 |
| P7-splint (2.5 µM) | 2.5 | 2.5 |
| Free barcoded primer | 2.5 | 2.5 |
| Cell gels | 5 | 0 |
| Water | 12.5 | 17.5 |
| Total | 50 | 50 |

TABLE 19

The polymerase mix just internal primers as control for IVT.

| Recipe (2P-S) | µL | Negative Ctrl |
|---|---|---|
| 2X SM | 25 | 25 |
| P5-T7 (10 µM) | 2.5 | 2.5 |
| P7-splint (2.5 µM) | 2.5 | 2.5 |
| CIGs_KZ | 5 | 0 |
| Water | 15 | 20 |
| Total | 50 | 50 |

Setting up Emulsions

Figure 26:
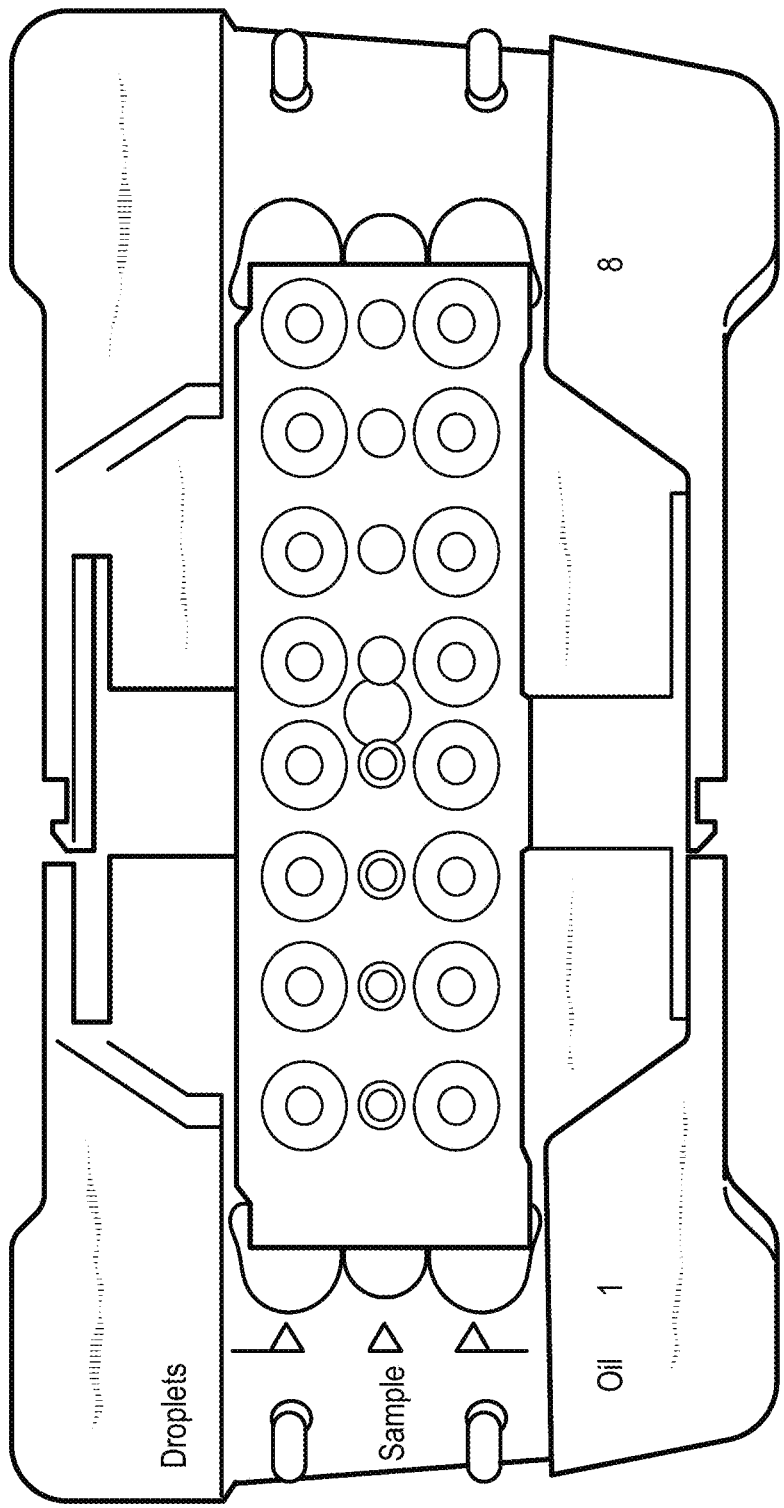
FIG. 26—shows Biorad cartridge and cartridge holder.

1. The ddPCR Biorad cartridge was loaded into the holder as shown in FIG. 26. The cartridge holder was then locked in place. In the sample well (indicated as sample ➤) 20 ul each of the polymerase mix is first loaded.

2. In the oil wells (indicated as oil ➤) load 70 ul each of the ddPCR Evagreen oil mix ( )

3. All wells should be filled. Empty sample wells can be filled with 20 ul of 1×PBS.

Figure 27:
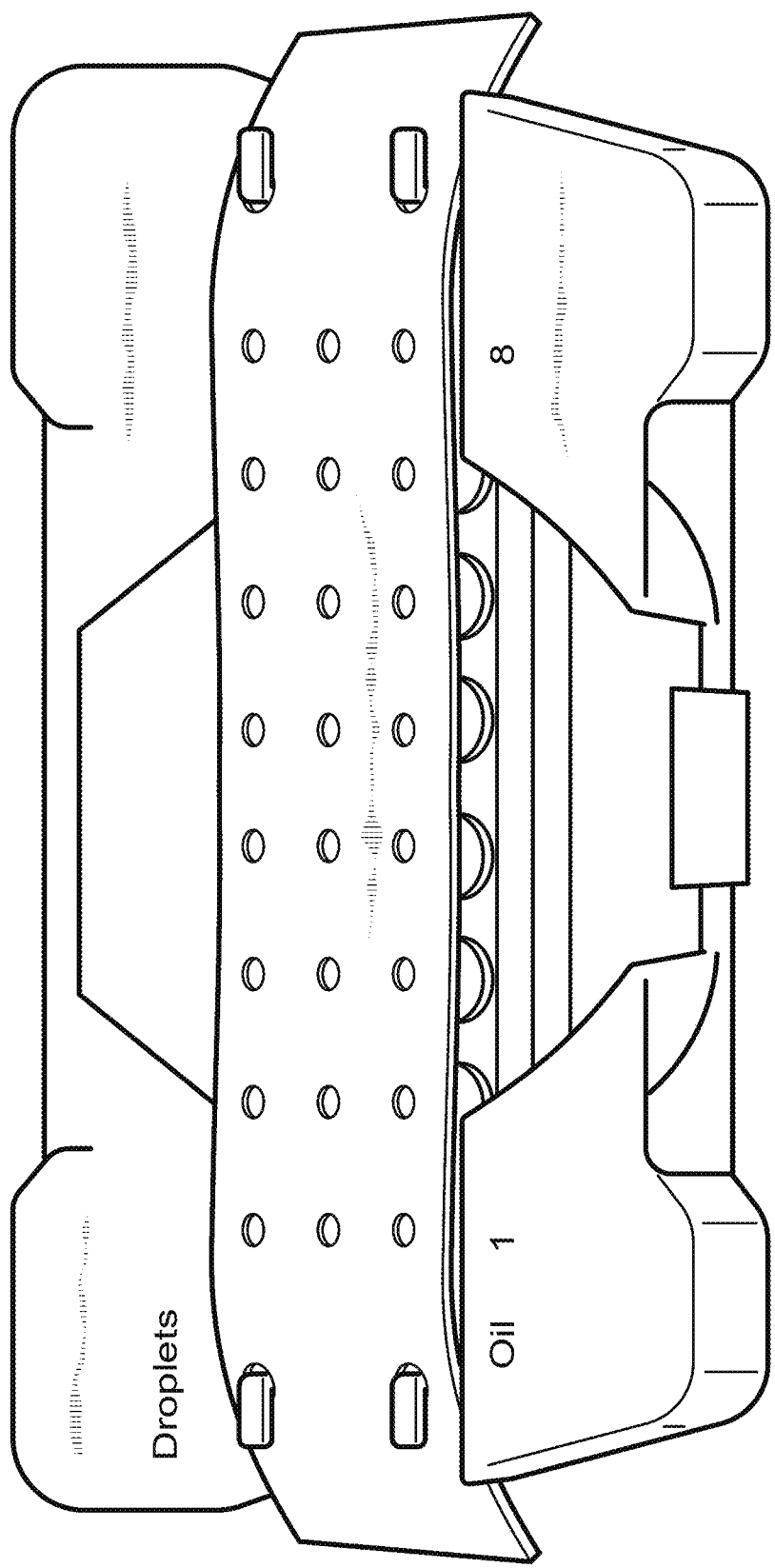
FIG. 27—shows Biorad cartridge and cartridge holder covered with a gasket.

4. Once the polymerase mix and oil is loaded and all sample and oil wells are full, the gasket is placed over the cartridge as shown in FIG. 27.

Figure 28B:
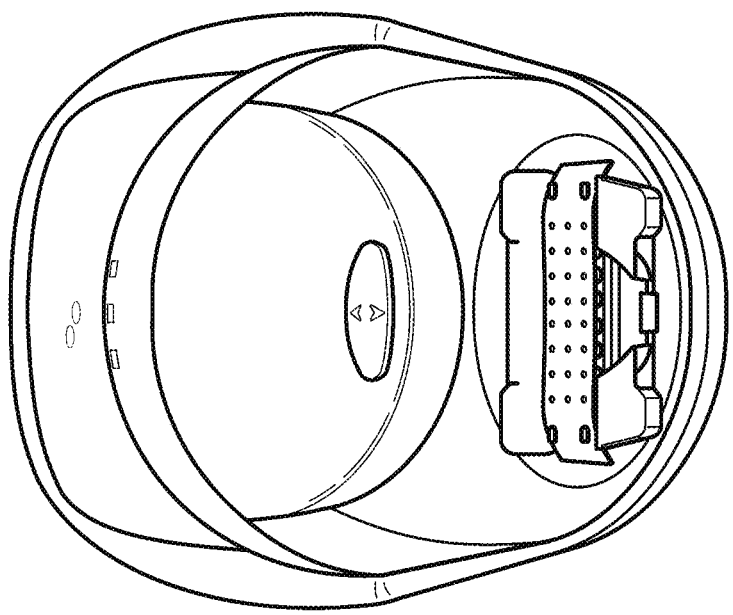
FIGS. 28A, 28B—shows different views of the Biorad ddPCR machine, both (FIG. 28A) closed and (FIG. 28B) open.
Figure 28A:
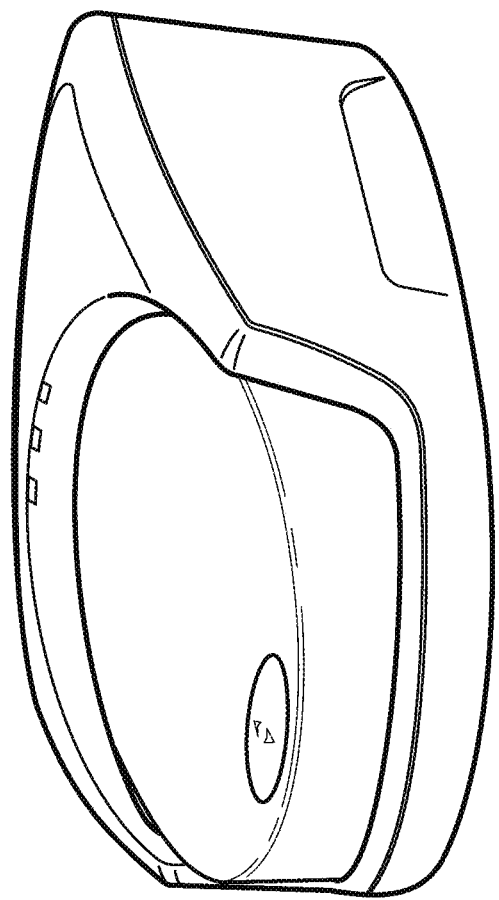

5. The filled and gasket-covered cartridge is loaded into the ddPCR machine as shown in FIGS. 28A and 28B.

6. The lid is closed and the process of droplet generation is initiated by pressing the ↑ button on the lid. When droplet generation is complete, all three indicator lights are solid green. The holder is removed (with cartridge still in place) from the unit. The disposable gasket from the holder is removed and discarded. The top wells now contain droplets (indicated by the label Droplets ➤ in cartridge), and the middle and lower wells are nearly empty with a small amount of residual oil.

7. All the contents of the droplet wells are removed from the cartridge using a low retention pipette tips ( ) and transferred to a semi-skirted PCR (Eppendorf—951022043—PLATE PCR SEMI SKIRTD BLU CS25 (Case of 25).

8. The plates with the emulsions are sealed with foil provided (PCR Plate Heat Seal, foil, pierceable #1814040) and using the BioRad Plate sealer as per manufacturer's instructions (PX1™ PCR Plate Sealer).

9. The sealed plate was then subject to PCR ( ) using the following cycling parameters.

TABLE 20

| PCR Conditions | | |
| --- | --- | --- |
| 95* | 2:00 | |
| 95* | 0:30 | X 20-30 |
| Tm* | 1:00 | |
| 72* | 1:00 | |
| 72* | 2:00 | |
| 10 | ∞ | |

*2° C./sec ramp rate

Breaking up Emulsions

10. Once the PCR is complete, only the emulsion layer is pooled (when possible) and transferred into a fresh strip tube.

11. PFO (1H,1H,2H,2H-Perfluoro-1-octanol) (Sigma) was added to the emulsions to a final concentration of 20% by volume (For example, if you have roughly 100 μL of emulsions (not including carrier oil), add 20 μL of PFO).

12. The PFO and emulsion mix was vortexed for 5 s at around 3000 rpm. The suspension was then spun for 15-20s on a tabletop centrifuge until the emulsions were completely broken.

13. The aqueous layer was then transferred to a fresh tube and cleaned by adding AMPure XP beads (Beckman Coulter, A63882) at a 1.2×-1.8× ratio and eluted in 15 ul in 10 mM TrisHCl ph 7.5.

T7 Protocol

In Vitro Transcription (IVT) and DNase Treatment

14. The SPRI cleaned PCR samples were then used to perform IVT with the following reagents:

TABLE 21

| Recipe (IVT) | μL |
| --- | --- |
| Nuclease free water | 11 |
| 10X T7 polymerase mix | 2 |
| NTP mix (25 mM each) N2052A | 10 |
| 10X buffer mix | 2 |
| PCR Template | 5 |
| Total | 30 |

15. The IVT reaction was incubated at 37° C. O/N.

16. After the IVT reaction was complete, 1 ul of DNAse (NEB, M0303L) was added to the post-IVT reaction and incubated at 37° C. for 15 mins.

17. After DNAse treatment, the reaction mix was cleaned with RNAClean XP (Beckman Coulter, A66514) according to manufacturer's instructions.

cDNA Synthesis

18. The cleaned post IVT mix was then used to generate cDNA with the following reagents:

TABLE 22

| Recipe (cDNA synthesis) | μL |
| --- | --- |
| Nuclease free water | 0 |
| dNTPs (10 mM) | 1 |
| Primer against P7 sequence (5 uM) | 1 |
| IVT RNA (1 pg-5 ug) | 8 |
| Total | 10 |

Incubate the mixture above at 65° C. for 5 mins and place on ice for 1 min.

19. The following reagents were then added to the incubated mix (above)—

TABLE 23

| Recipe (cDNA synthesis) | μL |
| --- | --- |
| 10X RT Mix | 2 |
| 0.1M DTT | 2 |
| 25 mM MgCl2 | 4 |
| RNAseOut (40 U/ul) | 1 |
| SuperScript III RT (200 U/ul) | 1 |
| Total | 10 |

The complete RT mix was then incubated as follows:

TABLE 24

| Incubate | Time |
| --- | --- |
| 50° C. | 50 min |
| 85° C. | 5 min |
| 4° C. | 4EVA |

Final Amplification with Index Primers

20. To add the Illumina index primers to the cDNA product, the following reaction mix prepared:

TABLE 25

| Recipe (for indexing) | μL |
| --- | --- |
| 2X Q5 | 25 |
| P5-index (10 μM) | 2.5 |
| P7-fwd (10 μM) | 2.5 |
| cDNA PCR template | 1 |
| Water | 19 |
| Total | 50 |

The following PCR cycling conditions were used—

TABLE 26

| Indexing PCR | | |
| --- | --- | --- |
| 95 | 2:00 | |
| 95 | 0:30 | X20 |
| 61 | 1:00 | |
| 72 | 1:00 | |
| 72 | 2:00 | |
| 10 | ∞ | |

21. The final library mix is cleaned with AMPure XP beads at a ratio of 0.8×. The cleaned library is quantified using Qubit.

Example 14—Guide Detection in Bulk

Figure 29:
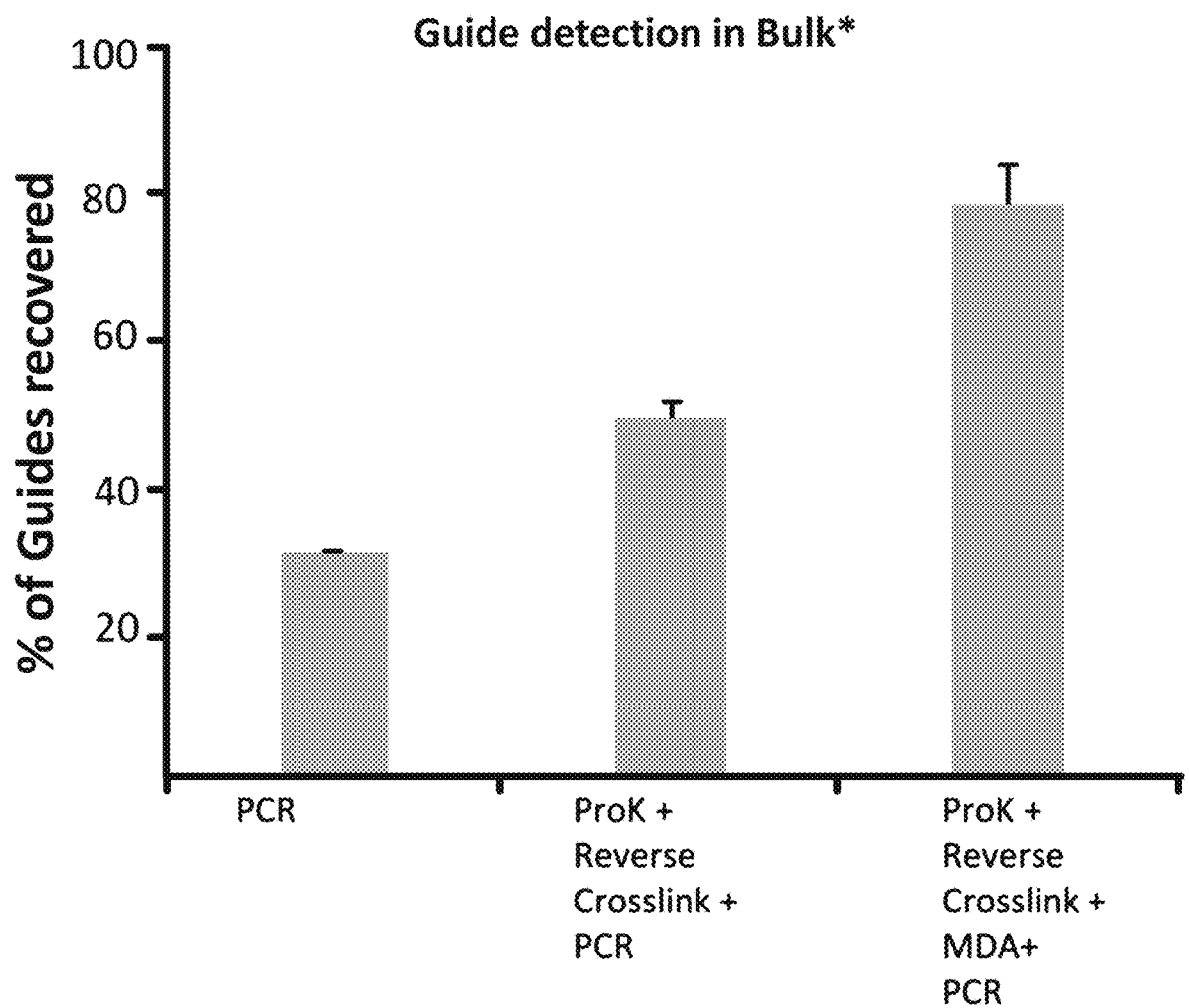
FIG. 29—shows results of guide detection in bulk, indicating that the proteinase K, reverse crosslinking and whole genome amplification conditions allowed for maximum (>80%) guide recovery. Free/soluble primers were used for these experiments. *With soluble primers FIG. 30—shows qPCR for GAPDH probes. Results indicate that acrylated probes help retain the Gapdh probes in the cell encapsulated in acrylamide and subject to the proteinase K, Reverse crosslinking and whole genome amplification compared to probes that are not acrylated (the two right bars in each group vs the two left bars).

Guides from 1000 cells each containing unique guides were recovered by Illumina sequencing by amplification via PCR without any treatment, amplification following Proteinase K and reverse crosslinking and finally amplification following Proteinase K, reverse crosslinking and whole gene amplification via MDA using phi29 polymerase. Results in FIG. 29 indicate the proteinase K, reverse crosslinking and whole genome amplification conditions allowed for maximum (>80%) guide recovery. Free/soluble primers were used for these experiments.

Example 15—qPCR for GAPDH Probes

Figure 30:
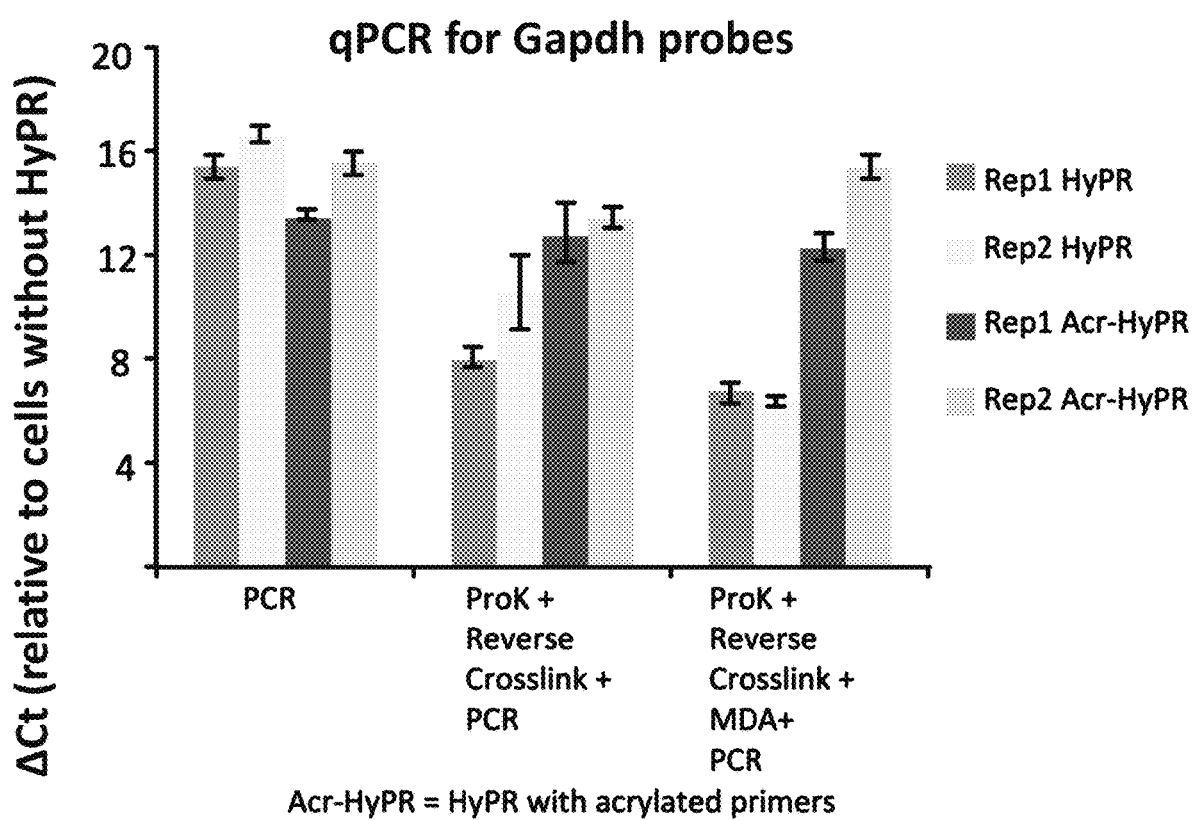

Quantitative qPCR was performed to determine the relative enrichment of Gapdh HyPR probes in cells encapsulated in acrylamide (relative to cells without HyPR probes) that were subjected to proteinase K, reverse crosslinking and whole genome amplification. Applicant performed these analyses on two biological replicates (K562 cells) with and without the presence of acrylated HyPR probes (Acr-HyPR). Results from these data (FIG. 30) show that acrylated probes help retain the Gapdh probes in the cell encapsulated in acrylamide and subject to the proteinase K, Reverse crosslinking and whole genome amplification compared to probes that are not acrylated (purple vs green bars).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of analyzing nucleic acids, comprising:
providing two targeting probes capable of hybridizing a target nucleic acid, whereby the targeting probes bind to a target region in the target nucleic acid and together form an initiator sequence when both targeting probes are bound to the target sequence, wherein the initiator sequence is not hybridized to the target region, wherein the first targeting probe comprises a sequencing adaptor and UMI;
providing a first sensing oligo, whereby the first sensing oligo is a hairpin that binds to the initiator sequence, wherein the hairpin is opened by hybridization to the initiator to reveal a hybridization region;
providing a second sensing oligo comprising a sequencing adaptor, whereby the second sensing oligo binds to the first sensing oligo via the hybridization region in the first sensing oligo; and
attaching the second sensing oligo to the first targeting probe, thereby generating a sequencing construct.

2. The method of claim 1, wherein the at least one targeting probe is a first targeting probe, and the method further comprises providing a second targeting probe, whereby the first and the second targeting probes bind to first and a second target regions in the target nucleic acid, respectively.

3. The method of claim 2, further comprising thermodynamically regulating the binding of the first sensing oligo with the first and the second targeting probes.

4. The method of claim 2, wherein a distance between the first and the second target regions is 10 nt or less.

5. The method of claim 2, wherein the first or the second target region is from 10 nt to 200 nt in length.

6. The method of claim 2, wherein the first and the second targeting probes bind to a first and a second binding regions in the first sensing oligo, respectively.

7. The method of claim 6, wherein the first or the second binding region is from 10 nt to 100 nt in length.

8. The method of claim 1, wherein the sequencing construct comprises at least a portion of the second sensing oligo and at least a portion of the at least one targeting probe.

9. The method of claim 1, further comprising obtaining a sequence read of the sequencing construct.

10. The method of claim 9, further comprising analyzing the target nucleic acid based, at least in part, on the sequence read of the sequencing construct.

11. The method of claim 10, wherein analyzing the target nucleic acid comprises quantifying the target nucleic acid.

12. The method of claim 1, further comprising amplifying the sequencing construct, thereby generating a sequencing library comprising the amplified sequencing construct.

13. The method of claim 1, wherein the second sensing oligo comprises a primer binding site.

14. The method of claim 1, wherein the second sensing oligo is attached to the at least one targeting probe by ligation using a ligase.

15. The method of claim 14, wherein the at least one targeting probe comprises a 5' phosphate.

16. The method of claim 1, wherein, when attached, the second sending oligo and the at least one targeting probe form a loop structure.

17. The method of claim 1, wherein the at least one targeting probe comprises a sequencing adaptor.

18. The method of claim 1, wherein the at least one targeting probe comprises a primer binding site.

19. The method of claim 1, wherein the at least one targeting probe comprises a barcode.

20. The method of claim 19, wherein the barcode comprises a unique molecular identifier.

21. The method of claim 1, wherein the hybridization region in the second sensing oligo is less than 10 nt, less than 5 nt, or less than 3 nt in length.

22. The method of claim 1, wherein the target nucleic acid is in a cell, and the method further comprises fixing the cell.

23. The method of claim 1, wherein the first and the second sensing oligos are comprised in the same molecule.

24. The method of claim 1, wherein the target nucleic acid comprises mRNA or DNA derived therefrom.

25. The method of claim 1, wherein the adaptor in the second sensing oligo is at a 3' side of the hybridization region.

26. A system for analyzing nucleic acids, comprising:
a) a first targeting probe comprising:
  i) a first target binding sequence that hybridizes to a first target region in a target nucleic acid sequence, and
  ii) a first sequencing adaptor;
b) a second targeting probe comprising a second target binding sequence that hybridizes to a second target region adjacent to the first targeting in the target nucleic acid thereby creating an initiator sequence comprising portions of the first and second targeting probes;
c) a first hairpin sensing oligo comprising:
  i) a first binding region that hybridizes to the initiator sequence, and
  ii) a hybridization region that is exposed upon binding to the initiator sequence and is configured so that the hybridization region is positioned proximate to an end of the first target probe opposite the existing sequence adaptor; and
d) a second sensing oligo comprising:
  i) a hybridization region that hybridizes to the hybridization region of the first sensing oligo, and
  ii) a second sequencing adaptor.

27. The system of claim 26, wherein a distance between the first and second target region is 10 nt or less.

28. The system of claim 26, wherein the first or the second target region is from 10 nt to 200 nt in length.

29. The system of claim 26, wherein the first or the second binding region is from 10 nt to 100 nt in length.

30. The system of claim 26, wherein the second sensing oligo comprises a primer binding site.

31. The system of claim 26, wherein the at least one targeting probe comprises a 5' phosphate.

32. The system of claim 26, wherein the at least one targeting probe comprises a primer binding site.

33. The system of claim 26, wherein the at least one targeting probe or sensing oligo comprises a barcode.

34. The system of claim 33, wherein the barcode comprises a unique molecular identifier.

35. The system of claim 26, wherein the hybridization region in the second sensing oligo is less than 10 nt, less than 5 nt, or less than 3 nt in length.

36. The system of claim 26, wherein the adaptor in the second sensing oligo is at a 3' side of the hybridization region.

37. The system of claim 26, further comprising one or more primers configured to bind to at least a portion of the first targeting probe.

38. The system of claim 26, further comprising one or more primers configured bind to at least a portion of the second sensing oligo.

39. A sequencing library comprising sequencing constructs prepared using the method of claim 1.

40. The method of claim 1 in which the oligos detect nucleic acids inside of cells, and the cells are first cross-linked and permeabilized prior to applying the oligos.

* * * * *